(12) United States Patent
Sagehashi et al.

(10) Patent No.: US 9,207,534 B2
(45) Date of Patent: *Dec. 8, 2015

(54) NITROGEN-CONTAINING MONOMER, POLYMER, RESIST COMPOSITION, AND PATTERNING PROCESS

(75) Inventors: Masayoshi Sagehashi, Joetsu (JP); Jun Hatakeyama, Joetsu (JP); Takeru Watanabe, Joetsu (JP); Tomohiro Kobayashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 9 days.

This patent is subject to a terminal disclaimer.

(21) Appl. No.: 13/349,754

(22) Filed: Jan. 13, 2012

(65) Prior Publication Data

US 2012/0183904 A1    Jul. 19, 2012

(30) Foreign Application Priority Data

Jan. 14, 2011    (JP) ................................ 2011-005428

(51) Int. Cl.
| | | |
|---|---|---|
| *G03F 7/039* | (2006.01) | |
| *G03F 7/004* | (2006.01) | |
| *G03F 7/30* | (2006.01) | |
| *G03F 7/20* | (2006.01) | |
| *C07D 211/44* | (2006.01) | |

(52) U.S. Cl.
CPC ............ *G03F 7/0397* (2013.01); *G03F 7/0045* (2013.01); *G03F 7/0046* (2013.01); *G03F 7/0392* (2013.01); *G03F 7/2037* (2013.01); *G03F 7/2039* (2013.01); *G03F 7/2041* (2013.01); *G03F 7/30* (2013.01); *C07D 211/44* (2013.01)

(58) Field of Classification Search
None
See application file for complete search history.

(56) References Cited

U.S. PATENT DOCUMENTS

| | | | |
|---|---|---|---|
| 5,879,851 A | 3/1999 | Takahashi et al. | |
| 6,312,867 B1 | 11/2001 | Kinsho et al. | |
| 7,537,880 B2 | 5/2009 | Harada et al. | |
| 7,771,913 B2 | 8/2010 | Kaneko et al. | |
| 7,960,091 B2 | 6/2011 | Shimizu et al. | |
| 2008/0090172 A1 | 4/2008 | Hatakeyama et al. | |
| 2008/0102407 A1* | 5/2008 | Ohsawa et al. ............ 430/286.1 |
| 2008/0153030 A1 | 6/2008 | Kobayashi et al. | |
| 2009/0042128 A1* | 2/2009 | Takemoto .................. 430/281.1 |
| 2009/0274978 A1 | 11/2009 | Ohashi et al. | |
| 2010/0151388 A1 | 6/2010 | Yang et al. | |

FOREIGN PATENT DOCUMENTS

| | | | |
|---|---|---|---|
| JP | 2000-336121 A | 12/2000 | |
| JP | 3429592 B2 | 7/2003 | |
| JP | 3790649 B2 | 6/2006 | |
| JP | 2006-178317 A | 7/2006 | |
| JP | 3995575 B2 | 10/2007 | |
| JP | 2007-297590 A | 11/2007 | |
| JP | 2007-298569 A | 11/2007 | |
| JP | 2008-111103 A | 5/2008 | |
| JP | 2008-122932 A | 5/2008 | |
| JP | 2008-133312 A | 6/2008 | |
| JP | 2008-158339 A | 7/2008 | |
| JP | 2009-181062 A | 8/2009 | |
| JP | 2009-269953 A | 11/2009 | |
| JP | 2010-61018 | * 3/2010 | |
| JP | 2011-209667 A | 10/2011 | |
| WO | WO 2011/083872 A1 | * 7/2011 | |

OTHER PUBLICATIONS

Machine-assisted English translation for JP 2011-209667, provided by JPO (2011).*
Derwent English abstract for JP 2010-61018 (2010).*
Machine-assisted English translation of JP 2010-61018, provided by JPO (2010).*
Japanese Office Action dated Apr. 23, 2013, issued in corresponding Japanese Patent Application No. 2011-005428 (4 pages).
Kishikawa, Yasuhiro et al., "Assessment of trade-off between resist resolution and sensitivity for optimization of hyper-NA immersion lithography", Proc. of SPIE, 2007, pp. 6520-65203L-1, vol. 6520.
Hinsberg, William et al., "Extendibility of Chemically Amplified Resists: Another Brick Wall?", Proc. of SPIE, 2003, pp. 1-14, vol. 5039.

* cited by examiner

*Primary Examiner* — Sin Lee
(74) *Attorney, Agent, or Firm* — Westerman, Hattori, Daniels & Adrian, LLP

(57) ABSTRACT

A chemically amplified positive resist composition of better performance can be formulated using a polymer having a quencher incorporated therein, specifically a polymer comprising recurring units having a carbamate structure which is decomposed with an acid to generate an amino group and optionally recurring units having an acid labile group capable of generating a carboxyl and/or hydroxyl group under the action of an acid. The polymer is highly effective for suppressing diffusion of acid and diffuses little itself, and the composition forms a pattern of rectangular profile at a high resolution.

13 Claims, No Drawings

US 9,207,534 B2

NITROGEN-CONTAINING MONOMER, POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2011-005428 filed in Japan on Jan. 14, 2011, the entire contents of which are hereby incorporated by reference.

TECHNICAL FIELD

This invention relates to a monomer having a specific carbamate structure; a polymer thereof; a positive resist composition, specifically a chemically amplified positive resist composition which lends itself to KrF excimer laser, ArF excimer laser, EB, and EUV lithography; and a patterning process using the composition.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, extreme ultraviolet (EUV) lithography of 13.5 nm wavelength, and double patterning version of the ArF lithography, on which active research efforts have been made.

With respect to high-energy radiation of very short wavelength such as electron beam (EB) or x-ray, hydrocarbons and similar light elements used in resist materials have little absorption. Then polyhydroxystyrene base resist materials are under consideration. Resist materials for EB lithography are practically used in the mask image writing application.

Recently, the mask manufacturing technology becomes of greater interest. Reduction projection exposure systems or steppers have been used since the time when the exposure light was g-line. While their demagnification factor was ⅕, a factor of ¼ is now used as a result of chip size enlargement and projection lens diameter increase. It becomes of concern that a dimensional error of a mask has an impact on the dimensional variation of a pattern on wafer. It is pointed out that as the pattern feature is reduced, the value of a dimensional variation on the wafer becomes greater than the value of a dimensional error of the mask. This is evaluated by a mask error enhancement factor (MEEF) which is a dimensional variation on wafer divided by a dimensional error of mask. Patterns on the order of 45 nm often show an MEEF in excess of 4. In a situation including a demagnification factor of ¼ and a MEEF of 4, the mask manufacture needs an accuracy substantially equivalent to that for equi-magnification masks.

The exposure system for mask manufacturing made a transition from the laser beam exposure system to the EB exposure system to increase the accuracy of line width. Since a further size reduction becomes possible by increasing the accelerating voltage of the electron gun in the EB exposure system, the accelerating voltage increased from 10 keV to 30 keV and reached 50 keV in the current mainstream system, with a voltage of 100 keV being under investigation.

In a chemically amplified resist composition comprising an acid generator which generates an acid upon exposure to light or EB to induce deprotection reaction, a quencher is often added for the purpose of controlling diffusion of the acid into the unexposed area for improving the contrast. Since the addition of such quenchers is quite effective, numerous amine quenchers have been proposed. As pointed out in the art, the amine quenchers give rise to a problem that the profile and size of a pattern vary due to evaporation and re-deposition of acid and amine quencher during bake. This phenomenon may occur on use of either a dark mask in which a peripheral portion of a line-and-space pattern is light shielded or a bright mask in which the peripheral portion is transparent. Since no light is irradiated in the peripheral portion of the dark mask, the amine quencher is in excess in the resist film. In the peripheral portion of the bright mask, the acid generated by light irradiation is in excess. While the deformation of pattern by evaporation and re-deposition of acid has been mainly discussed, evaporation of amine quencher is also troublesome.

As the acid generator, alkylsulfonium salts such as 4-alkoxy-1-naphthyltetrahydrothiophenium cations were developed. These alkylsulfonium salts are susceptible to nucleophilic displacement reaction by amines or the like so that the resist solution may increase its sensitivity. Their low stability is a problem. It would be desirable to have an amine quencher which does not induce nucleophilic displacement reaction to these acid generators. Although those amine quenchers of weak bases such as pyridine and aniline do not induce nucleophilic displacement reaction, undesirably they have low acid trapping and acid diffusion controlling capabilities.

While the EUV and EB lithography processes involve exposure in vacuum, a sensitivity increase due to evaporation of the quencher during exposure is pointed out. Also image blur by diffusion of amine quencher is pointed out. It would be desirable to have a quencher which does not adversely affect the stability of a resist composition, does not substantially evaporate or diffuse by heat, and has a good acid trapping capability.

Heretofore, resist resins in the form of polymers having amine incorporated in polymer units have been proposed for the purposes of reducing leach-out of basic components during exposure by immersion lithography and improving lithography properties such as depth of focus (DOF) (see JP-A 2008-133312 and JP-A 2009-181062). These resins are effective for controlling volatilization and diffusion of quenchers, but are still insufficient in roughness reduction or the like.

Also a variety of carbamate quenchers such as tert-butoxycarbonyl amine have been developed for the purposes of improving the margin of an isolated pattern and improving the stability of resist composition (see JP 3790649 and JP-A 2007-298569). These carbamate quenchers are low basic and effective for improving the stability of the foregoing acid generators, but are still unsatisfactory with respect to the control of volatilization and diffusion of the quencher.

CITATION LIST

Patent Document 1: JP-A 2008-133312
Patent Document 2: JP-A 2009-181062

Patent Document 3: JP 3790649
Patent Document 4: JP-A 2007-298569
Non-Patent Document 1: SPIE Vol. 5039 p 1 (2003)
Non-Patent Document 2: SPIE Vol. 6520 p 65203L-1 (2007)

SUMMARY OF INVENTION

An object of the invention is to provide a positive resist composition, typically chemically amplified positive resist composition, which has a high resolution surpassing prior art positive resist compositions and a good process adaptability, and forms a pattern of rectangular profile with minimal roughness after exposure; a polymer serving as a base resin in the resist composition; a monomer for forming the polymer; and a patterning process using the resist composition.

Seeking for a higher resolution resist composition to meet the recent demand, the inventors have found that a chemically amplified positive resist composition of better performance can be formulated using a polymer comprising recurring units having a carbamate structure which is decomposed with an acid to generate an amino group and optionally recurring units having an acid labile group capable of generating a carboxyl and/or hydroxyl group under the action of an acid. Since the polymer is highly effective for suppressing diffusion of acid and diffuses little itself, the composition forms a pattern at a high resolution and rectangularity. Since the polymer does not evaporate in vacuum, the composition is best suited for the EB or EUV lithography. The present invention is predicated on this finding.

In one aspect, the invention provides a monomer having the general formula (1):

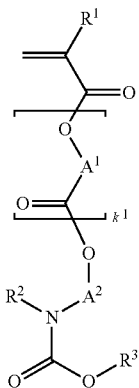

(1)

wherein $R^1$ is hydrogen, fluorine, methyl or trifluoromethyl, $R^2$ is hydrogen or a straight, branched or cyclic, mono or divalent hydrocarbon group of 1 to 10 carbon atoms, $R^3$ is an acid labile group of 1 to 15 carbon atoms, $A^1$ is a straight, branched or cyclic, divalent hydrocarbon group of 1 to 10 carbon atoms, $A^2$ is a straight, branched or cyclic, di or trivalent hydrocarbon group of 1 to 10 carbon atoms, $A^2$ and $R^2$ may bond together to form a ring with the adjacent nitrogen atom, $k^1$ is 0 or 1, with the proviso that when $k^1=0$, $R^3$ is an acid labile group selected from the following:

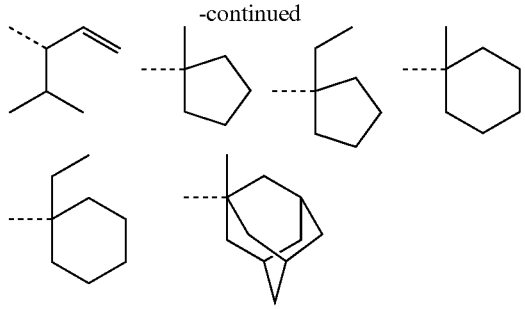

wherein the broken line denotes a valence bond.

In another aspect, the invention provides a polymer comprising recurring units (a) having the general formula (2):

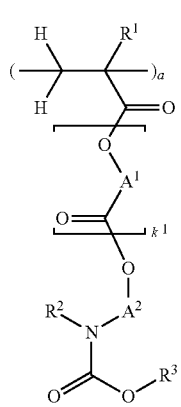

(2)

wherein $R^1$, $R^2$, $R^3$, $A^1$, $A^2$, and $k^1$ are as defined above, and "a" is a number in the range: $0<a<1.0$.

One preferred embodiment is a polymer comprising, in copolymerized form, recurring units (a) having formula (2) defined above and recurring units having an acid labile group capable of generating a carboxyl and/or hydroxyl group under the action of an acid.

In a further preferred embodiment, the recurring units having an acid labile group capable of generating a carboxyl and/or hydroxyl group under the action of an acid comprise recurring units (b) or (c) having the general formula (3):

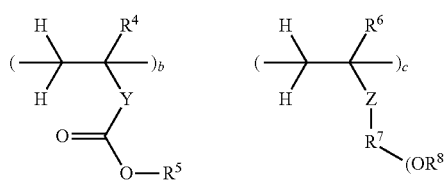

(3)

wherein $R^4$ and $R^6$ each are hydrogen or methyl, $R^5$ and $R^8$ each are an acid labile group, $R^7$ is a straight, branched or cyclic alkylene group of 1 to 10 carbon atoms or a trivalent form of the alkylene group with one hydrogen eliminated, which may contain an ether or ester moiety, or a phenylene or naphthylene group, Y is a single bond or —C(=O)—O—$R^9$—, $R^9$ is a straight, branched or cyclic alkylene group of 1 to 10 carbon atoms which may contain an ether or ester moiety, or a phenylene or naphthylene group, Z is a single bond or —C(=O)—O—$R^{10}$—, $R^{10}$ is a straight, branched or cyclic alkylene group of 1 to 10 carbon atoms which may contain an ether or ester moiety, or a phenylene or naphthylene group, the phenylene and naphthylene groups may be substituted with fluorine, trifluoromethyl, cyano, amide or $C_1$-$C_6$ alkyl or alkoxy radical, n is 1 or 2, b and c are numbers in the range: 0≤b<1.0, 0≤c<1.0, and 0<b+c<1.

The polymer may further comprise recurring units (d) having an adhesive group copolymerized with the recurring units (a), (b), and (c), said adhesive group being selected from the group consisting of hydroxyl, carboxyl, lactone ring, carbonate, thiocarbonate, carbonyl, cyclic acetal, ether, ester, sulfonic acid ester, cyano, amide, and —O—C(=O)-G- wherein G is sulfur or NH.

In a further aspect, the invention provides a positive resist composition comprising the polymer defined above and an organic solvent.

The positive resist composition may further comprise an acid generator, wherein the composition is a chemically amplified resist composition, and optionally, a basic compound and/or a surfactant.

In a still further aspect, the invention provides a pattern forming process comprising the steps of coating the positive resist composition defined above onto a substrate, baking, exposing to high-energy radiation, and developing with a developer. The high-energy radiation is typically selected from g-line, i-line, KrF excimer laser, ArF excimer laser, electron beam, and soft x-ray with a wavelength 3 to 15 nm.

ADVANTAGEOUS EFFECTS OF INVENTION

Since the polymer is highly effective for controlling diffusion of acid and suppressing volatilization and diffusion of the quencher component, the positive resist composition has advantages including a high resolution, exposure latitude, process adaptability, good pattern profile after exposure, minimal line edge roughness, and dimensional stability in vacuum. Because of these advantages, the positive resist composition is feasible by commercial lithography and best suited as a VLSI-forming resist material and mask pattern-forming material.

DESCRIPTION OF EMBODIMENTS

The singular forms "a", "an" and "the" include plural references unless the context clearly dictates otherwise. The notation (Cn-Cm) means a group containing from n to m carbon atoms per group. The abbreviation EB stands for electron beam, EUV for extreme ultraviolet, PAG for photoacid generator, PEB for post-exposure bake, LER for line edge roughness, and LWR for line width roughness.

Throughout the disclosure, the broken line depicted in a chemical formula denotes a valence bond.

Monomer

Seeking for a compound which when formulated in a resist composition, has a high resolution and process adaptability and forms a satisfactory pattern of rectangular profile with minimal LER after exposure, we have found that a nitrogen-containing monomer having the general formula (1) below can be readily prepared in high yields by the method described later, and that a polymer obtained from polymerization of this monomer can be used to formulate a chemically amplified positive resist composition that forms a pattern of rectangular profile and minimal LER at a high resolution.

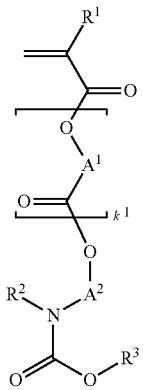

(1)

Herein $R^1$ is hydrogen, fluorine, methyl or trifluoromethyl, $R^2$ is hydrogen or a straight, branched or cyclic, mono or divalent hydrocarbon group of 1 to 10 carbon atoms, $R^3$ is an acid labile group of 1 to 15 carbon atoms, $A^1$ is a straight, branched or cyclic, divalent hydrocarbon group of 1 to 10 carbon atoms, $A^2$ is a straight, branched or cyclic, di or trivalent hydrocarbon group of 1 to 10 carbon atoms, $A^2$ and $R^2$ may bond together to form a ring with the adjacent nitrogen atom, $k^1$ is 0 or 1, with the proviso that when $k^1$=0, $R^3$ is an acid labile group selected from the following:

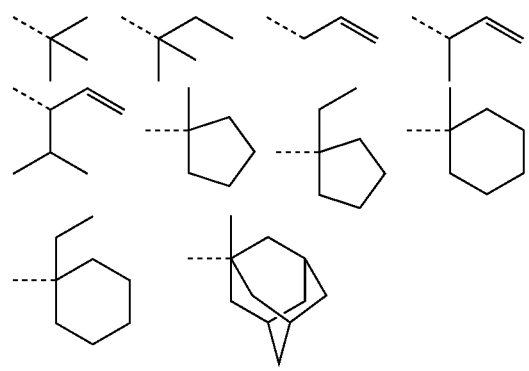

wherein the broken line denotes a valence bond.

Examples of the straight, branched or cyclic, monovalent $C_1$-$C_{10}$ hydrocarbon group represented by $R^2$ include, but are not limited to, alkyl groups such as methyl, ethyl, propyl, isopropyl, n-butyl, sec-butyl, tert-butyl, n-pentyl, tert-amyl, n-hexyl, n-octyl, n-nonyl, n-decyl, cyclopentyl, cyclohexyl, cyclopentylmethyl, cyclohexylmethyl, norbornyl, tricyclo[5.2.1.0$^{2.6}$]decanyl, 1-adamantyl, and 2-adamantyl.

Suitable $C_1$-$C_{15}$ acid labile groups represented by $R^3$ include groups A to Q, below. It is noted that in the case of k=0, the acid labile group is limited to groups A to J.

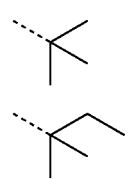

A

B

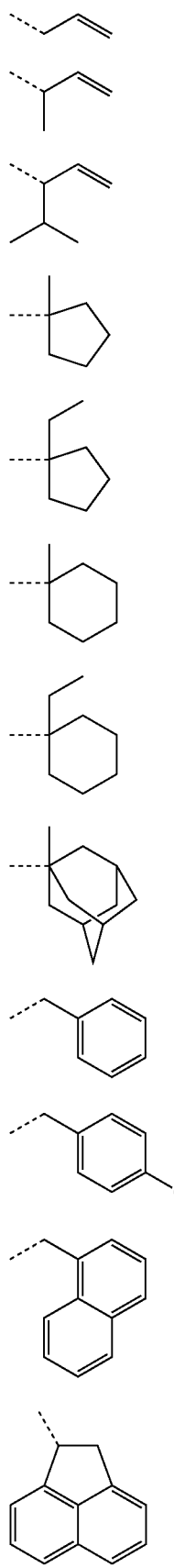

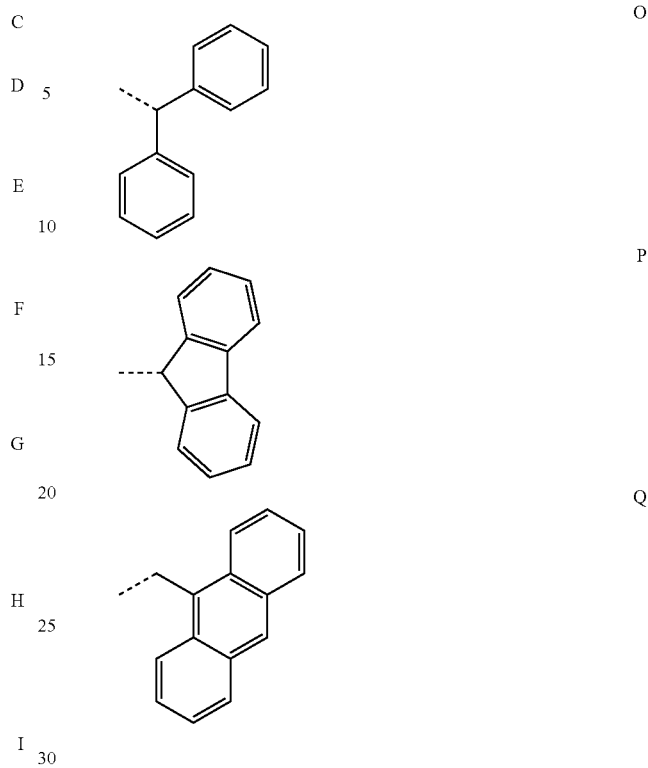

Herein the broken line denotes a valence bond.

Examples of the straight, branched or cyclic, divalent $C_1$-$C_{10}$ hydrocarbon group represented by $A^1$ are illustrated below, but not limited thereto.

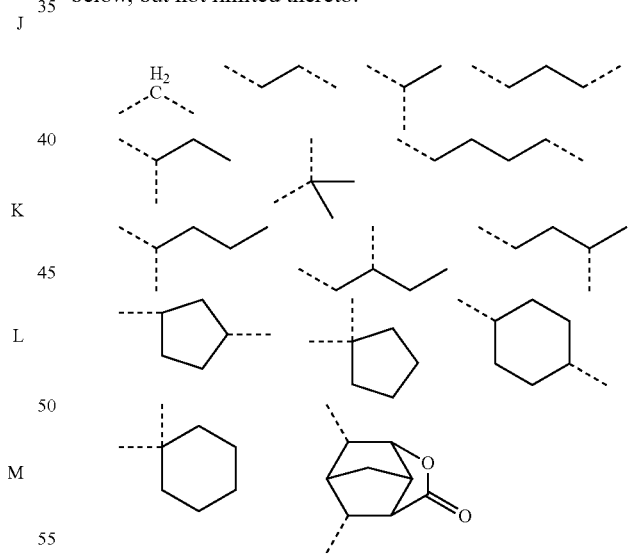

Herein the broken line denotes a valence bond.

Examples of the straight, branched or cyclic, divalent $C_1$-$C_{10}$ hydrocarbon group represented by $A^2$ are illustrated below, but not limited thereto.

-continued
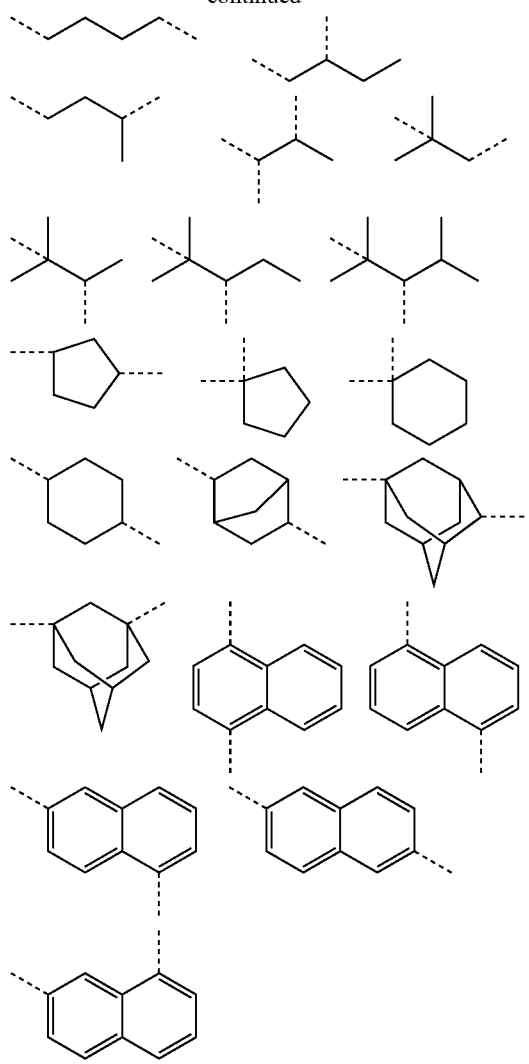
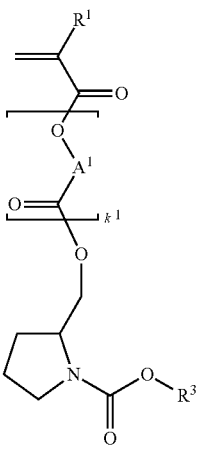
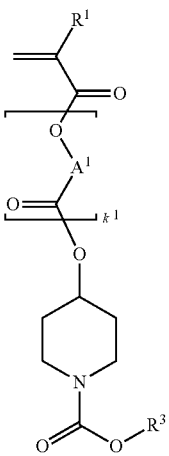
Herein the broken line denotes a valence bond.
When $A^2$ and $R^2$ bond together to form a ring with the adjacent nitrogen atom, $A^2$ is a trivalent hydrocarbon group and $R^2$ is a divalent hydrocarbon group, examples of which are illustrated below, but not limited thereto.
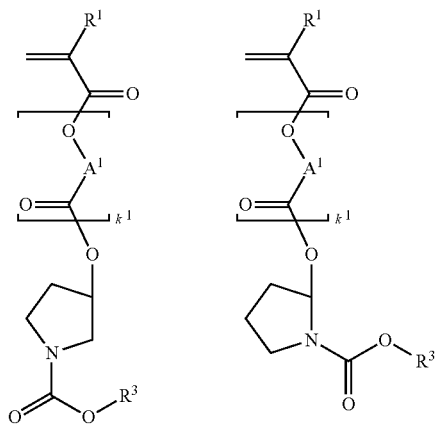
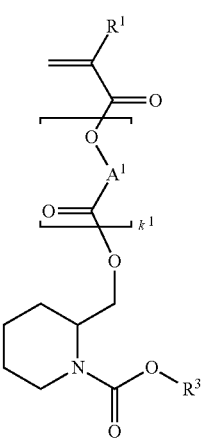
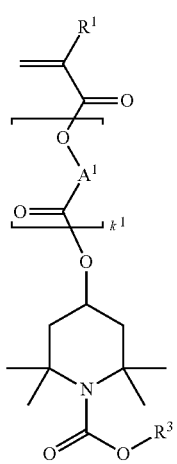

-continued

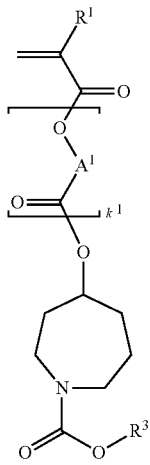
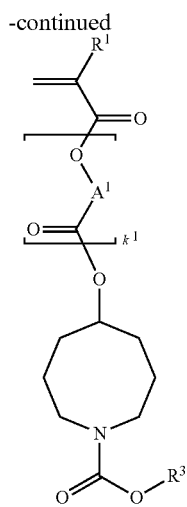

Herein $R^1$, $R^3$, $A^1$ and $k^1$ are as defined above.

The nitrogen-containing monomer of formula (1) has a carbamate structure. The carbamate undergoes deprotection reaction in the presence of an acid to generate a primary or secondary amine, whereby basicity increases, as shown by the reaction scheme below.

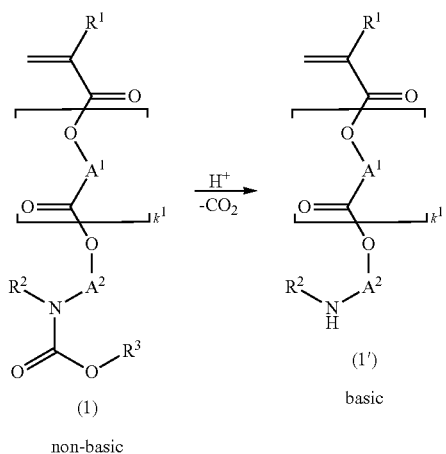

Herein $R^1$ to $R^3$, $A^1$, $A^2$, and $k^1$ are as defined above.

Specifically, the polymer comprising recurring units derived from the nitrogen-containing monomer of formula (1) undergoes deprotection reaction under the action of an acid generated in the resist film to generate an amine structure included in formula (1'). At this point, it functions as a quencher.

The nitrogen-containing monomer of formula (1) is possible to control its behavior as quencher in the resist film including deprotection reaction of carbamate and the strength of basicity of the amine moiety generated, by properly selecting the structure of acid labile group $R^3$ on the carbamate moiety, the structure of $R^2$ and $A^2$ of the nitrogen-containing moiety, and the length of a linker unit, depicted at $k^1$, between the polymerizable (meth)acrylic moiety and the nitrogen-containing moiety. It is preferred for availability of reactants and ease of preparation that the amine unit be a cyclic secondary amine unit such as pyrrolidine or piperidine. For the same reason, the acid labile group $R^3$ is preferably tert-butyl, tert-amyl, allyloxy, benzyl or the like.

Preferred examples of the nitrogen-containing monomer of formula (1) are given below, but not limited thereto.

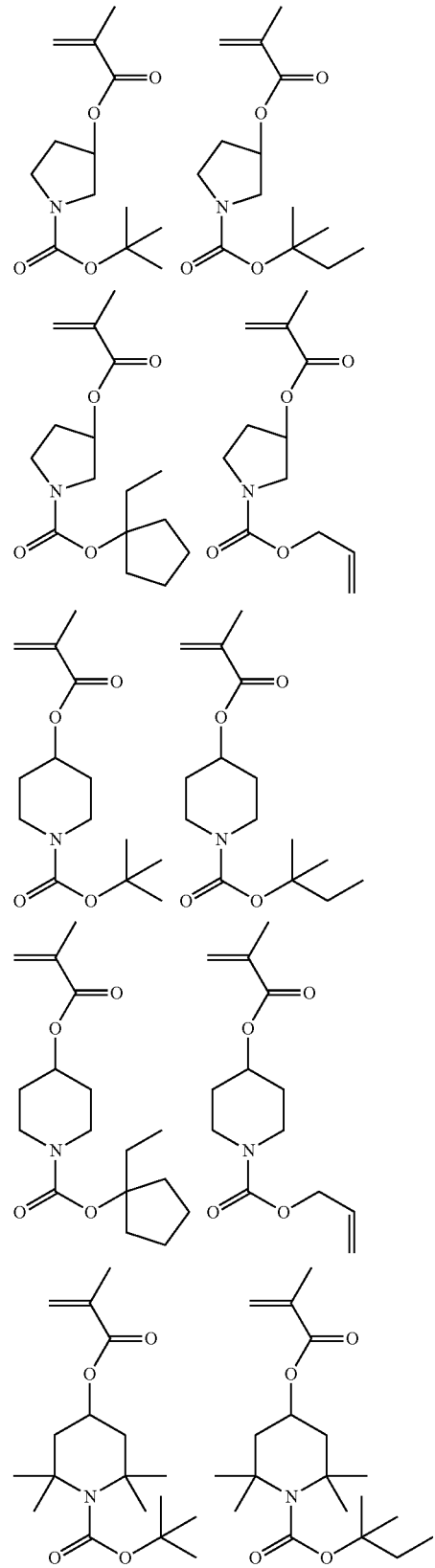

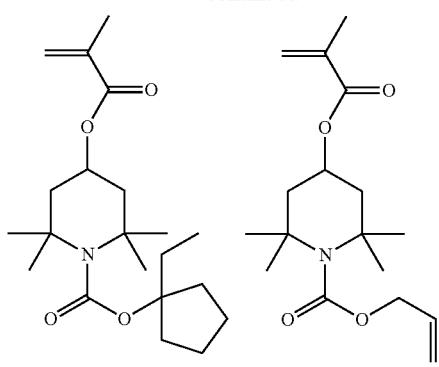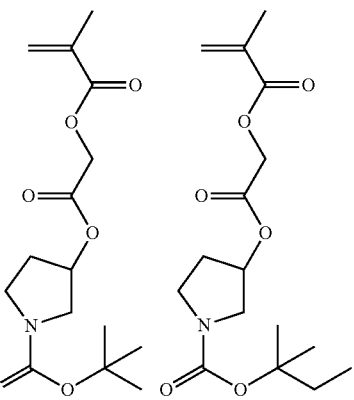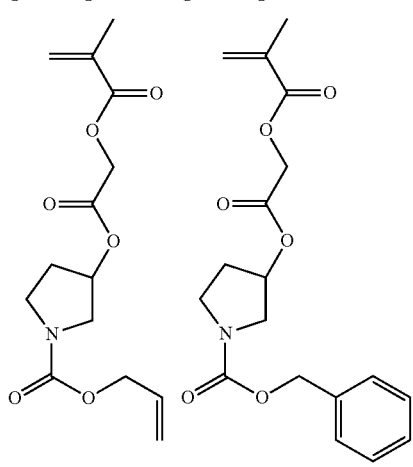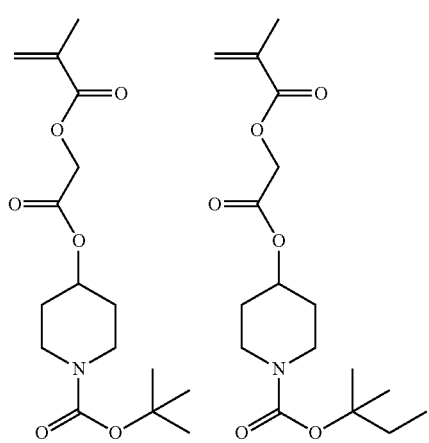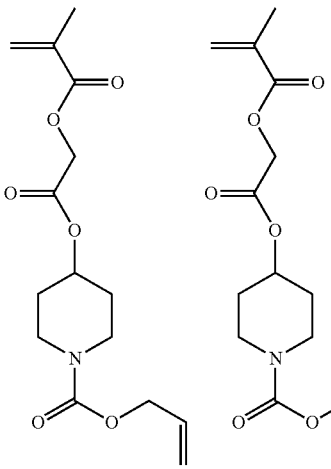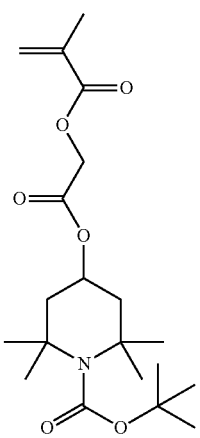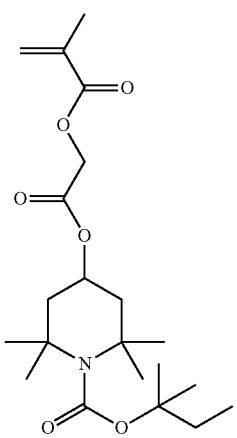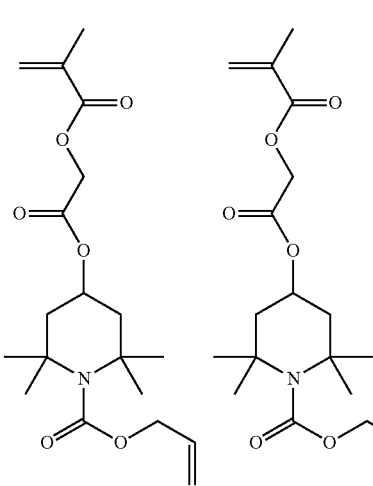

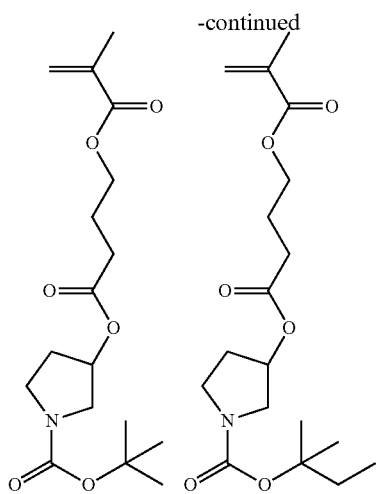
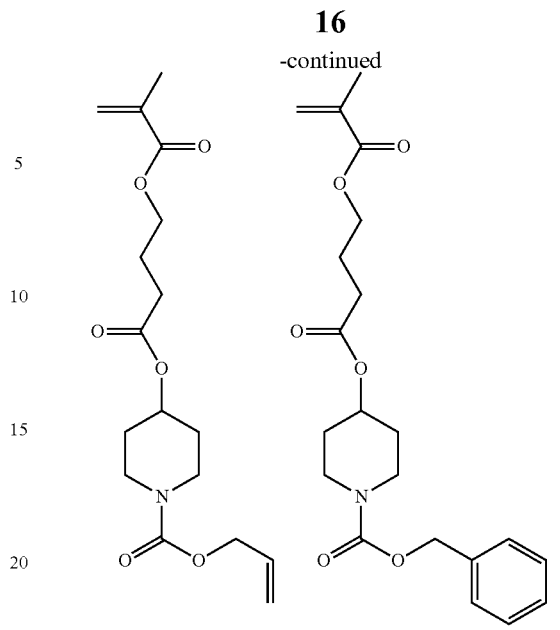
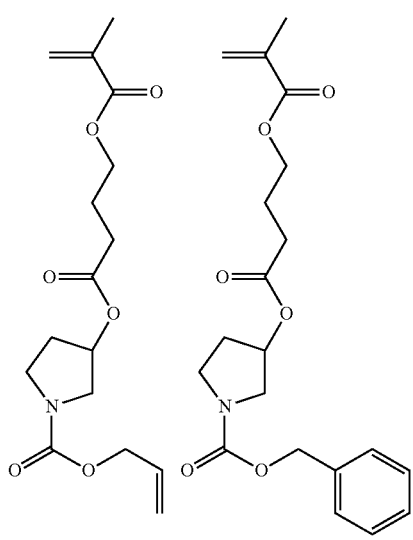
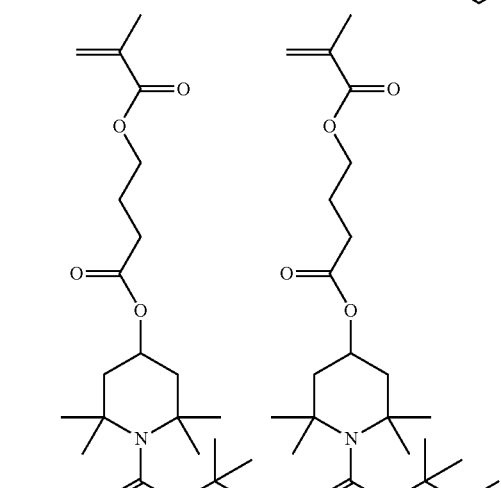
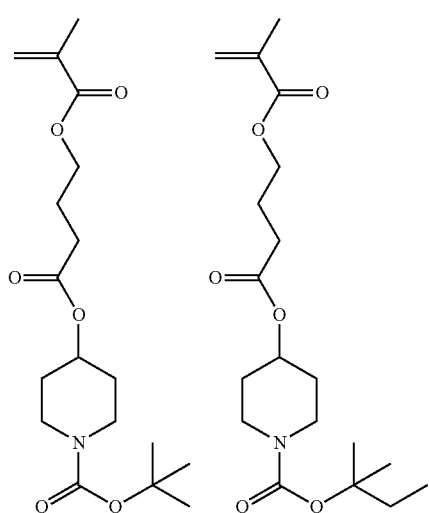
The nitrogen-containing monomer of formula (1) may be prepared, for example, by the method of the following reaction scheme although the method is not limited thereto.

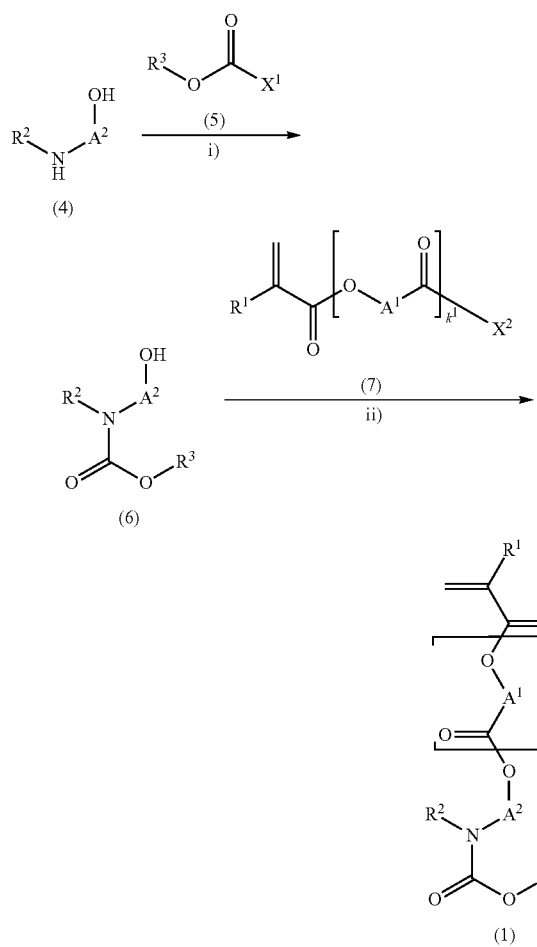

Herein $R^1$ to $R^3$, $A^1$, $A^2$, and $k^1$ are as defined above, $X^1$ is a halogen atom or $-OR^{11}$, $R^{11}$ is a group of the following formula (8):

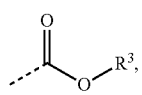

and $X^2$ is a halogen atom, hydroxyl, alkoxy or acyloxy group.

It is noted that the nitrogen-containing monomer of formula (1) wherein $k^1=1$ may be prepared by an alternative method as shown below.

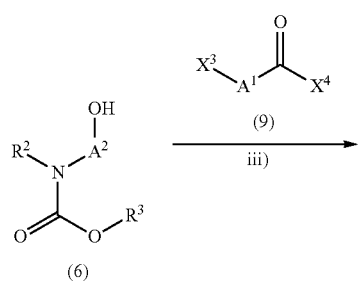

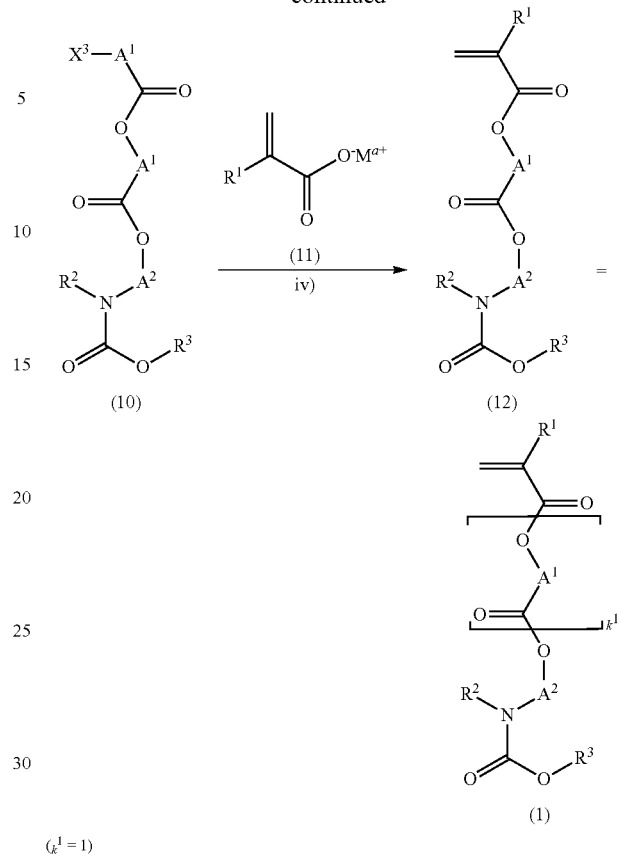

Herein $R^1$ to $R^3$, $A^1$, $A^2$, and $k^1$ are as defined above, $X^3$ is a halogen atom, $X^4$ is a halogen atom, hydroxyl, alkoxy or acyloxy group, and $M^a$ is Li, Na, K, $Mg_{1/2}$, $Ca_{1/2}$ or substituted or unsubstituted ammonium.

Step i) is a reaction of aminoalcohol (4) with alkoxycarbonylation agent (5) to form hydroxycarbamate (6).

The reaction of step i) may readily proceed in a well-known manner. Suitable alkoxycarbonylation agents (5) include dicarbonic diesters of formula (5) wherein $X^1$ is $-OR^{11}$ and halocarbonic esters of formula (5) wherein $X^1$ is halogen. In one embodiment wherein the alkoxycarbonylation agent (5) used is a dicarbonic diester such as dibenzyl dicarbonate, di-tert-butyl dicarbonate, or di-tert-amyl dicarbonate, the aminoalcohol (4), the dicarbonic diester, and a base (e.g., triethylamine, pyridine, 2,6-lutidine or N,N-dimethylaniline) may be successively or simultaneously added to a solvent (e.g., methylene chloride, acetonitrile, diethyl ether, tetrahydrofuran, N,N-dimethylformamide, toluene or hexane) while the reaction system may be cooled or heated as desired. In another embodiment wherein the alkoxycarbonylation agent (5) used is a halocarbonic ester such as allyl chlorocarbonate or benzyl chlorocarbonate, the aminoalcohol (4), the halocarbonic ester, and a base (e.g., triethylamine, pyridine, 2,6-lutidine or N,N-dimethylaniline) may be successively or simultaneously added to a solventless system or to a solvent (e.g., methylene chloride, acetonitrile, diethyl ether, tetrahydrofuran, N,N-dimethylformamide, toluene or hexane) while the reaction system may be cooled or heated as desired. Although the amount of alkoxycarbonylation agent (5) used varies with conditions, the amount in one embodiment is desirably 1.0 to 5.0 moles, more desirably 1.0 to 2.0 moles per mole of aminoalcohol (4). Although the amount of the base used varies with conditions, the amount in one embodiment is desirably 0 to 5.0 moles, more desirably 0 to 2.0 moles per mole of aminoalcohol (4). The reaction time is determined as appropriate by monitoring the reaction process by gas chromatography (GC) or silica gel thin-layer chromatography (TLC) because it is desirable from the yield aspect to drive the reaction to completion. Usually the reaction time is about 0.5 to about 24 hours. The desired hydroxycarbamate (6) may be recovered from the reaction mixture by ordinary aqueous work-up. If necessary, the compound (6) may be purified by standard techniques like distillation, chromatography and recrystallization.

Step ii) is a reaction of hydroxycarbamate (6) with esterifying agent (7) to form nitrogen-containing monomer (1).

The reaction of step ii) may readily proceed in a well-known manner. Suitable esterifying agents (7) include acid chlorides of formula (7) wherein $X^2$ is chlorine, carboxylic acids of formula (7) wherein $X^2$ is hydroxyl, and acid anhydrides of formula (7) wherein $X^2$ is acyloxy. In one embodiment wherein the esterifying agent (7) used is an acid chloride such as methacryloyl chloride, the hydroxycarbamate (6), the acid chloride, and a base (e.g., triethylamine, pyridine or 4-dimethylaminopyridine) may be successively or simultaneously added to a solventless system or to a solvent (e.g., methylene chloride, acetonitrile, toluene or hexane) while the reaction system may be cooled or heated as desired. In another embodiment wherein the esterifying agent (7) used is a carboxylic acid such as methacrylic acid, the hydroxycarbamate (6) and the carboxylic acid may be heated in a solvent (e.g., toluene or hexane) in the presence of an acid catalyst while water formed during reaction may be removed out of the system if desired. Suitable acid catalysts used herein include mineral acids such as hydrochloric acid, sulfuric acid, nitric acid and perchloric acid and organic acids such as p-toluenesulfonic acid and benzenesulfonic acid. In a further embodiment wherein the esterifying agent (7) used is an acid anhydride such as methacrylic anhydride, the hydroxycarbamate (6), the acid anhydride, and a base (e.g., triethylamine, pyridine or 4-dimethylaminopyridine) may be successively or simultaneously added to a solventless system or to a solvent (e.g., methylene chloride, acetonitrile, toluene or hexane) while the reaction system may be cooled or heated as desired. The reaction time is determined as appropriate by monitoring the reaction process by GC or silica gel TLC because it is desirable from the yield aspect to drive the reaction to completion. Usually the reaction time is about 0.5 to about 24 hours. The nitrogen-containing monomer (1) may be recovered from the reaction mixture by ordinary aqueous work-up. If necessary, the monomer (1) may be purified by standard techniques like distillation, chromatography and recrystallization.

Step iii) is a reaction of hydroxycarbamate (6) with esterifying agent (9) to form halo-ester (10).

The reaction of step iii) may readily proceed in a well-known manner. Suitable esterifying agents (9) include acid chlorides of formula (9) wherein $X^4$ is chlorine and carboxylic acids of formula (9) wherein $X^4$ is hydroxyl. In one embodiment wherein the esterifying agent (7) used is an acid chloride such as 2-chloroacetic acid chloride or 3-chloropropionic acid chloride, the hydroxycarbamate (6), the acid chloride, and a base (e.g., triethylamine, pyridine or 4-dimethylaminopyridine) may be successively or simultaneously added to a solventless system or to a solvent (e.g., methylene chloride, acetonitrile, toluene or hexane) while the reaction system may be cooled or heated as desired. In another embodiment wherein the esterifying agent (7) used is a carboxylic acid such as 2-chloroacetic acid or 3-chloropropionic acid, the hydroxycarbamate (6) and the carboxylic acid may be heated in a solvent (e.g., toluene or hexane) in the presence of an acid catalyst while water formed during reaction may be removed out of the system if desired. Suitable acid catalysts used herein include mineral acids such as hydrochloric acid, sulfuric acid, nitric acid and perchloric acid and organic acids such as p-toluenesulfonic acid and benzenesulfonic acid. The reaction time is determined as appropriate by monitoring the reaction process by GC or silica gel TLC because it is desirable from the yield aspect to drive the reaction to completion. Usually the reaction time is about 0.5 to about 24 hours. The desired halo-ester (10) may be recovered from the reaction mixture by ordinary aqueous work-up. If necessary, the halo-ester (10) may be purified by standard techniques like distillation, chromatography and recrystallization.

Step iv) is a reaction of halo-ester (10) with carboxylic acid salt (11) to form monomer (12), that is, nitrogen-containing monomer (1) wherein $k^1=1$.

The reaction of step iv) may be carried out by a standard method. The carboxylic acid salt (11) may be any of commercially available carboxylic acid salts such as metal salts of various carboxylic acids as purchased. Alternatively, the carboxylic acid salt may be prepared in situ from a corresponding carboxylic acid (e.g., methacrylic acid or acrylic acid) and a base. The amount of carboxylic acid salt (11) used is preferably 0.5 to 10 moles, more preferably 1.0 to 3.0 moles per mole of halo-ester (10). With less than 0.5 mole of carboxylic acid salt (11), a large fraction of the reactant may be left unreacted, leading to a substantial drop of yield. More than 10 moles of carboxylic acid salt (11) is uneconomical due to increased material costs and reduced pot yields. In the other embodiment where a carboxylic acid salt is formed within the reaction system from a corresponding carboxylic acid and a base, examples of the base used herein include amines such as ammonia, triethylamine, pyridine, lutidine, collidine, and N,N-dimethylaniline; hydroxides such as sodium hydroxide, potassium hydroxide, and tetramethylammonium hydroxide; carbonates such as potassium carbonate and sodium hydrogen carbonate; metals such as sodium; metal hydrides such as sodium hydride; metal alkoxides such as sodium methoxide and potassium tert-butoxide; organometallics such as butyl lithium and ethyl magnesium bromide; and metal amides such as lithium diisopropylamide. One or more bases may be selected from these examples. The amount of the base used is preferably 0.2 to 10 moles, and more preferably 0.5 to 2.0 moles per mole of the corresponding carboxylic acid. If the amount of the base is less than 0.2 mole, a large fraction of the carboxylic acid may become a waste, which is uneconomical. More than 10 moles of the base may lead to a substantial drop of yield due to increased side reactions. The reaction time is determined as appropriate by monitoring the reaction process by GC or silica gel TLC because it is desirable from the yield aspect to drive the reaction to completion. Usually the reaction time is about 0.5 to about 24 hours. The desired monomer (12) may be recovered from the reaction mixture by ordinary aqueous work-up. If necessary, the monomer (12) may be purified by standard techniques like distillation, chromatography and recrystallization.

Polymer

Another embodiment of the invention is a polymer comprising recurring units (a) having the general formula (2). For convenience of description, the polymer comprising recurring units (a) having formula (2) is referred to as polymer P1.

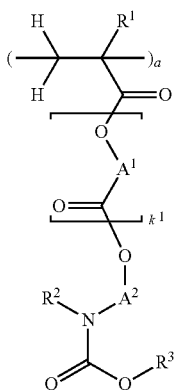
(2)

Herein $R^1$ to $R^3$, $A^1$, $A^2$, and $k^1$ are as defined above, and "a" is a number in the range: $0<a<1.0$.

Polymer P1 contains a carbamate structure in the recurring unit of formula (2). When used in a resist composition, polymer P1 can function as a quencher by the above-described mechanism. Polymer P1 is so designed as to generate an amine quencher within the recurring unit to exert a quencher function. This restrains the volatilization of quencher component. Thus polymer P1 is expected to form a pattern of high resolution and satisfactory profile, free of defects by chemical flare.

In a preferred embodiment, polymer P1 may further comprise recurring units having an acid labile group capable of generating a carboxyl and/or hydroxyl group under the action of an acid, copolymerized with recurring units (a) having formula (2). Differently stated, polymer P1 may further comprise at least one of recurring units (b) and (c) having an acid labile group-substituted carboxyl and/or hydroxyl group, as represented by the general formula (3).

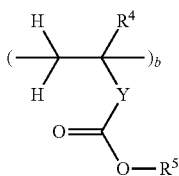 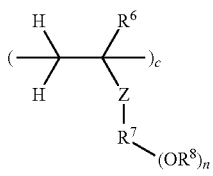
(3)

Herein $R^4$ and $R^6$ each are hydrogen or methyl; $R^5$ and $R^8$ each are an acid labile group; $R^7$ is a straight, branched or cyclic $C_1$-$C_{10}$ alkylene group or a trivalent form of the alkylene group with one hydrogen eliminated, which may contain an ether or ester moiety, or a phenylene or naphthylene group; Y is a single bond or —C(=O)—O—$R^9$—; $R^9$ is a straight, branched or cyclic $C_1$-$C_{10}$ alkylene group which may contain an ether or ester moiety, or a phenylene or naphthylene group; Z is a single bond or —C(=O)—O—$R^{10}$—; $R^{10}$ is a straight, branched or cyclic $C_1$-$C_{10}$ alkylene group which may contain an ether or ester moiety, or a phenylene or naphthylene group; the phenylene and naphthylene groups may be substituted with fluorine, trifluoromethyl, cyano, amide or $C_1$-$C_6$ alkyl or alkoxy radical; n is 1 or 2, b and c are numbers in the range: $0 \le b < 1.0$, $0 \le c < 1.0$, and $0 < b+c < 1$.

Formula (3) represents acid labile units containing $R^5$ and $R^8$ which are described below. The acid labile unit is a recurring unit having a structure in which an acidic group such as a carboxylic acid, phenol or fluoroalcohol is protected with an acid labile group and which is deprotected with an acid so that the polymer may become more soluble in an alkaline developer. Of the recurring units represented by formula (3), unit (b) is a structure having a carboxylic acid protected with an acid labile group $R^5$. The acid labile group $R^5$ may be selected from a variety of such groups, for example, alkoxymethyl groups of formula (L1) and tertiary alkyl groups of formulae (L2) to (L8), but not limited thereto. Of these, groups of formulae (L2) to (L5) are preferred. Unit (c) has an acid labile group $R^8$ which is preferably selected from formulae (L1) and (L2).

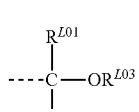
(L1)

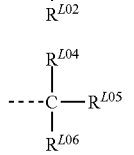
(L2)

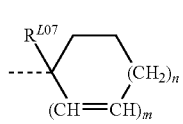
(L3)

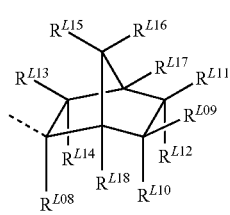
(L4)

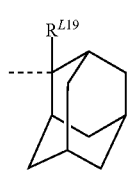
(L5)

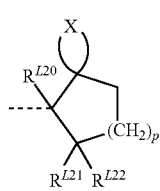
(L6)

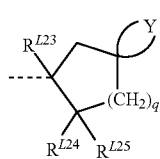
(L7)

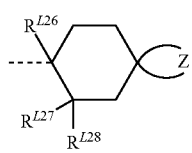
(L8)

Herein the broken line denotes a valence bond.

In formula (L1), $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, and adamantyl. $R^{L03}$ is a monovalent hydrocarbon group of 1 to 18 carbon atoms, preferably 1 to 10 carbon atoms, which may contain a heteroatom such as oxygen, examples of which include straight, branched or cyclic alkyl groups and substituted forms of such alkyl groups in which some hydrogen atoms are replaced by hydroxyl, alkoxy, oxo, amino, alkylamino or the like. Examples of suitable straight, branched or cyclic alkyl groups are as illustrated for $R^{L01}$ and $R^{L02}$. Examples of the substituted alkyl groups are shown below.

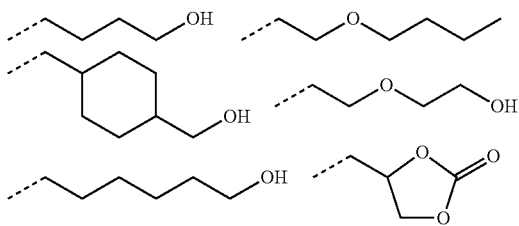

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$, $R^{L05}$ and $R^{L06}$ are each independently a straight, branched or cyclic $C_1$-$C_{15}$ alkyl group. Examples include methyl, ethyl, propyl, isopropyl, n-butyl, sec-butyl, tert-butyl, cyclopentyl, cyclohexyl, 2-ethylhexyl, n-octyl, 1-adamantyl and 2-adamantyl.

In formula (L3), $R^{L07}$ is an optionally substituted straight, branched or cyclic $C_1$-$C_{10}$ alkyl group or an optionally substituted $C_6$-$C_{20}$ aryl group. Examples of the optionally substituted alkyl group include straight, branched or cyclic alkyl groups such as methyl, ethyl, propyl, isopropyl, n-butyl, sec-butyl, tert-butyl, tert-amyl, n-pentyl, n-hexyl, cyclopentyl, cyclohexyl, and bicyclo[2.2.1]heptyl, and substituted forms of these alkyl groups in which one or more hydrogen is replaced by hydroxyl, alkoxy, carboxyl, alkoxycarbonyl, oxo, amino, alkylamino, cyano, mercapto, alkylthio, sulfo or the like or in which one or more methylene moiety is replaced by oxygen or sulfur atom. Examples of the optionally substituted aryl group include phenyl, methylphenyl, naphthyl, anthryl, phenanthryl, and pyrenyl. The subscript m is 0 or 1, n is 0, 1, 2 or 3, and 2m+n is equal to 2 or 3.

In formula (L4), $R^{L08}$ is an optionally substituted straight, branched or cyclic $C_1$-$C_{10}$ alkyl group or an optionally substituted $C_6$-$C_{20}$ aryl group. Examples are as exemplified above for $R^{L07}$. $R^{L09}$ to $R^{L18}$ are each independently hydrogen or a $C_1$-$C_{15}$ monovalent hydrocarbon group. Examples include straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, and cyclohexylbutyl, and substituted forms of these alkyl groups in which one or more hydrogen is replaced by hydroxyl, alkoxy, carboxyl, alkoxycarbonyl, oxo, amino, alkylamino, cyano, mercapto, alkylthio, sulfo or the like. A pair of $R^{L09}$ and $R^{L10}$, $R^{L09}$ and $R^{L11}$, $R^{L09}$ and $R^{L12}$, $R^{L10}$ and $R^{L12}$, $R^{L11}$ and $R^{L12}$, $R^{L13}$ and $R^{L14}$, $R^{L15}$ and $R^{L16}$ or $R^{L16}$ and $R^{L17}$ may bond together to form a ring. In this event, each of ring-forming R's is a $C_1$-$C_{15}$ divalent hydrocarbon group, examples of which correspond to the above-exemplified monovalent hydrocarbon groups with one hydrogen being eliminated. Also, a pair of $R^{L09}$ and $R^{L11}$, $R^{L11}$ and $R^{L17}$, or $R^{L15}$ and $R^{L17}$ which are attached to vicinal carbon atoms may bond together directly to form a double bond.

In formula (L5), $R^{L19}$ is an optionally substituted straight, branched or cyclic $C_1$-$C_{10}$ alkyl group or an optionally substituted $C_6$-$C_{20}$ aryl group. Examples are as exemplified above for $R^{L07}$.

In formula (L6), $R^{L20}$ is an optionally substituted straight, branched or cyclic $C_1$-$C_{10}$ alkyl group or an optionally substituted $C_6$-$C_{20}$ aryl group. Examples are as exemplified above for $R^{L07}$. X is a divalent group which forms a substituted or unsubstituted cyclopentane, cyclohexane or norbornane ring with the carbon atom to which it is attached. $R^{L21}$ and $R^{L22}$ are each independently hydrogen or a straight, branched or cyclic, monovalent hydrocarbon group of 1 to 10 carbon atoms. $R^{L21}$ and $R^{L22}$ may bond together to form a ring with the carbon atom to which they are attached, and in this event, each stands for a divalent group forming a substituted or unsubstituted cyclopentane or cyclohexane ring. The subscript p is 1 or 2.

In formula (L7), $R^{L23}$ is an optionally substituted straight, branched or cyclic $C_1$-$C_{10}$ alkyl group or an optionally substituted $C_6$-$C_{20}$ aryl group. Examples are as exemplified above for $R^{L07}$. Y is a divalent group which forms a substituted or unsubstituted cyclopentane, cyclohexane or norbornane ring with the carbon atom to which it is attached. $R^{L24}$ and $R^{L25}$ are each independently hydrogen or a straight, branched or cyclic, monovalent hydrocarbon group of 1 to 10 carbon atoms. $R^{L24}$ and $R^{L25}$ may bond together to form a ring with the carbon atom to which they are attached, and in this event, each stands for a divalent group forming a substituted or unsubstituted cyclopentane or cyclohexane ring. The subscript q is 1 or 2.

In formula (L8), $R^{L26}$ is an optionally substituted straight, branched or cyclic $C_1$-$C_{10}$ alkyl group or an optionally substituted $C_6$-$C_{20}$ aryl group. Examples are as exemplified above for $R^{L07}$. Z is a divalent group which forms a substituted or unsubstituted cyclopentane, cyclohexane or norbornane ring with the carbon atom to which it is attached. $R^{L27}$ and $R^{L28}$ are each independently hydrogen or a straight, branched or cyclic, monovalent hydrocarbon group of 1 to 10 carbon atoms. $R^{L27}$ and $R^{L28}$ may bond together to form a ring with the carbon atom to which they are attached, and in this event, each stands for a divalent group forming a substituted or unsubstituted cyclopentane or cyclohexane ring.

Of the acid labile groups of formula (L1), the straight and branched ones are exemplified by the following groups.

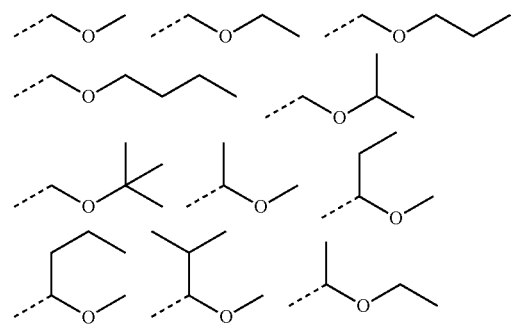

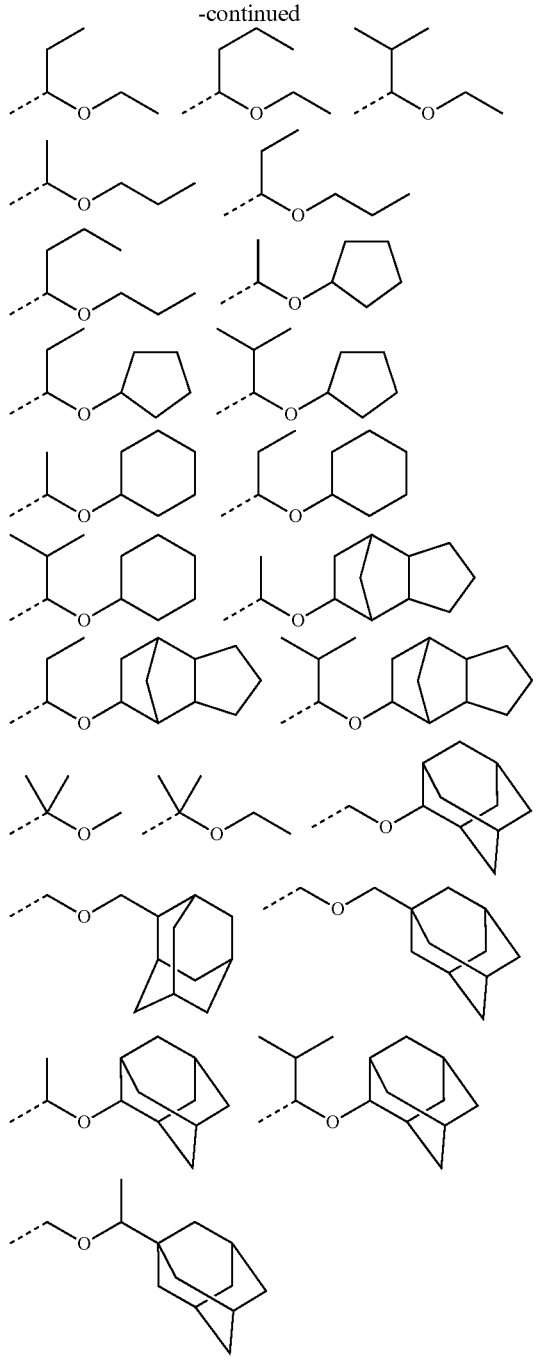

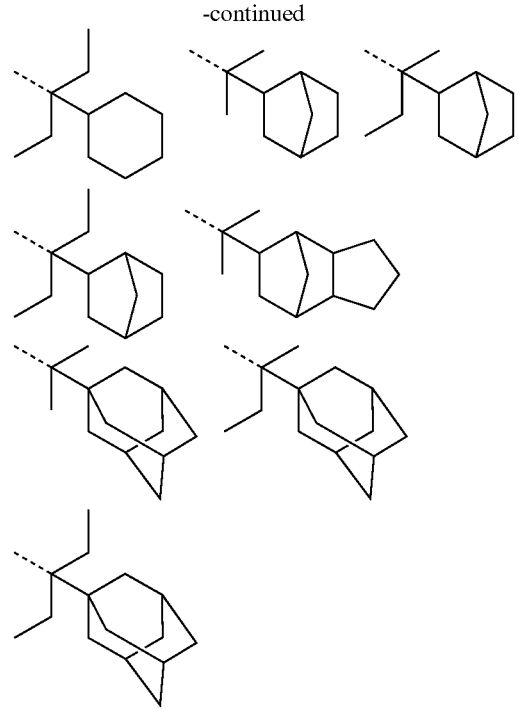

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile group of formula (L2) include tert-butyl, tert-amyl, and the groups shown below.

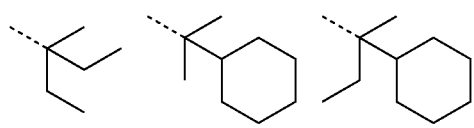

Examples of the acid labile group of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-(bicyclo[2.2.1]heptan-2-yl)cyclopentyl, 1-(7-oxabicyclo[2.2.1]heptan-2-yl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are preferred.

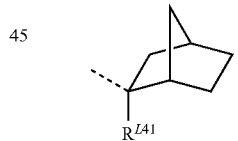
(L4-1)

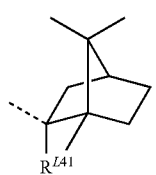
(L4-2)

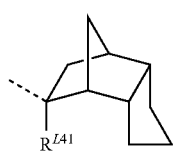
(L4-3)

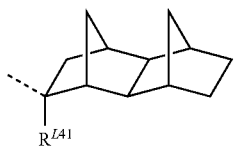
(L4-4)

Herein $R^{L41}$ is as defined above.

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

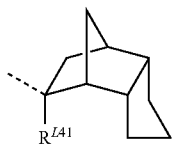
(L4-3-1)

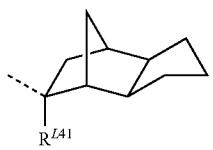
(L4-3-2)

Note that $R^{L41}$ is as defined above.

Similarly, the general formula (L4-4) represents one or a mixture of two or more selected from groups having the following general formulas (L4-4-1) to (L4-4-4).

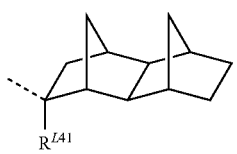
(L4-4-1)

(L4-4-2)

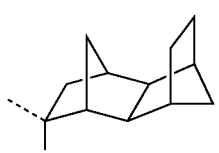
(L4-4-3)

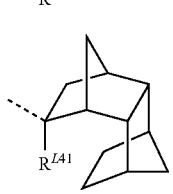
(L4-4-4)

Note that $R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo [2.2.1]heptane structure as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

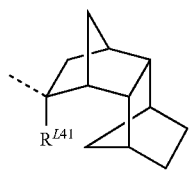
(L4-1-endo)

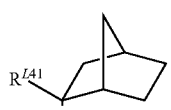
(L4-2-endo)

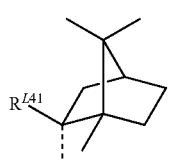
(L4-3-endo)

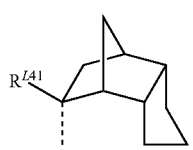
(L4-4-endo)

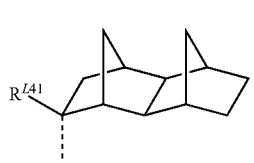

Note that $R^{L41}$ is as defined above.

Illustrative examples of the acid labile group of formula (L4) are given below.

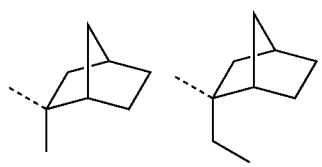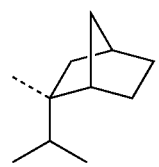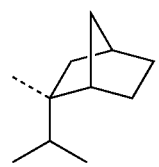

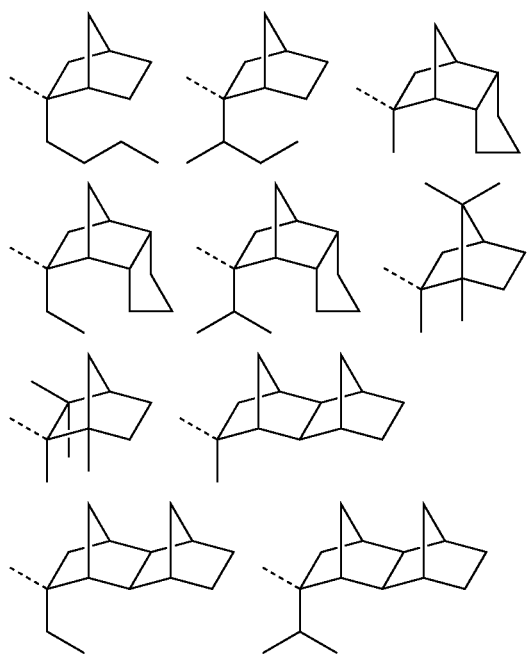
Illustrative examples of the acid labile group of formula (L5) are given below.
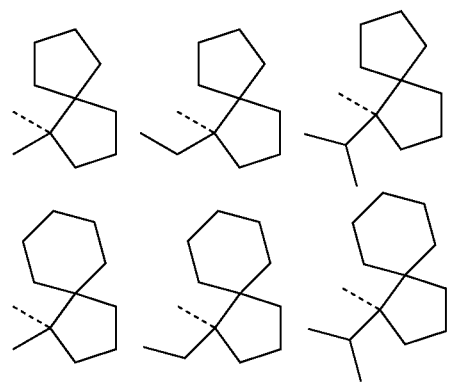
Illustrative examples of the acid labile group of formula (L6) are given below.
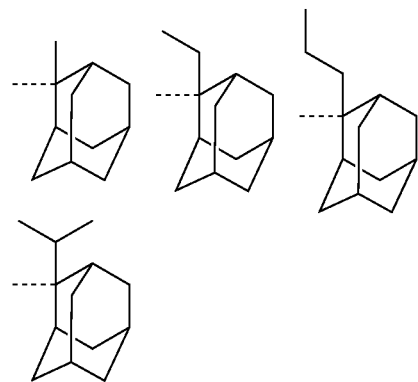
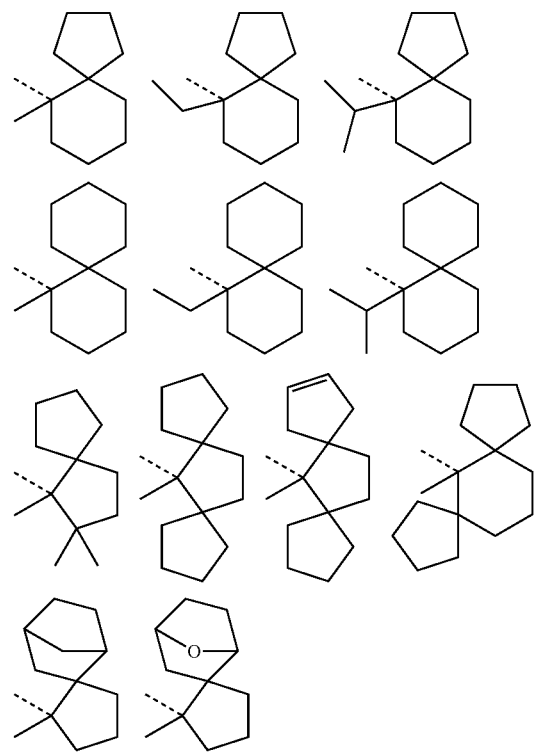
Illustrative examples of the acid labile group of formula (L7) are given below.
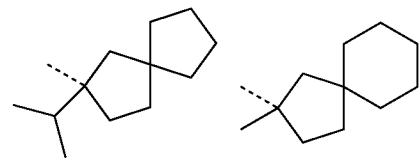
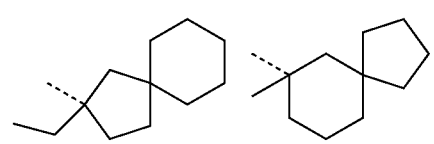
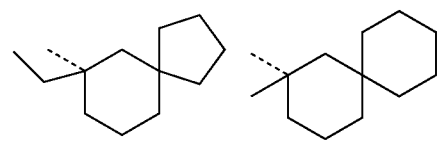
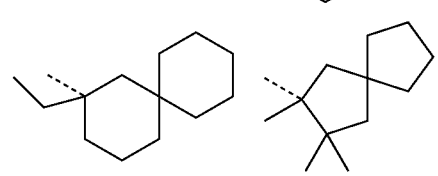

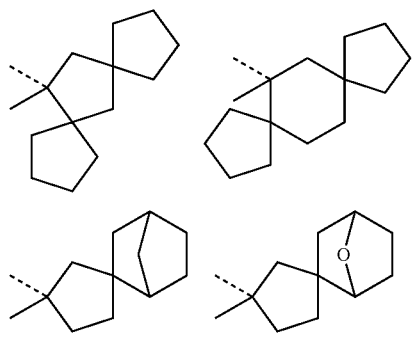
Illustrative examples of the acid labile group of formula (L8) are given below.
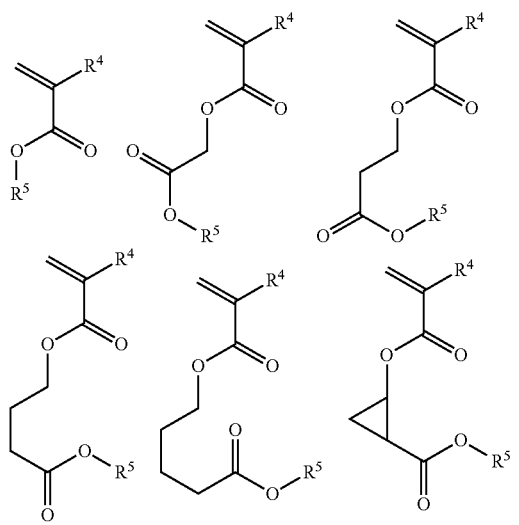
Examples of suitable monomers from which recurring units (b) are derived are given below.
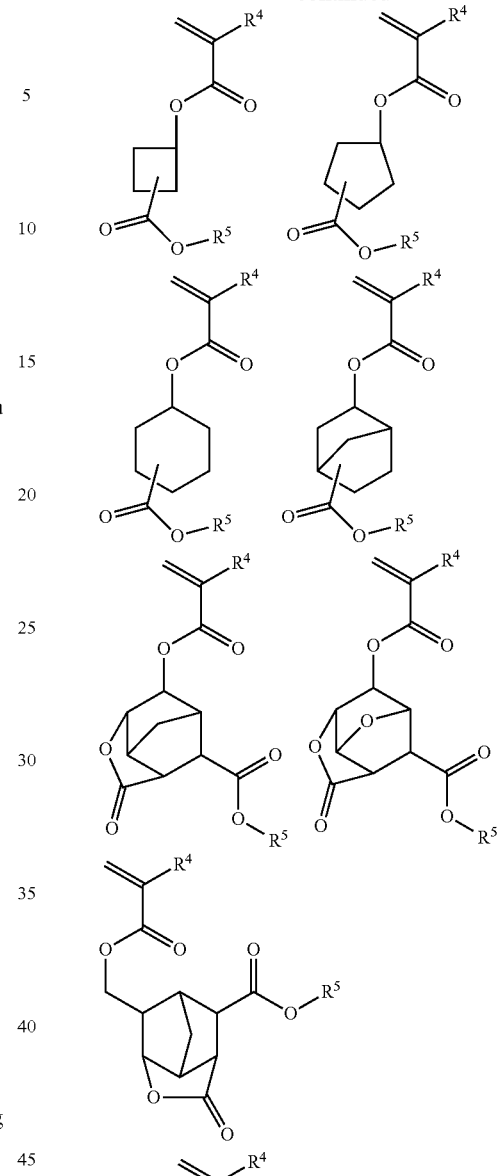

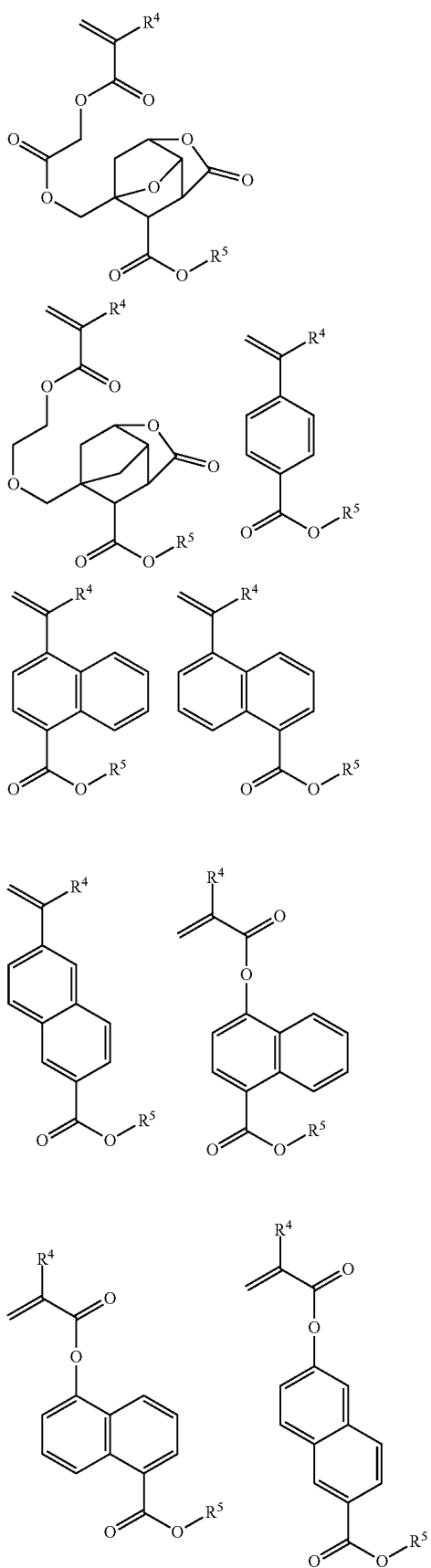
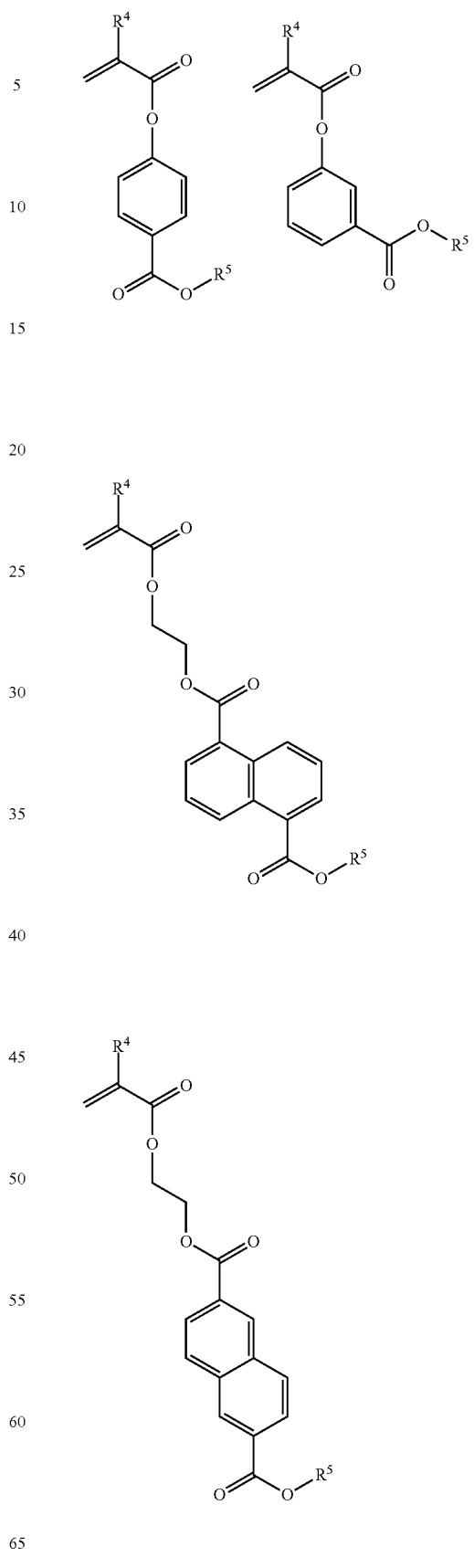

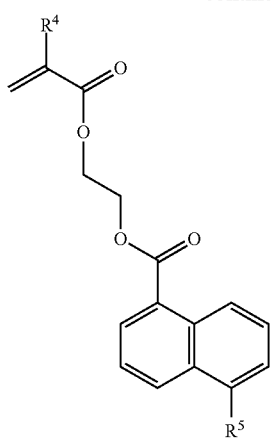
Herein R⁴ and R⁵ are as defined above.
Examples of suitable monomers from which recurring units (c) are derived are given below.
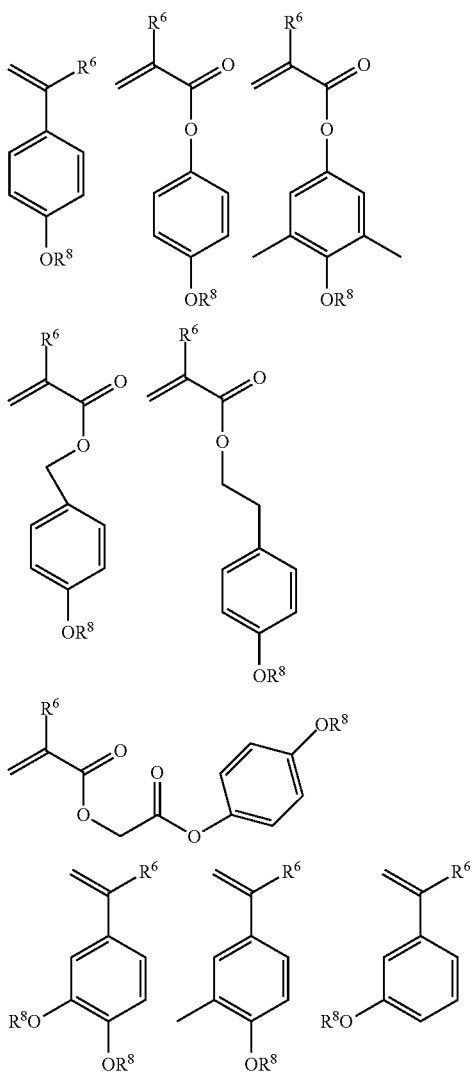
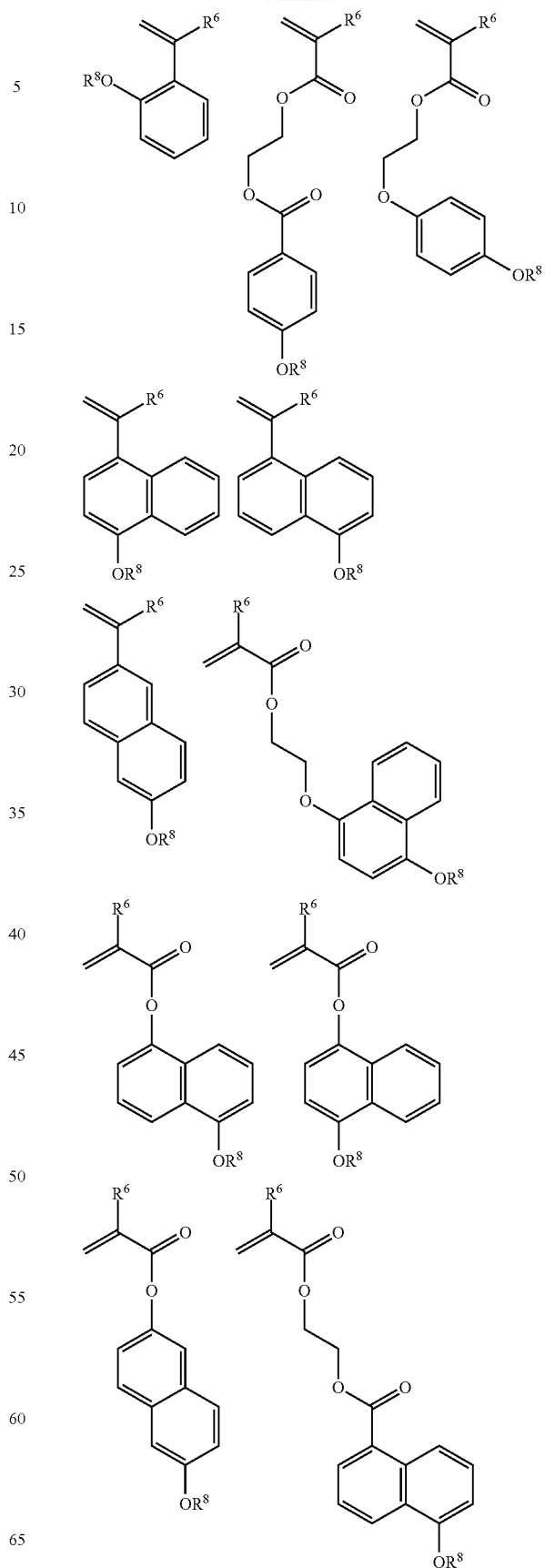

-continued
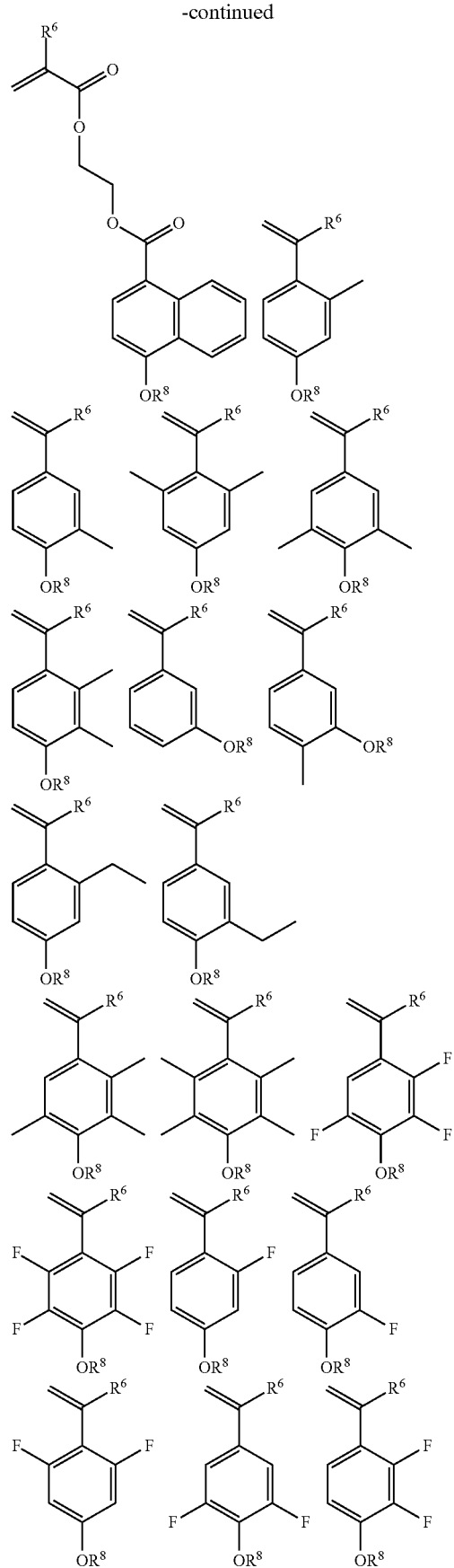
-continued
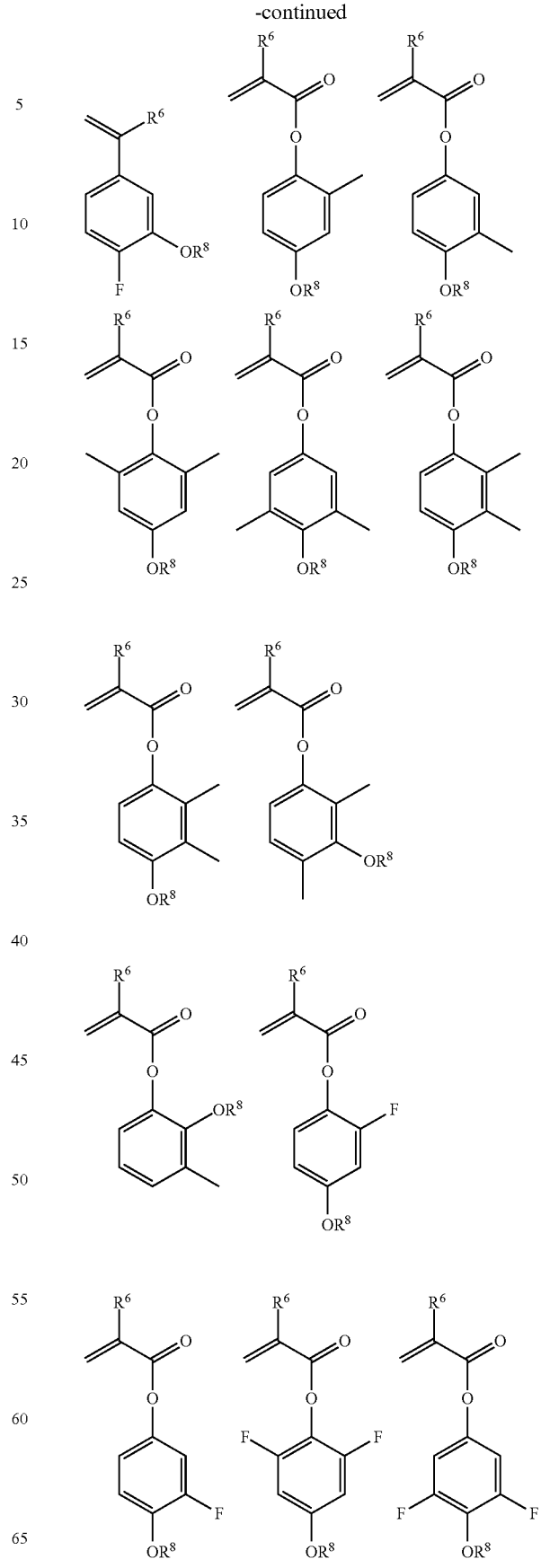

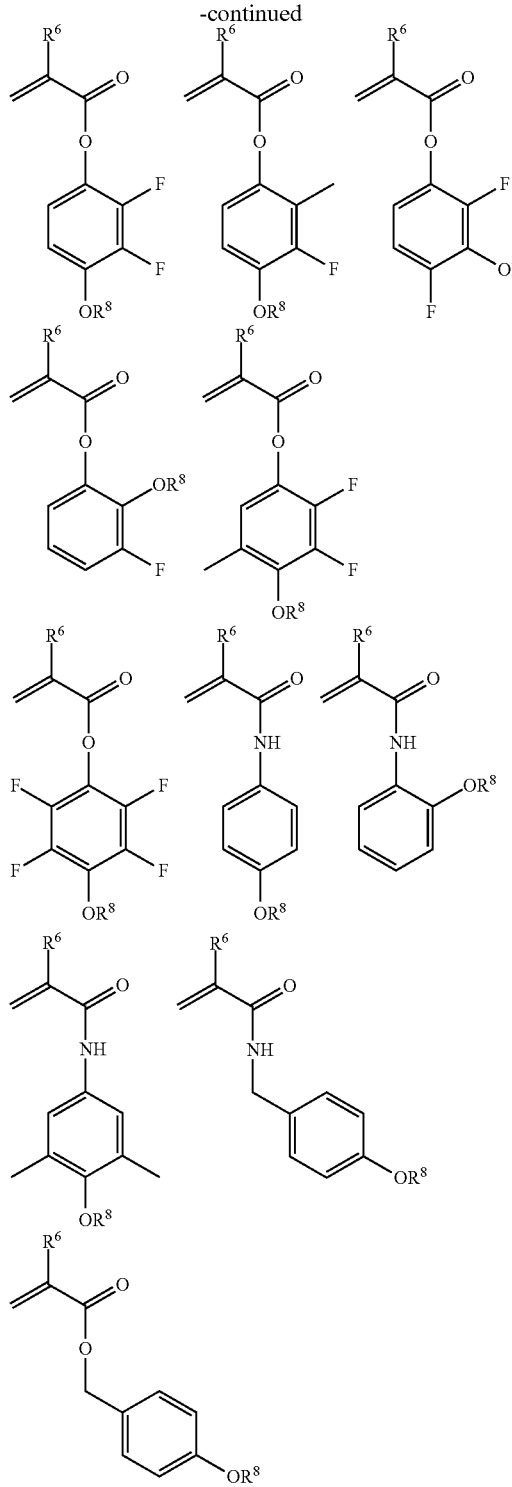

Herein $R^6$ and $R^8$ are as defined above.

In addition to the recurring units (a), (b) and (c), recurring units (d) having an adhesive group may be copolymerized in polymer P1. The adhesive group is selected from among hydroxyl, carboxyl, lactone ring, carbonate, thiocarbonate, carbonyl, cyclic acetal, ether, ester, sulfonic acid ester, cyano, amide, and —O—C(=O)-G- wherein G is sulfur or NH. Examples of suitable recurring units (d) having an adhesive group are given below.

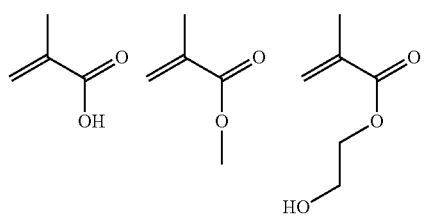
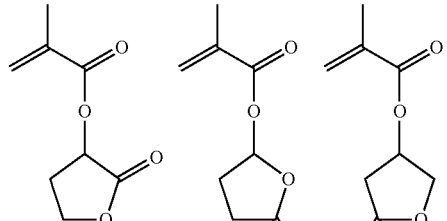
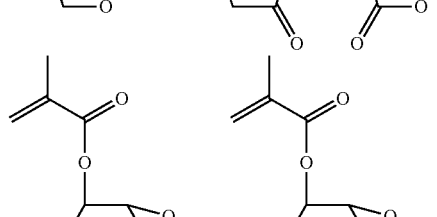
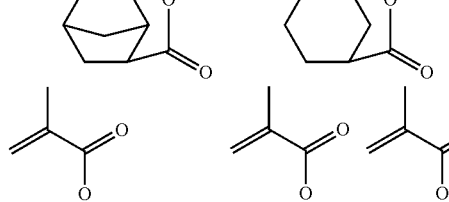
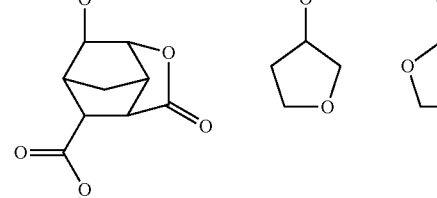
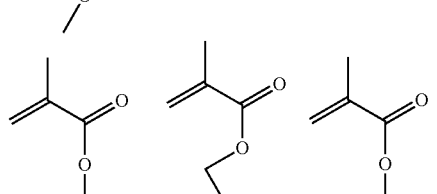
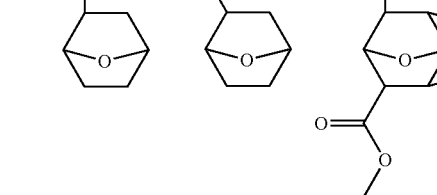

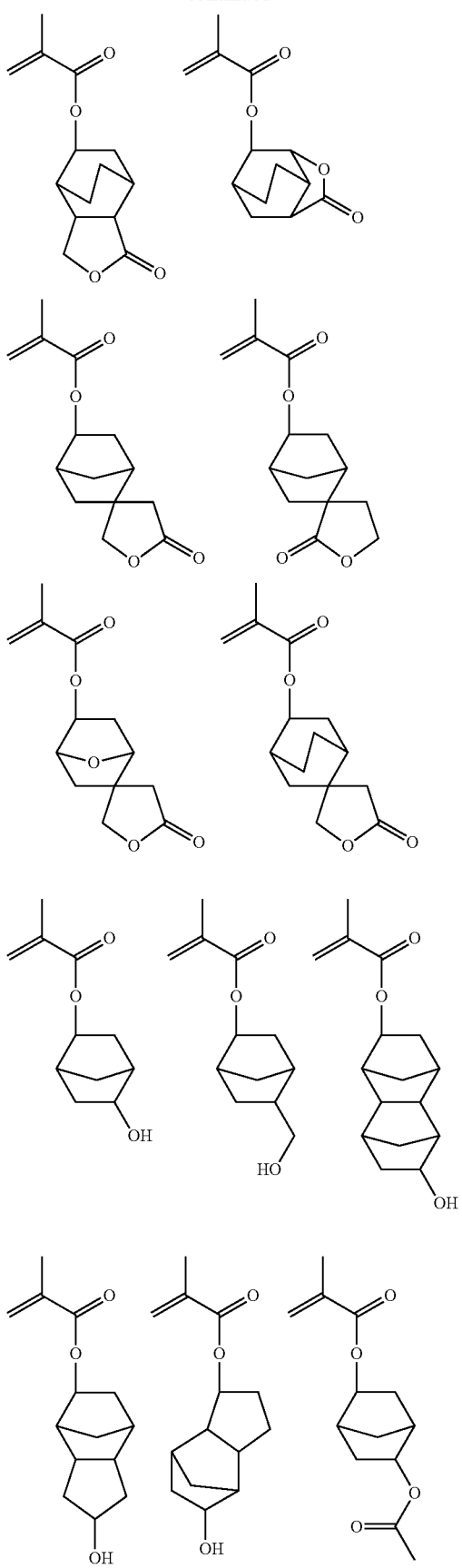
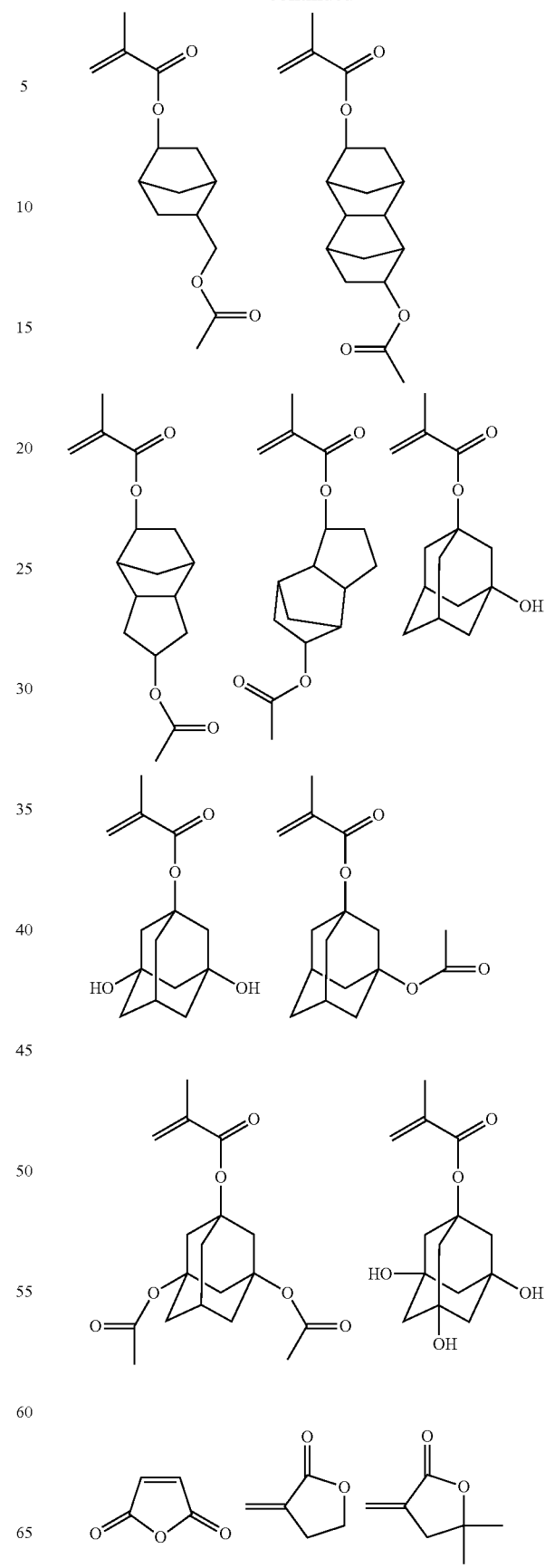

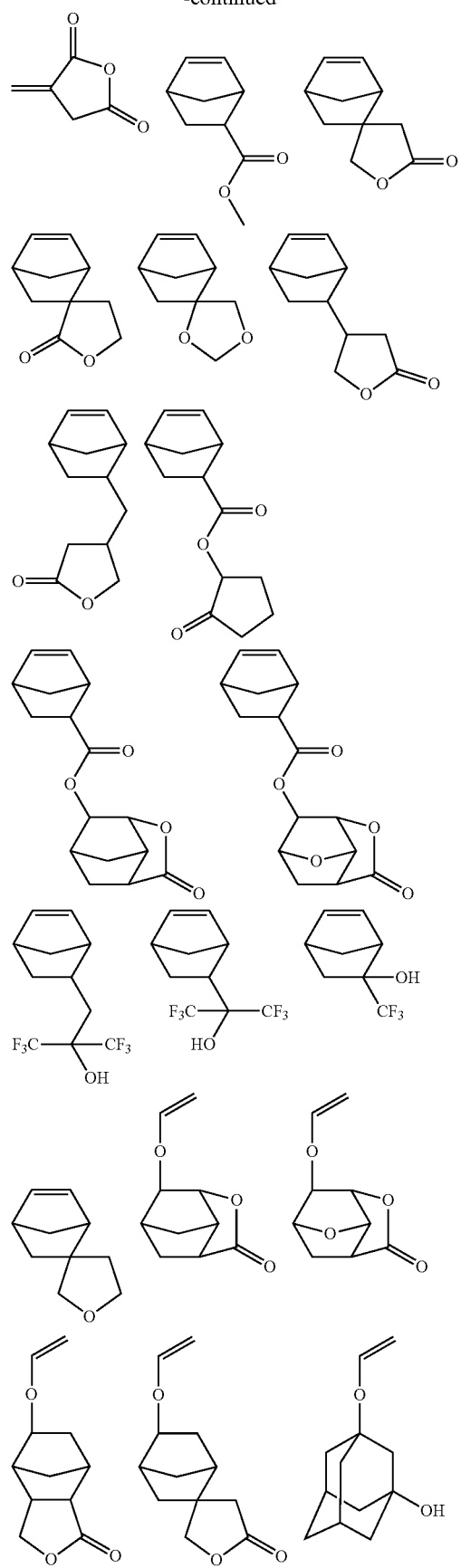
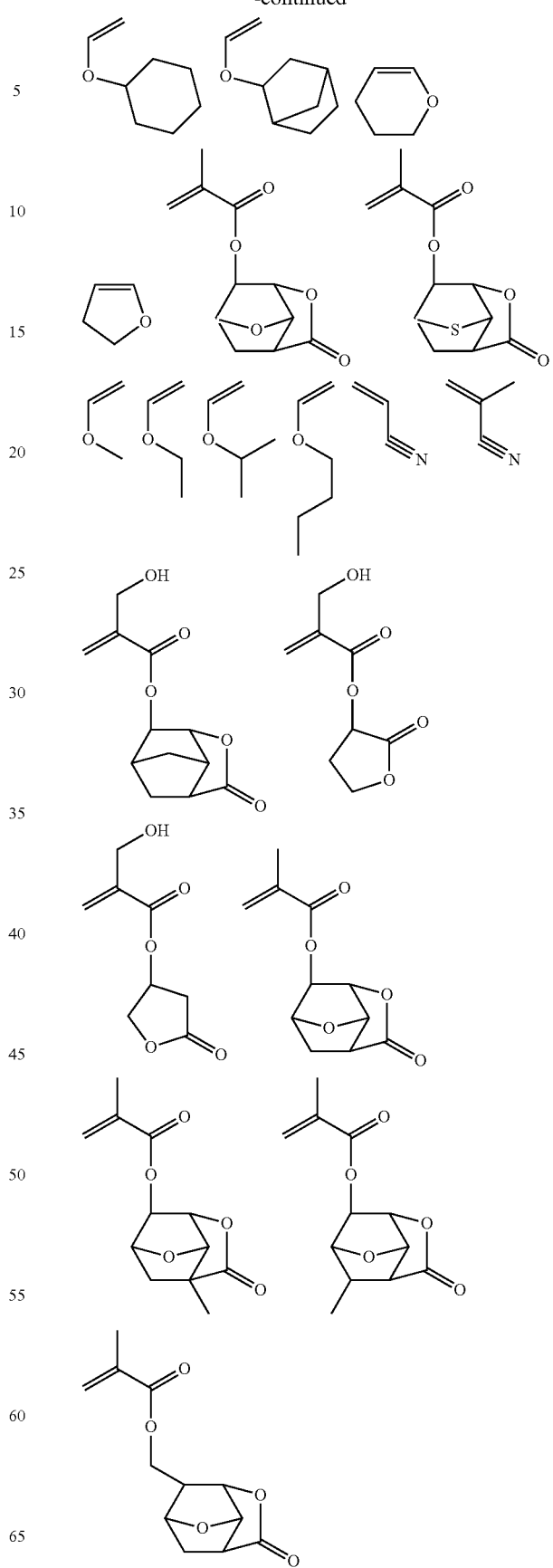

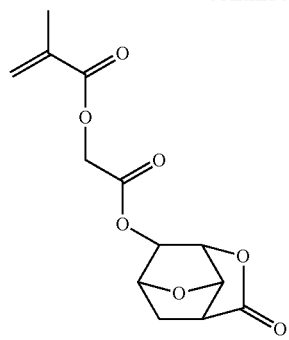
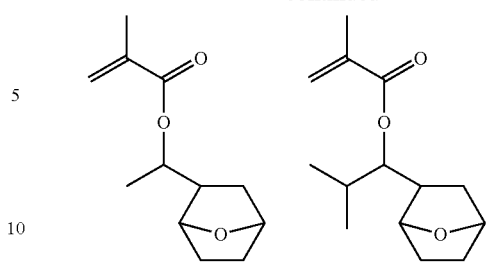
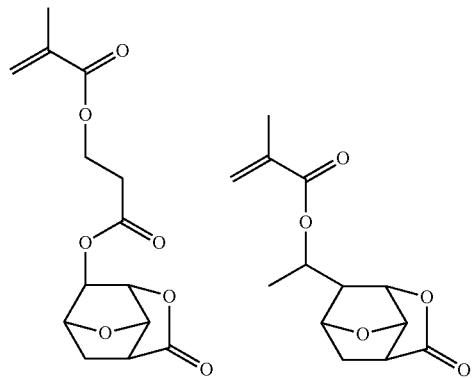
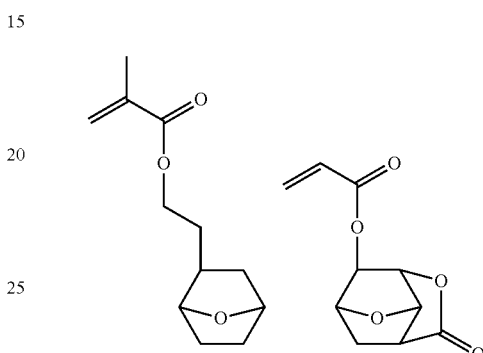
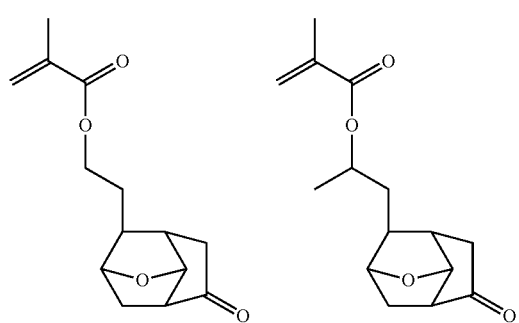
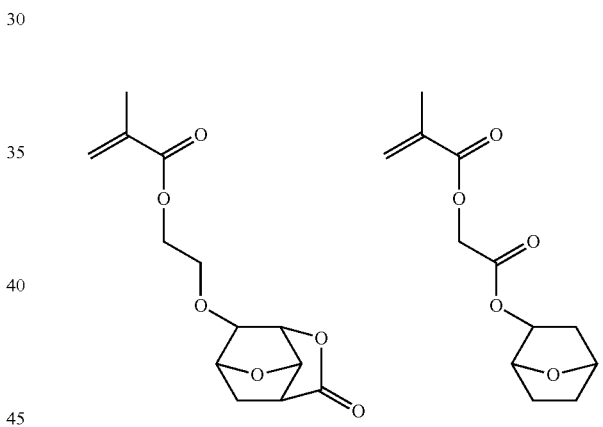
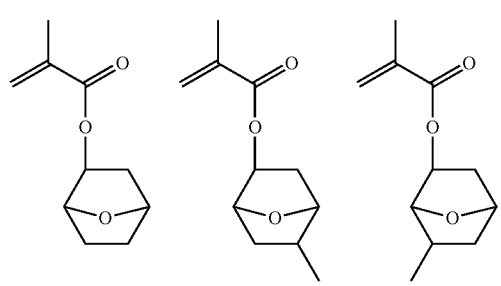
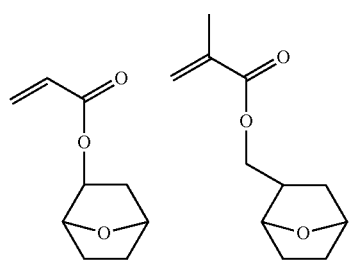
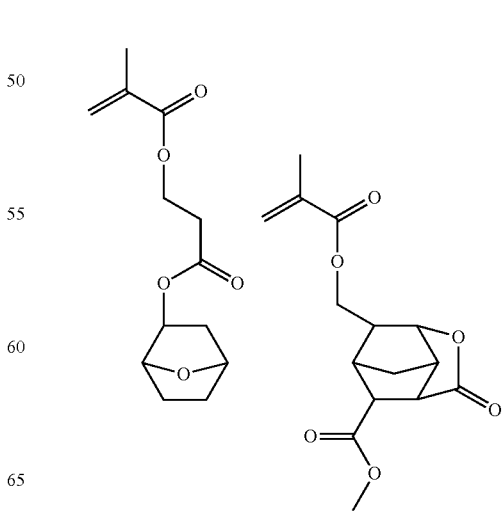

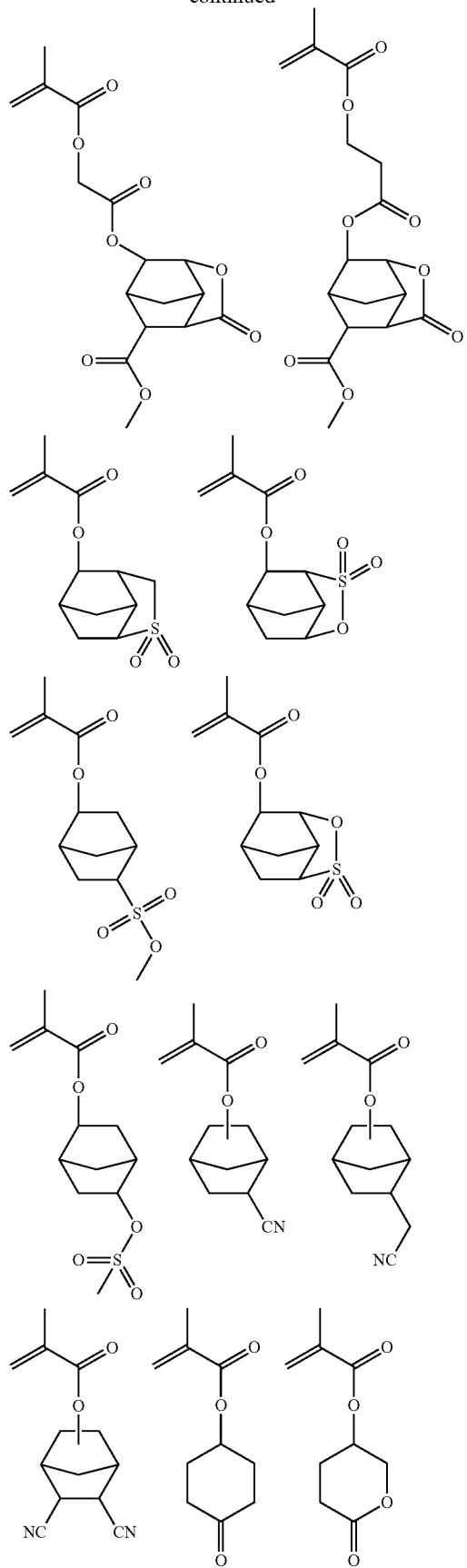
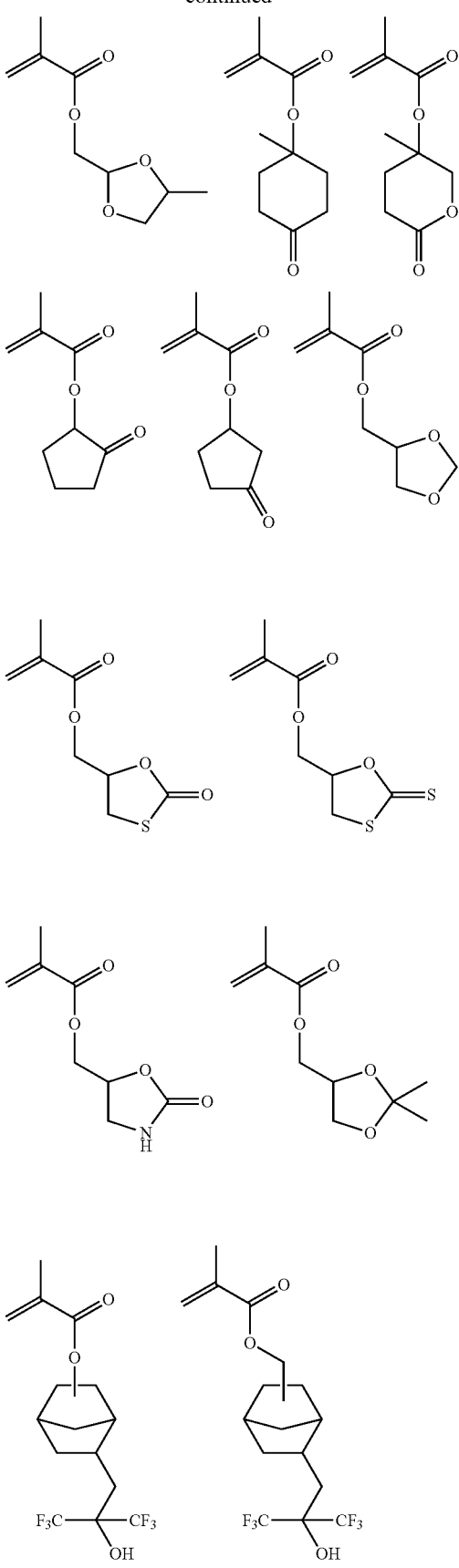

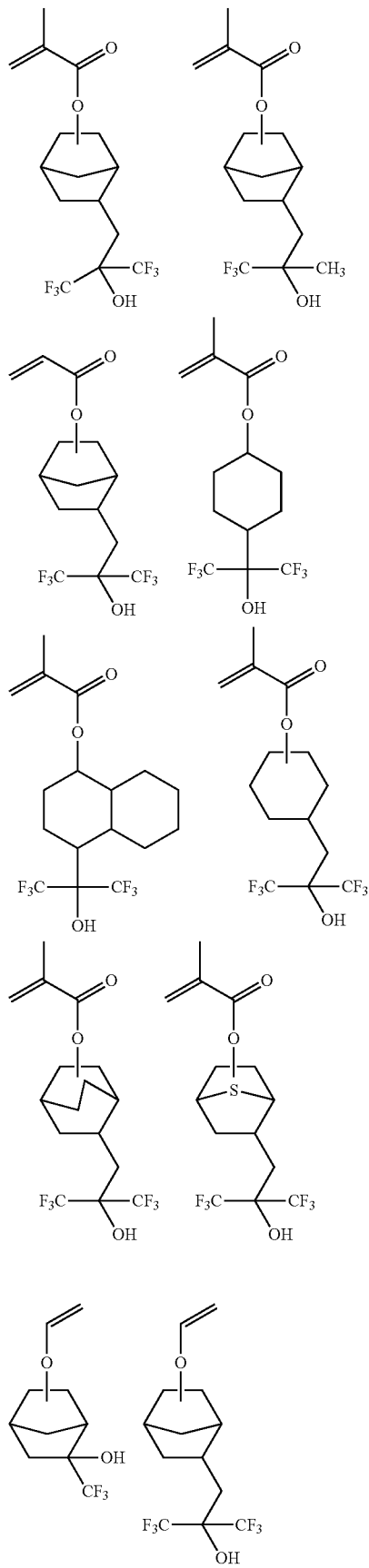
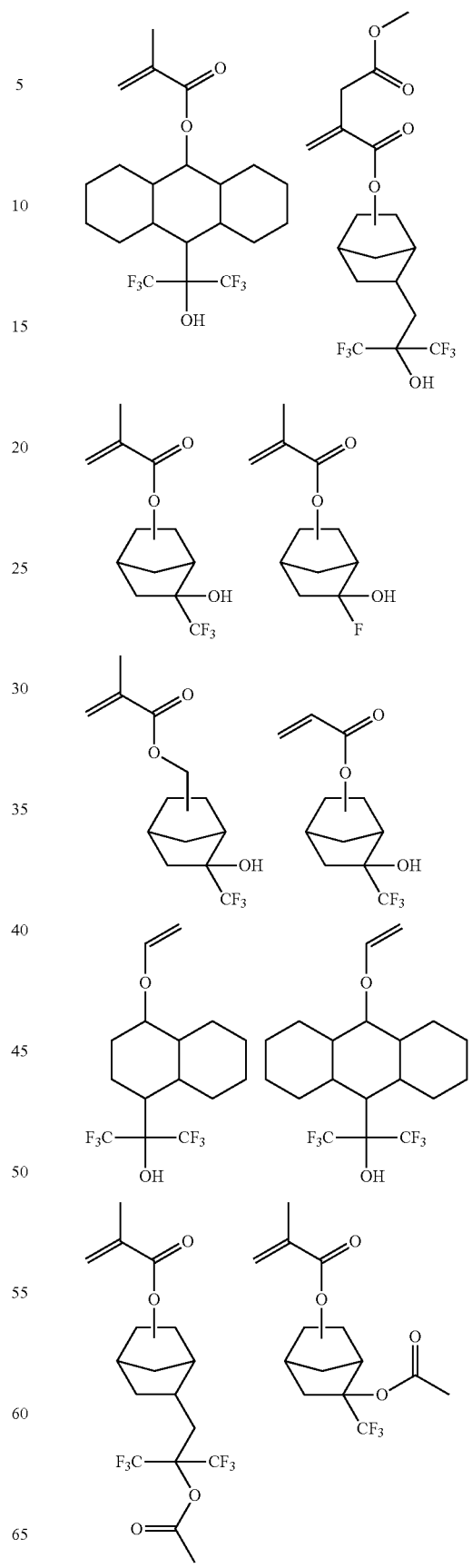

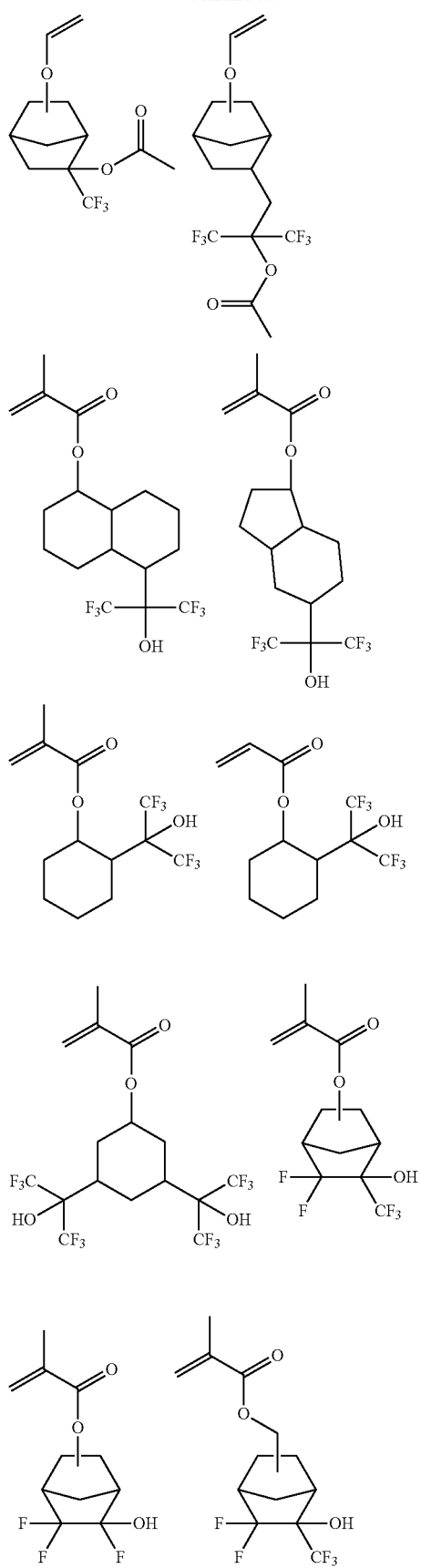
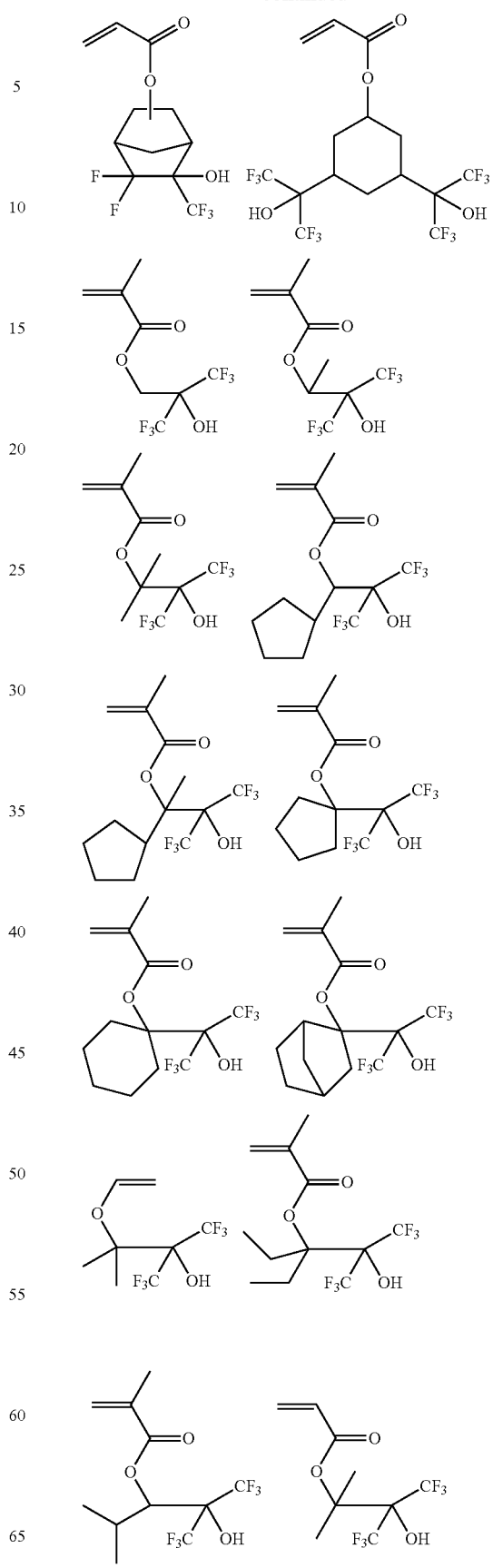

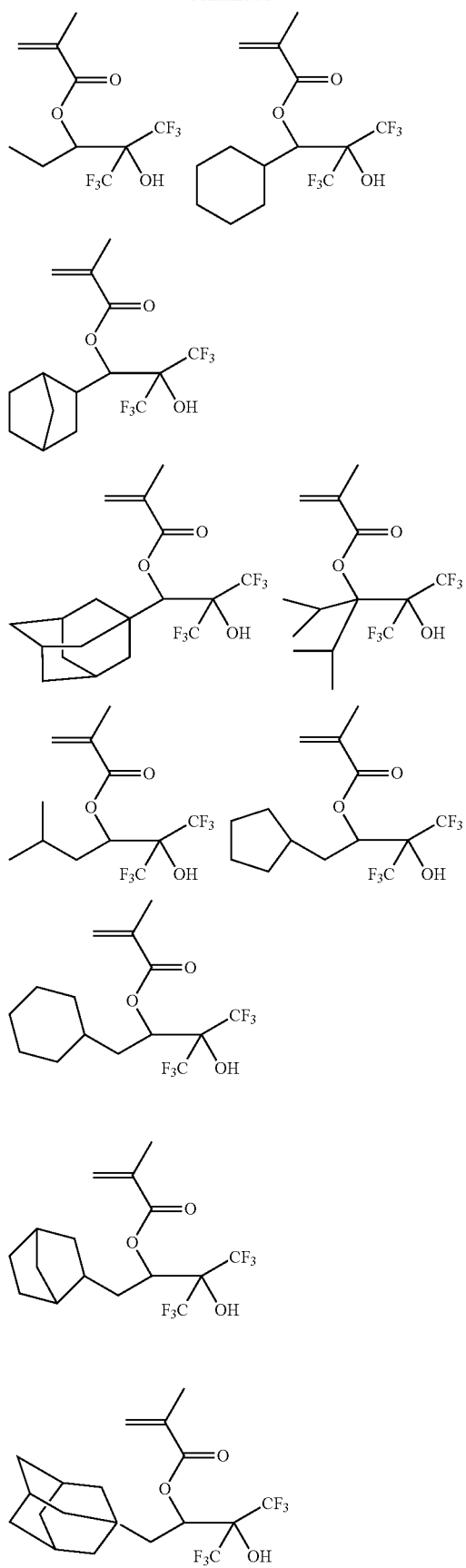
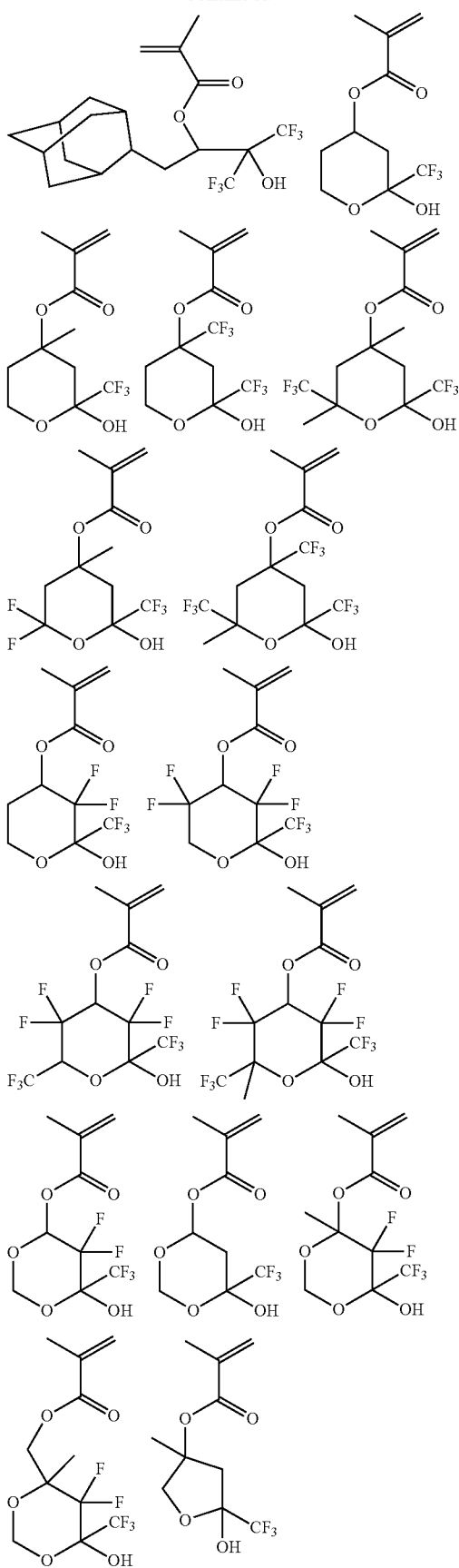

55
-continued
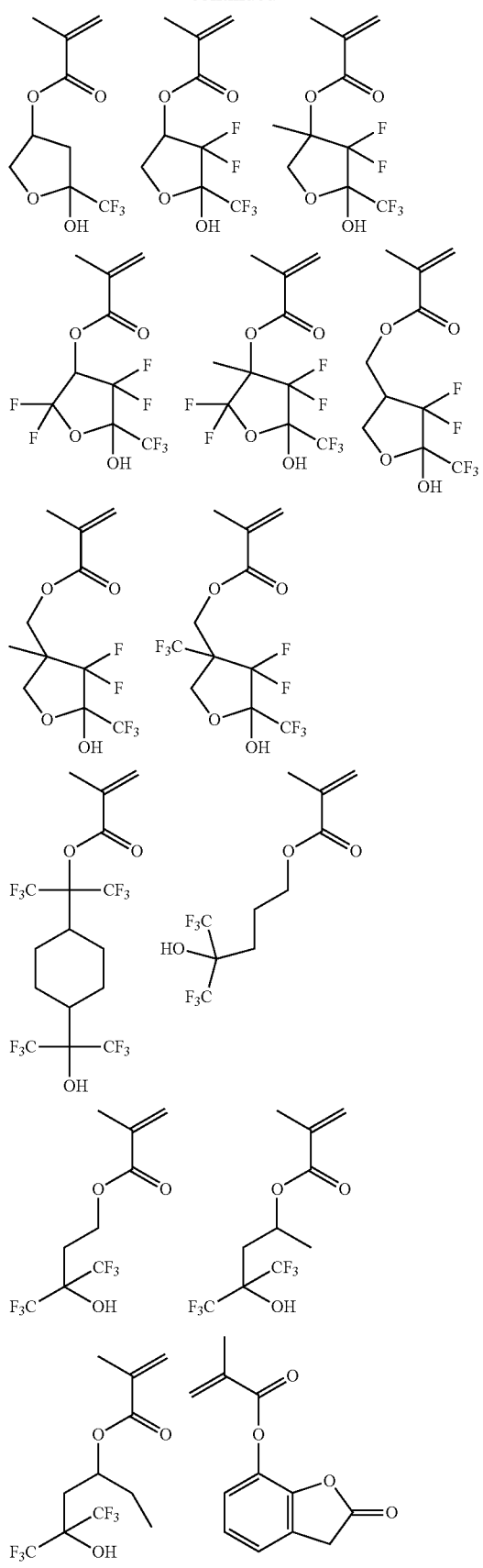
56
-continued
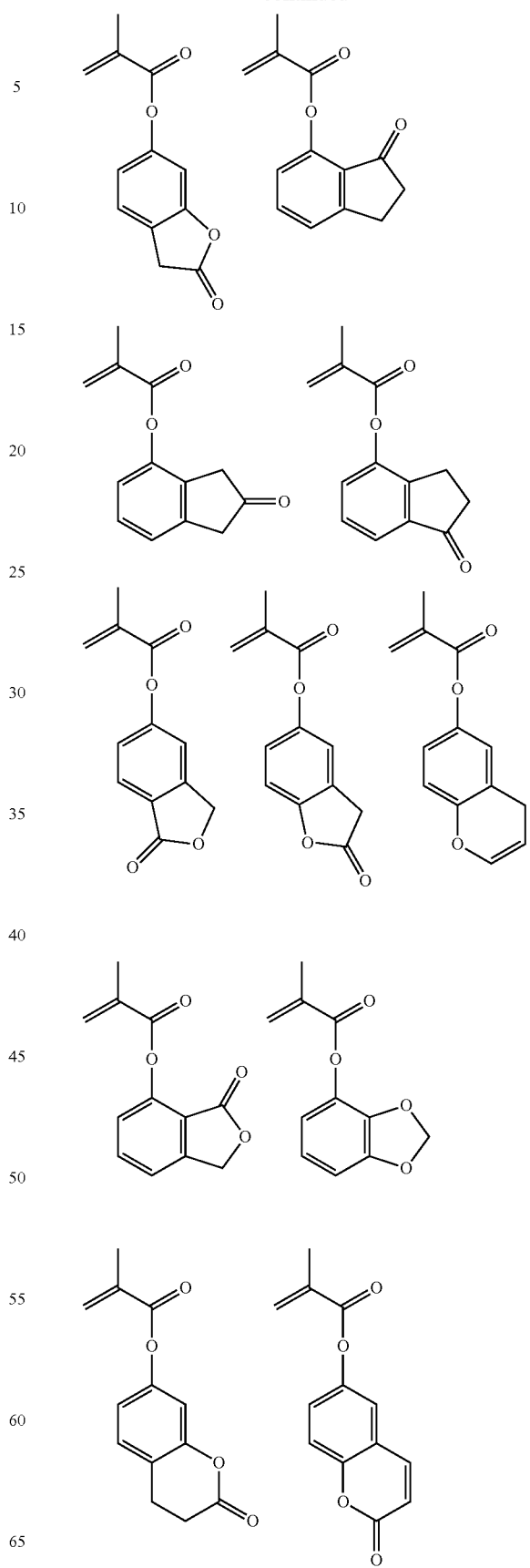

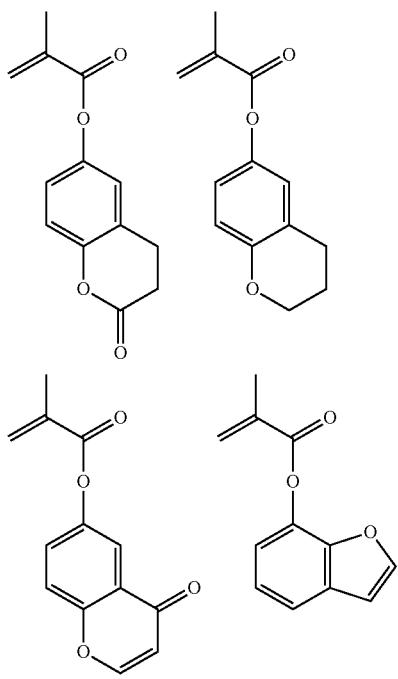
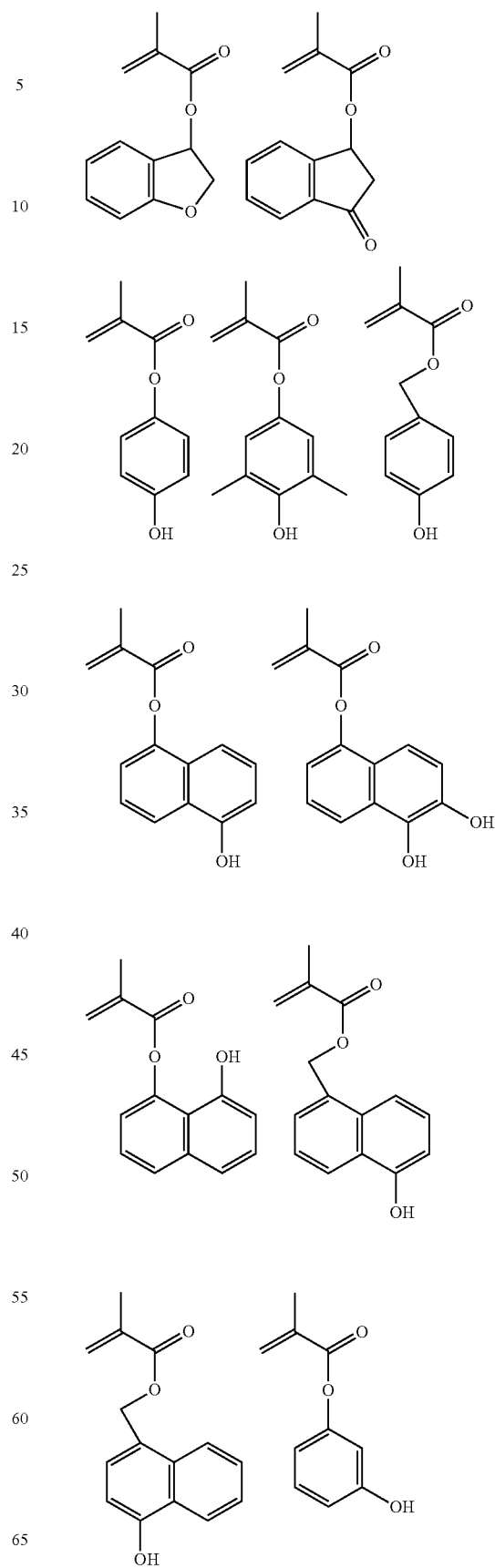

59
-continued
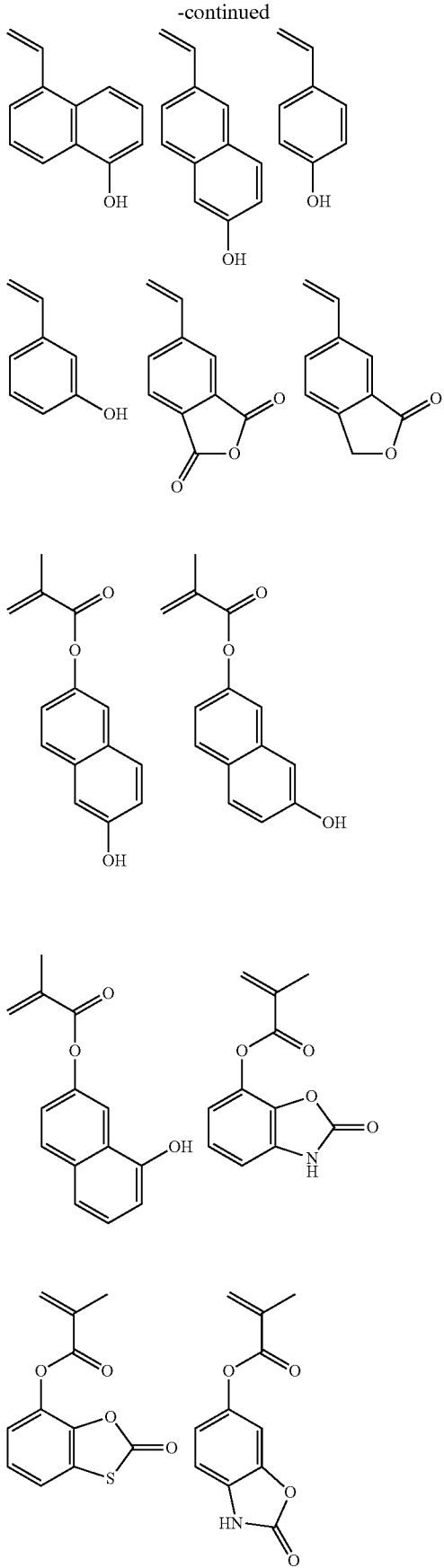
60
-continued
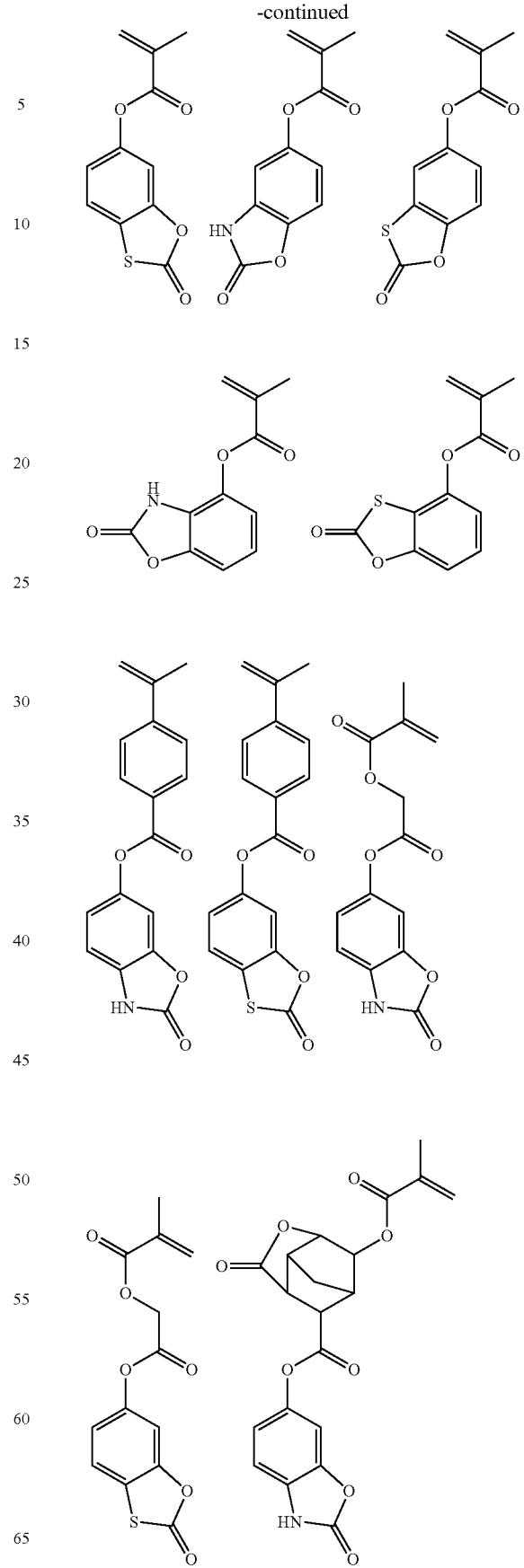

-continued

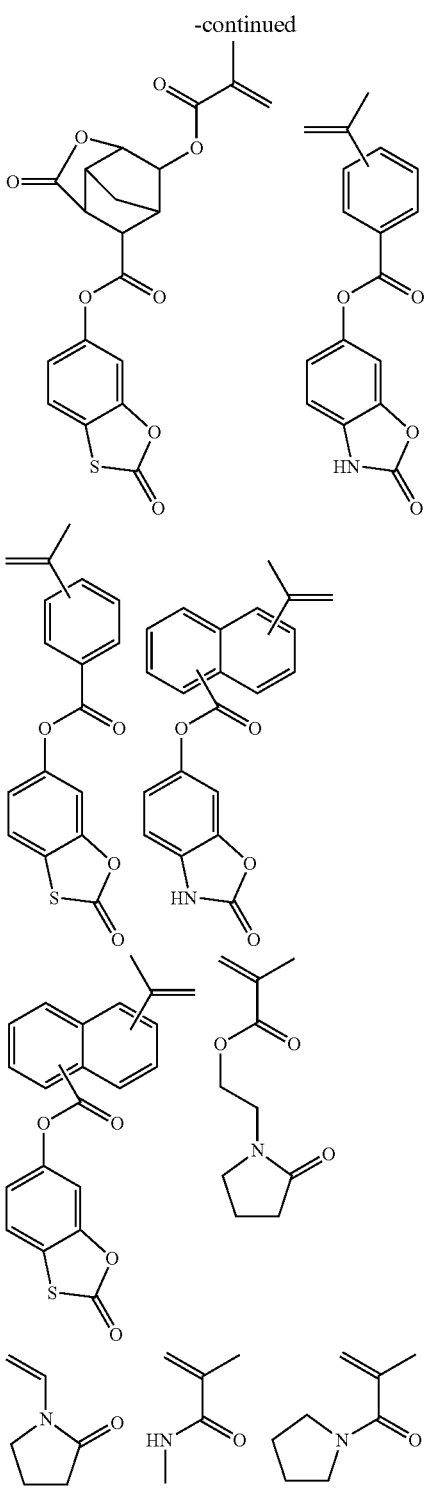

When recurring unit (d) is derived from a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxy group may be replaced by an acetyl, formyl, pivaloyl or similar group prior to polymerization, and the polymerization be followed by alkaline hydrolysis.

In a preferred embodiment, polymer P1 may have further copolymerized any of recurring units (e1), (e2) and (e3) having a sulfonium salt represented by the general formula (13) as described in JP-A 2006-178317. JP-A 2006-178317 discloses a sulfonium salt having sulfonic acid directly attached to the main chain. The attachment of an acid generator to the polymer main chain is effective in restraining acid diffusion, thereby preventing a reduction of resolution due to blur by acid diffusion. Also edge roughness (LER or LWR) is improved since the acid generator is uniformly dispersed.

(13)

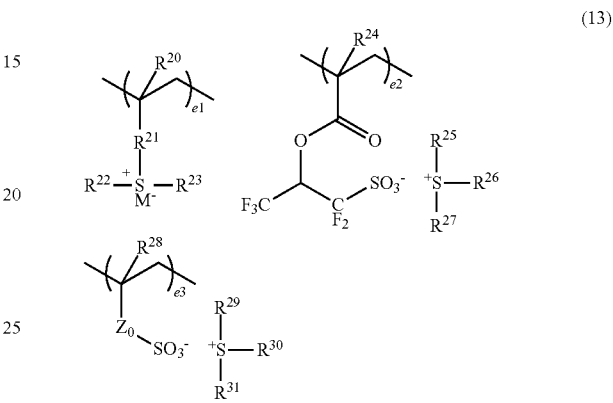

In formula (13), $R^{20}$, $R^{24}$ and $R^{28}$ each are hydrogen or methyl. $R^{21}$ is a single bond, phenylene, —O—R—, or —C(=O)—Y—R— wherein Y is oxygen or NH and R is a straight, branched or cyclic $C_1$-$C_6$ alkylene group, alkenylene group or phenylene group, which may contain a carbonyl (—CO—), ester (—COO—), ether (—O—) or hydroxyl radical. $R^{22}$, $R^{23}$, $R^{25}$, $R^{26}$, $R^{27}$, $R^{29}$, $R^{30}$, and $R^{31}$ are each independently a straight, branched or cyclic $C_1$-$C_{12}$ alkyl group which may contain a carbonyl, ester or ether radical, or a $C_6$-$C_{12}$ aryl group, $C_7$-$C_{20}$ aralkyl group, or thiophenyl group. $Z_0$ is a single bond, methylene, ethylene, phenylene, fluorinated phenylene, —O—$R^{32}$—, or —C(=O)—$Z_1$—$R^{32}$— wherein $Z_1$ is oxygen or NH and $R^{32}$ is a straight, branched or cyclic $C_1$-$C_6$ alkylene group, alkenylene group or phenylene group, which may contain a carbonyl, ester, ether or hydroxyl radical. $M^-$ is a non-nucleophilic counter ion.

Examples of the non-nucleophilic counter ion represented by $M^-$ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide acids such as bis(trifluoromethylsulfonyl)imide, bis(perfluoroethylsulfonyl)imide and bis(perfluorobutylsulfonyl)imide; methide acids such as tris(trifluoromethylsulfonyl)methide and tris(perfluoroethylsulfonyl)methide.

Other non-nucleophilic counter ions include sulfonates having fluorine substituted at α-position as represented by the general formula (K-1) and sulfonates having fluorine substituted at α- and β-positions as represented by the general formula (K-2).

(K-1)

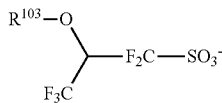
(K-2)

In formula (K-1), $R^{102}$ is hydrogen, or a straight, branched or cyclic $C_1$-$C_{20}$ alkyl group, $C_2$-$C_{20}$ alkenyl group, or $C_6$-$C_{20}$ aryl group, which may have an ether, ester, carbonyl radical, lactone ring or fluorine. In formula (K-2), $R^{103}$ is hydrogen, or a straight, branched or cyclic $C_1$-$C_{30}$ alkyl or acyl group, $C_2$-$C_{20}$ alkenyl group, or $C_6$-$C_{20}$ aryl or aryloxy group, which may have an ether, ester, carbonyl radical or lactone ring.

Polymer P1 may have further copolymerized therein recurring units (f) including indene units (f1), acenaphthylene units (f2), chromone units (f3), coumarin units (f4), and norbornadiene units (f5) as represented by the general formula (14).

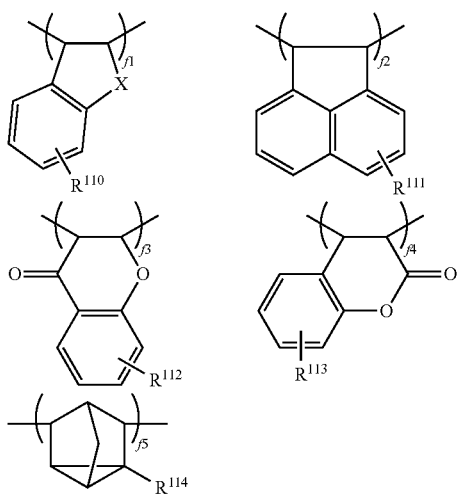
(14)

Herein, $R^{110}$ to $R^{114}$ each are hydrogen, a $C_1$-$C_{30}$ alkyl group or partially or entirely halo-substituted alkyl group, hydroxyl group, alkoxy group, alkanoyl group, alkoxycarbonyl group, $C_6$-$C_{10}$ aryl group, halogen atom, or 1,1,1,3,3,3-hexafluoro-2-propanol group. X is a methylene group, oxygen or sulfur atom. The subscripts f1 to f5 are numbers in the range: 0≤f1≤0.4, 0≤f2≤0.4, 0≤f3≤0.4, 0≤f4≤0.4, 0≤f5≤0.4, and 0≤f1+f2+f3+f4+f5≤0.4.

Besides the recurring units (a) to (f) described above, other recurring units (g) may be copolymerized, for example, styrene, vinyl naphthalene, vinyl anthracene, vinyl pyrene, and methylene indane.

The (co)polymer may be synthesized by any desired method, for example, by dissolving selected monomers corresponding to recurring units (a) to (g) in an organic solvent, adding a radical initiator thereto, and effecting heat polymerization. Examples of the organic solvent which can be used for polymerization include toluene, benzene, tetrahydrofuran, diethyl ether, dioxane, cyclohexane, cyclopentane, methyl ethyl ketone, and γ-butyrolactone. Examples of the polymerization initiator used herein include 2,2'-azobisisobutyronitrile (AIBN), 2,2'-azobis(2,4-dimethyl-valeronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

Where hydroxystyrene or hydroxyvinylnaphthalene is copolymerized, polymerization may be carried out using acetoxystyrene or acetoxyvinylnaphthalene instead of the hydroxystyrene or hydroxyvinylnaphthalene, after which alkaline hydrolysis be effected to deprotect the acetoxy group, thereby converting the product to poly(hydroxystyrene) or poly(hydroxyvinylnaphthalene). A base is used for the alkaline hydrolysis, for example, ammonia water or triethylamine. The reaction temperature is −20° C. to 100° C., preferably 0° C. to 60° C., and the reaction time is 0.2 to 100 hours, preferably 0.5 to 20 hours.

Molar fractions of recurring units (a) to (g) are typically in the range: 0<a<1.0, 0≤b≤1.0, 0≤c<1.0, 0≤b+c<1.0, 0<d<1.0, 0≤e1≤0.5, 0≤e2≤0.5, 0≤e3≤0.5, 0≤e1+e2+e3≤0.5, 0≤f≤0.5, and 0≤g≤0.5; preferably 0.01≤a≤0.8, 0≤b≤0.8, 0≤c≤0.8, 0.1≤b+c≤0.8, 0.1≤d≤0.9, 0≤e1≤0.4, 0≤e2≤0.4, 0≤e3≤0.4, 0≤e1+e2+e3≤0.4, 0≤f≤0.4, and 0≤g≤0.4, and more preferably 0.02≤a≤0.7, 0≤b≤0.7, 0≤c≤0.7, 0.1≤b+c≤0.7, 0.15≤d≤0.85, 0≤e1≤0.3, 0≤e2≤0.3, 0≤e3≤0.3, 0≤e1+e2+e3≤0.3, 0≤f≤0.3, and 0≤g≤0.3, with the proviso a+b+c+d+e+f+g=1.

The polymer serving as the base resin in the positive resist composition should preferably have a weight average molecular weight (Mw) in the range of 1,000 to 500,000, and more preferably 2,000 to 30,000, as measured by gel permeation chromatography (GPC) versus polystyrene standards using tetrahydrofuran as solvent. With too low a Mw, the resist composition may become less heat resistant. A polymer with too high a Mw may lose alkaline solubility and give rise to a footing phenomenon after pattern formation.

If a multi-component polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the multi-component copolymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, molecular weight or dispersity is acceptable.

Resist Composition

The polymer is advantageously used as a base resin in a positive resist composition, typically chemically amplified positive resist composition. Specifically, the polymer is used as a base resin and combined with any desired components including an organic solvent, acid generator, dissolution regulator, basic compound, and surfactant to formulate a positive resist composition. This positive resist composition has a very high sensitivity in that the dissolution rate in developer of the polymer in exposed areas is accelerated by catalytic reaction. In addition, the resist film has a high dissolution contrast, resolution, exposure latitude, and process adaptability, and provides a good pattern profile after exposure, yet better etching resistance, and minimal proximity bias because of restrained acid diffusion. By virtue of these advantages, the composition is fully useful in commercial application and suited as a pattern-forming material for the fabrication of VLSIs. Particularly when an acid generator is included to formulate a chemically amplified positive resist composition capable of utilizing acid catalyzed reaction, the composition has a higher sensitivity and is further improved in the properties described above.

Inclusion of a dissolution regulator may lead to an increased difference in dissolution rate between exposed and unexposed areas and a further improvement in resolution. Addition of a basic compound may be effective in suppressing the diffusion rate of acid in the resist film, achieving a further improvement in resolution. Addition of a surfactant may improve or control the coating characteristics of the resist composition.

The positive resist composition may include an acid generator in order for the composition to function as a chemically amplified positive resist composition. Typical of the acid generator used herein is a photoacid generator (PAG) capable of generating an acid in response to actinic light or radiation. It is any compound capable of generating an acid upon exposure to high-energy radiation. The preferred photoacid generators include the sulfonium salts and PAGs described in JP-A 2009-269953 and the PAGs described in JP 3995575. Any sulfonium salt, iodonium salt, sulfonyldiazomethane, N-sulfonyloxyimide, and oxime-O-sulfonate acid generators may be used.

Among others, sulfonium salts having the general formula (15) are preferred.

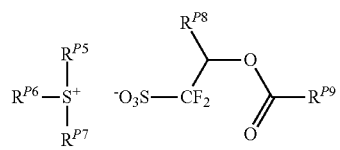

(15)

Herein $R^{P5}$, $R^{P6}$, and $R^{P7}$ are each independently a straight, or branched $C_1$-$C_{10}$ alkyl, alkenyl or oxoalkenyl group which may contain fluorine, hydroxyl or ether bond, or a substituted or unsubstituted $C_6$-$C_{18}$ aryl, aralkyl or aryloxoalkyl group. Alternatively, any two or more of $R^{P5}$, $R^{P6}$, and $R^{P7}$ may bond together to form a ring with the sulfur atom. $R^{P8}$ is hydrogen or trifluoromethyl. $R^{P9}$ is a straight, branched or cyclic $C_6$-$C_{30}$ monovalent hydrocarbon group which may contain a heteroatom.

Examples of the sulfonium cation of formula (15) are shown below, but are not limited thereto.

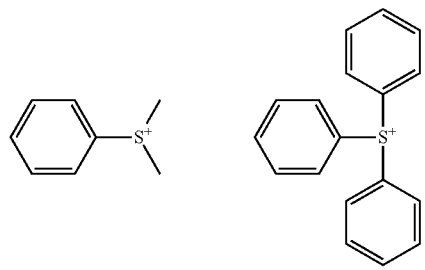

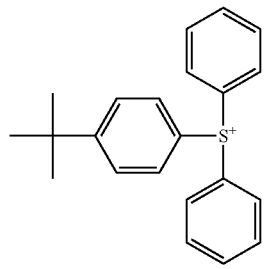

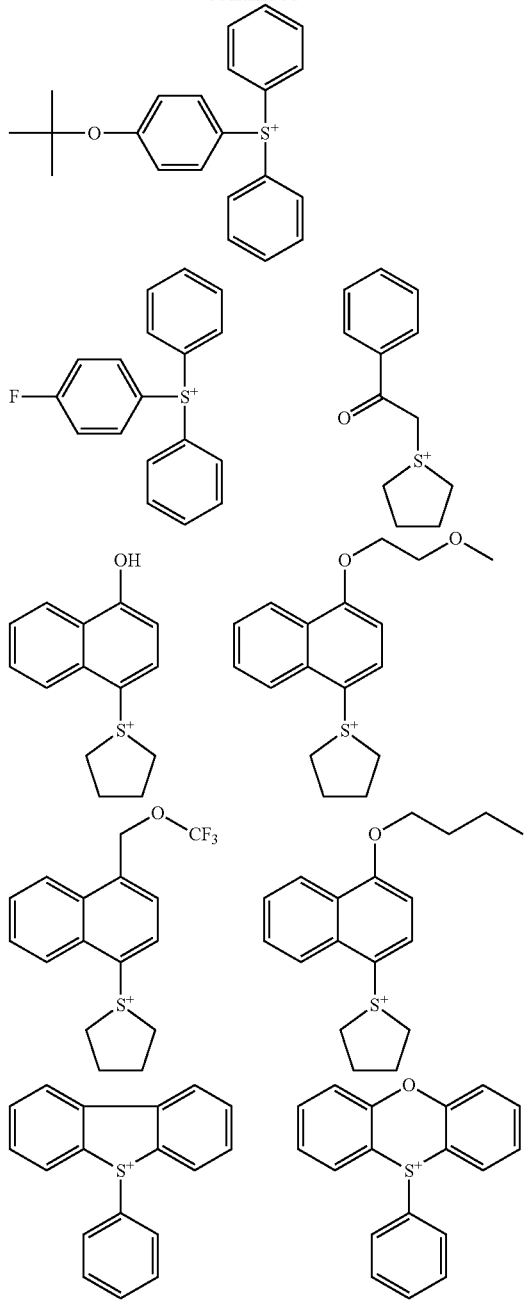

Examples of substituent group $R^{P9}$ on the sulfonate anion of formula (15) are shown below, but are not limited thereto.

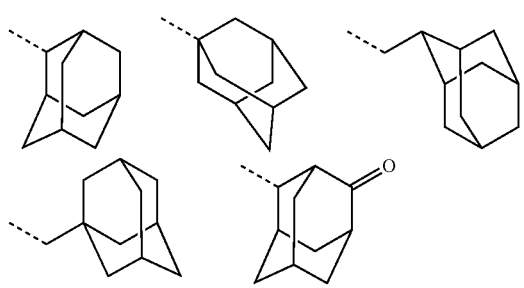

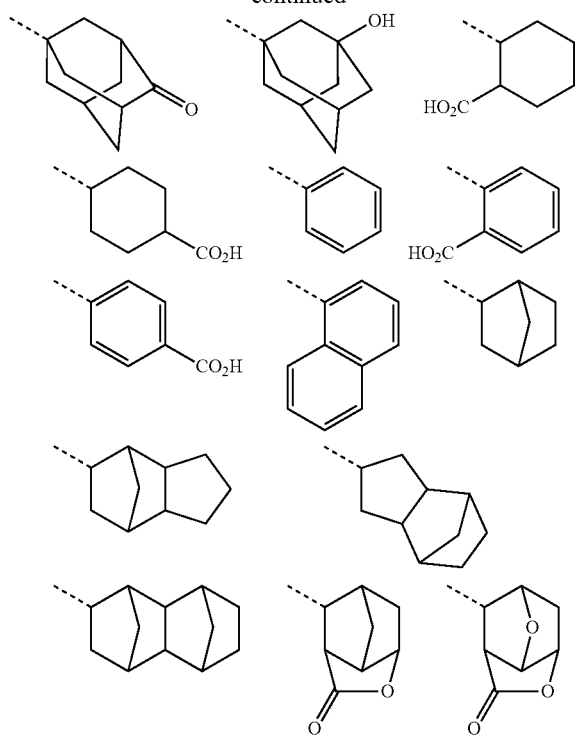
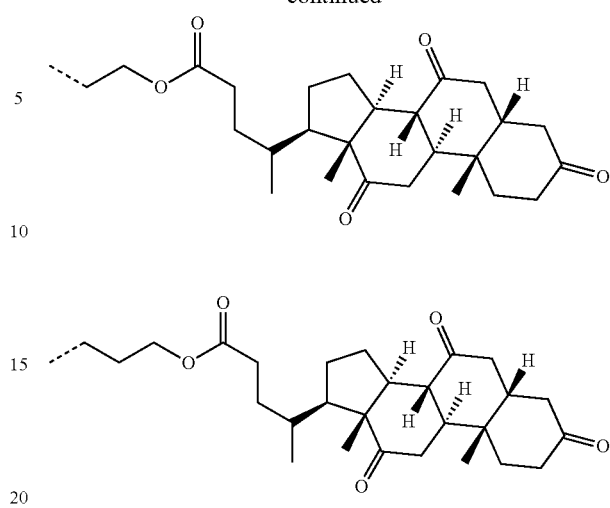
An appropriate combination of the sulfonium cation with the sulfonate anion may be selected while taking into account the stability of sulfonium cation in the resist composition, the acid generation efficiency at the exposure wavelength, and/or the diffusion of the generated acid. Preferred sulfonium salts are shown below.
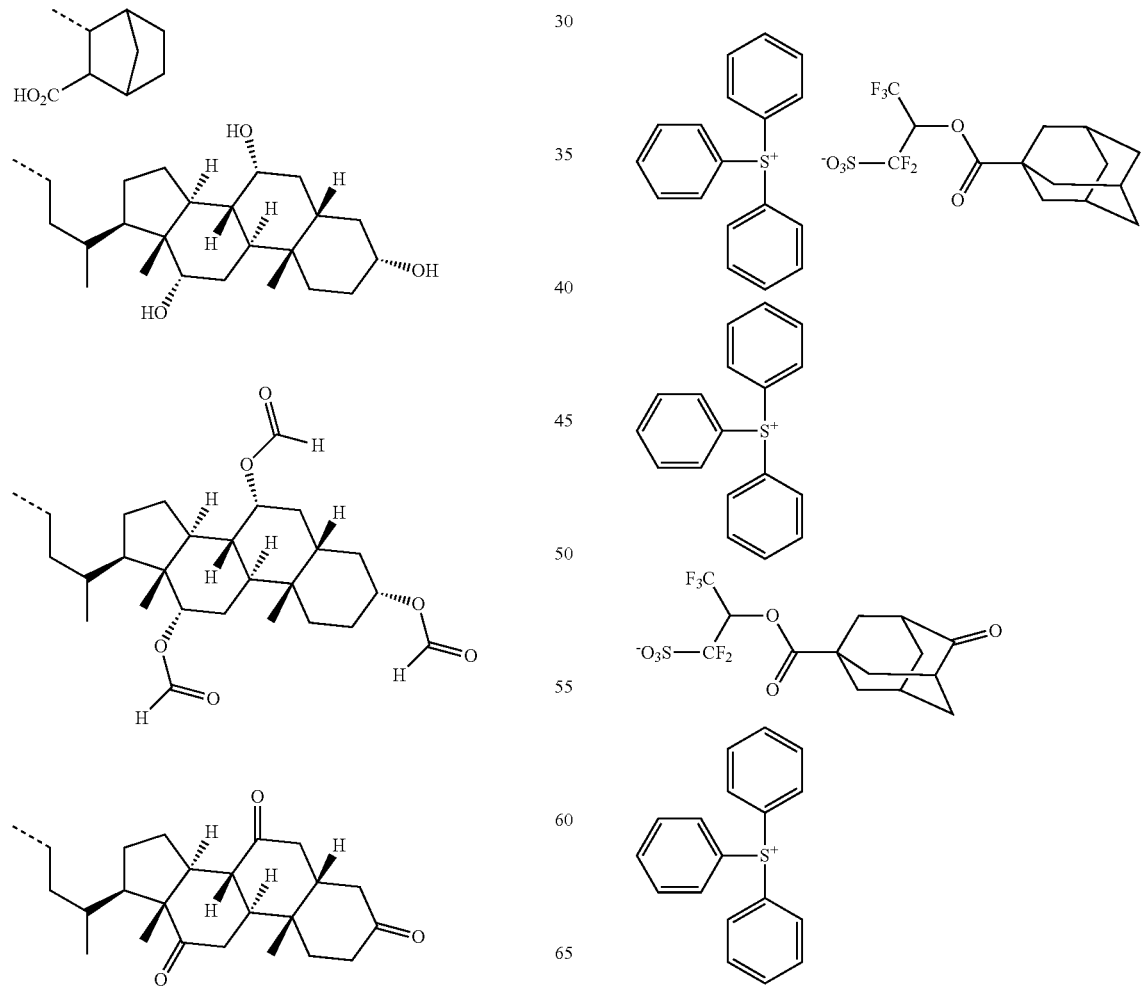

69
-continued
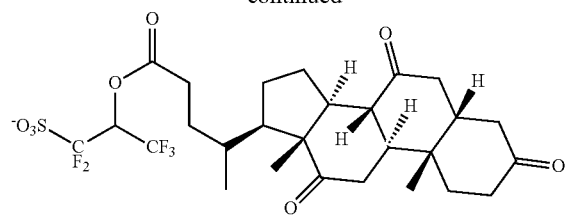
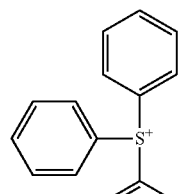
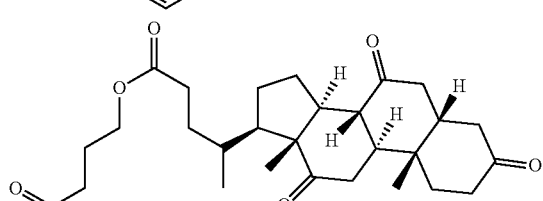
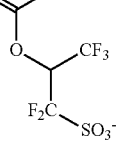
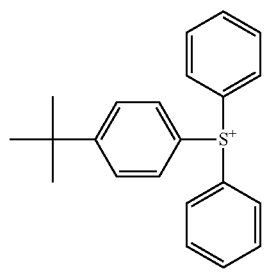
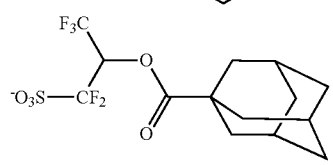
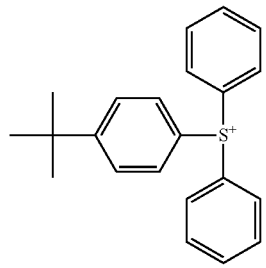
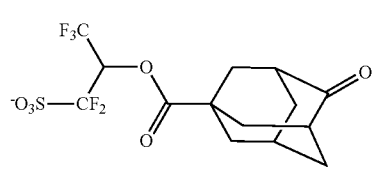
70
-continued
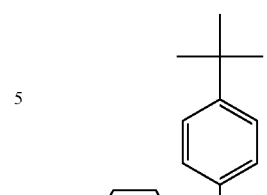
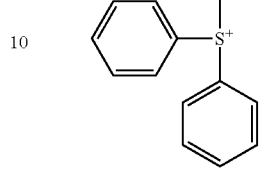
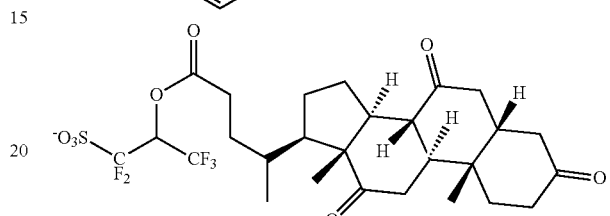
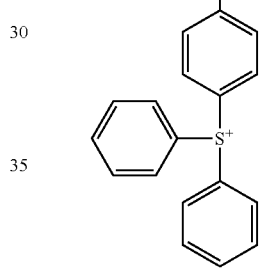
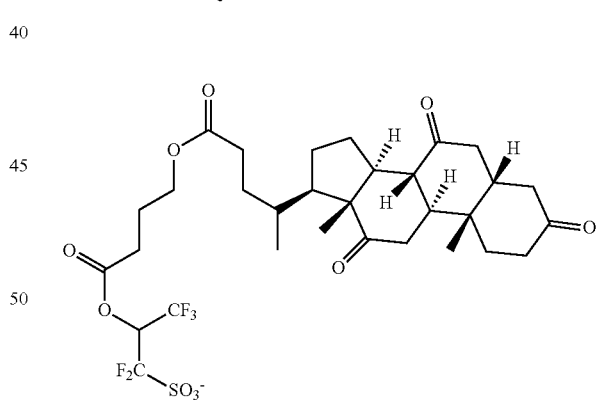
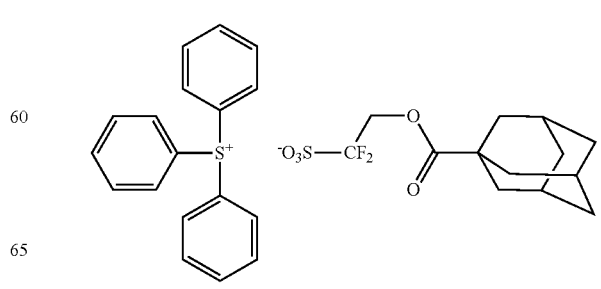

71
-continued
72
-continued
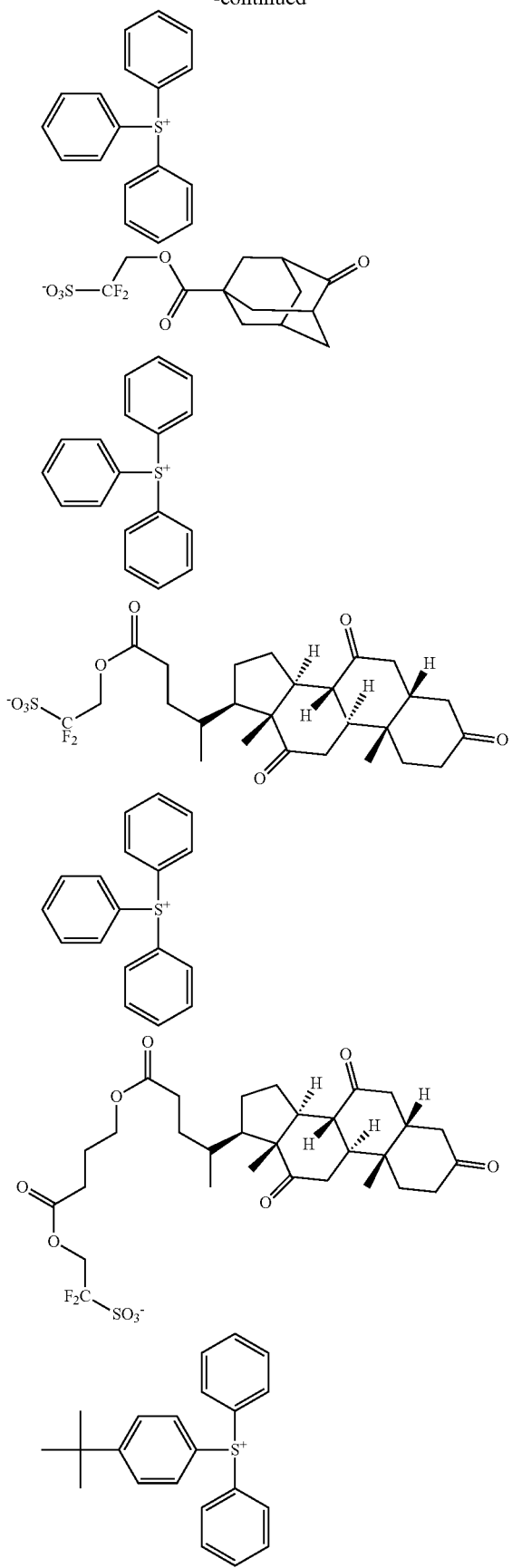
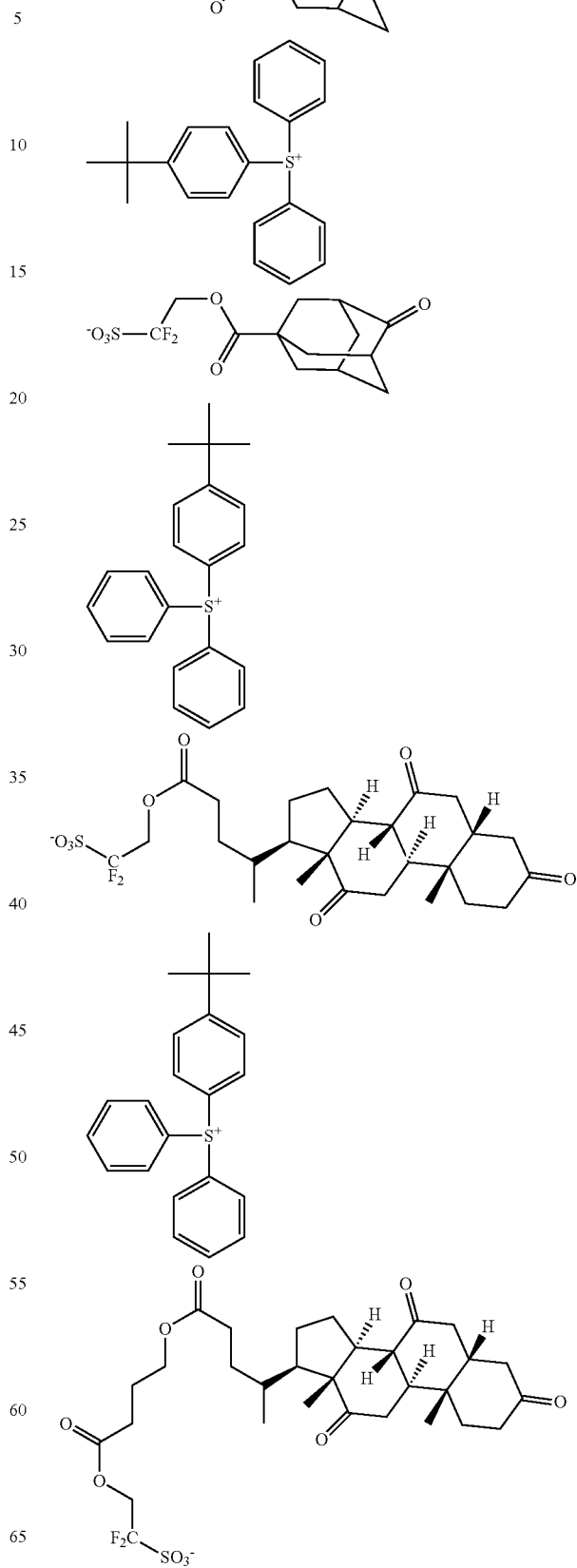

-continued
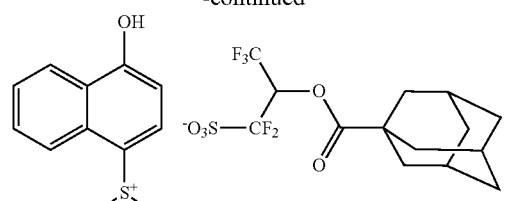
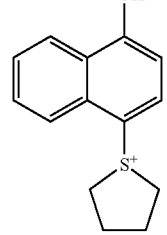
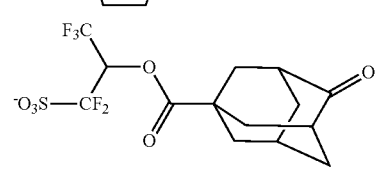
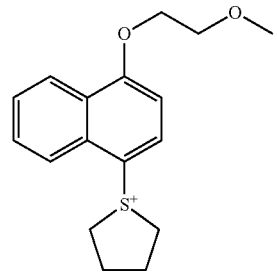
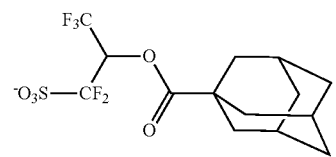
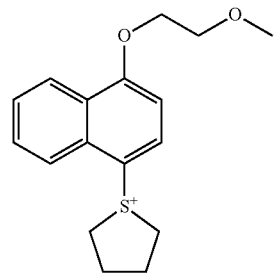
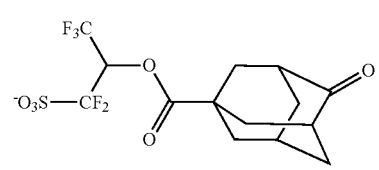
-continued
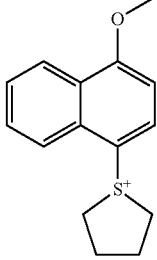
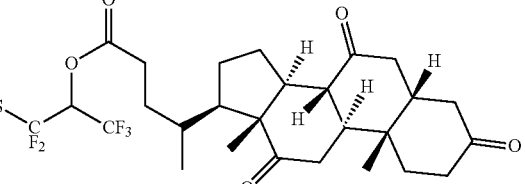
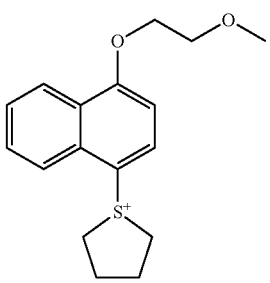
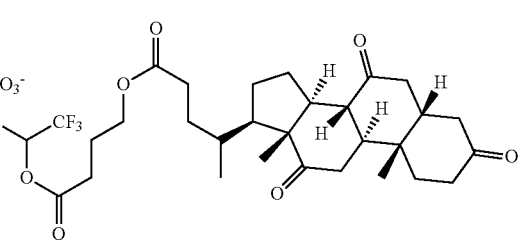
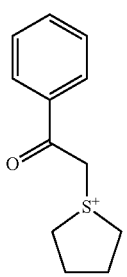
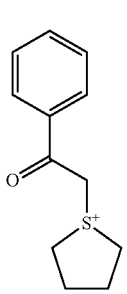

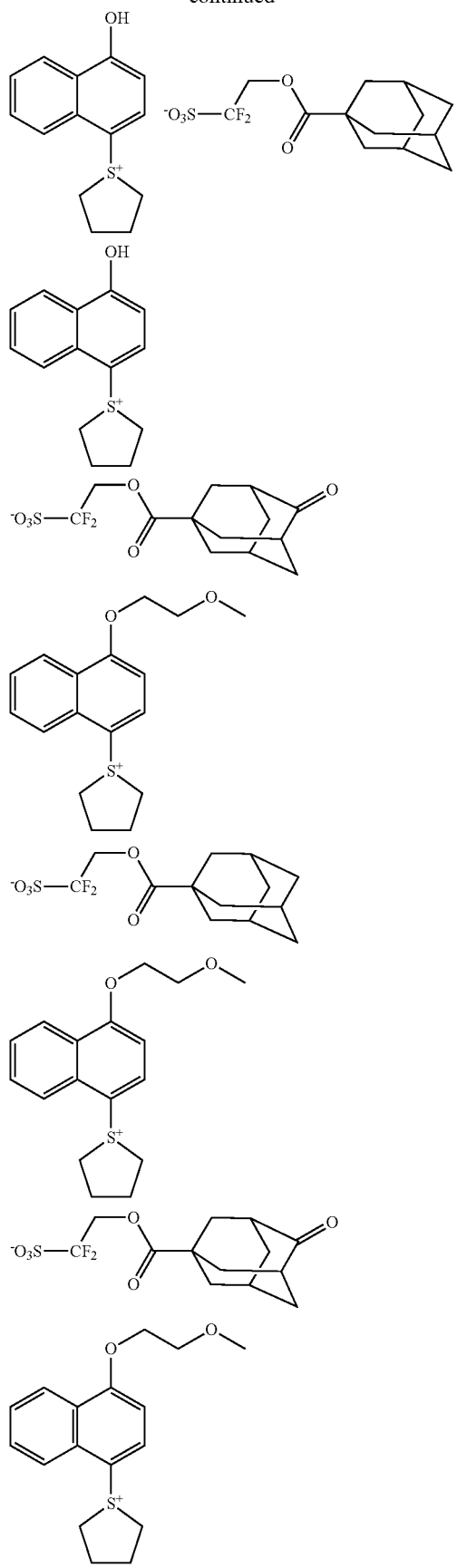
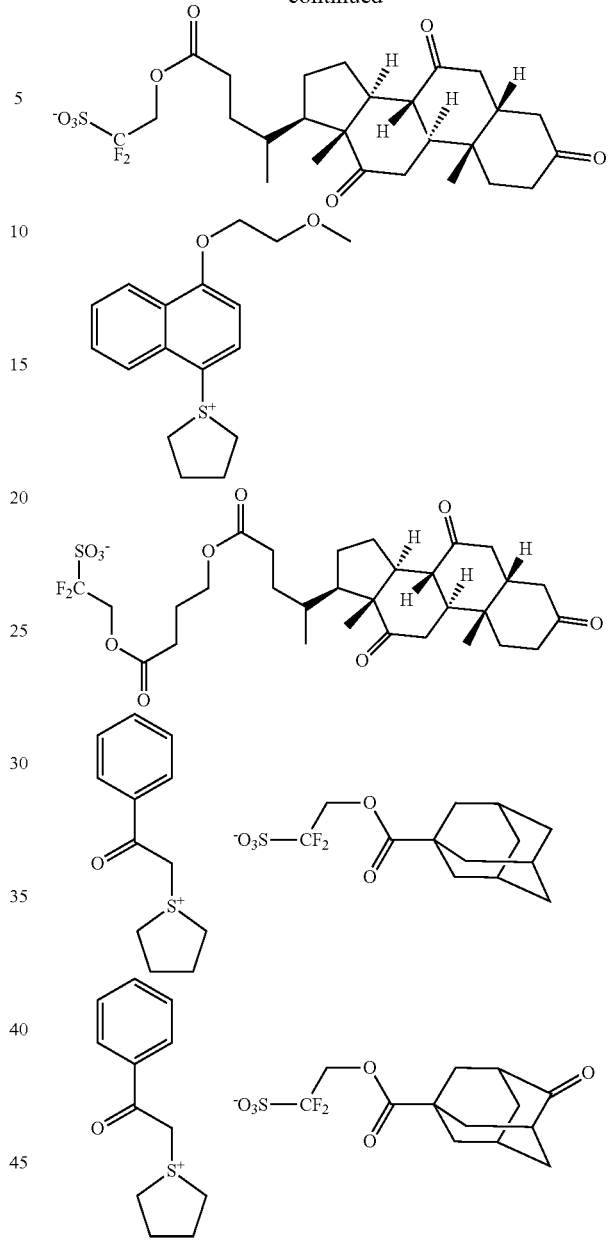

The positive resist composition may further comprise an organic solvent, basic compound, dissolution regulator, surfactant, and acetylene alcohol, alone or in combination.

The organic solvent used herein is described in U.S. Pat. No. 7,537,880 (JP-A 2008-111103, paragraphs [0144]-[0145]). Illustrative, non-limiting, examples of the organic solvent include ketones such as cyclohexanone, cyclopentanone and methyl 2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone.

Examples of the basic compound include primary, secondary and tertiary amine compounds as described in JP-A 2008-111103, paragraphs [0146]-[0164], specifically amine compounds having hydroxyl, ether, ester, lactone ring, cyano, or sulfonic acid ester group, and carbamate compounds as described in JP 3790649.

Also onium salts such as sulfonium salts, iodonium salts and ammonium salts of sulfonic acids which are not fluorinated at α-position as described in US 2008153030 (JP-A 2008-158339) and similar onium salts of carboxylic acids may be used as the quencher. If the α-position non-fluorinated sulfonic acid salt or carboxylic acid salt is co-present with an α-position fluorinated sulfonic acid, imide acid, and methide acid, then a salt exchange occurs to generate an α-position non-fluorinated sulfonic acid or carboxylic acid. Since the acid strength of this α-position non-fluorinated sulfonic acid or carboxylic acid is insufficient to induce deprotection reaction, the sulfonium salt, iodonium salt or ammonium salt can function as a quencher. In particular, since sulfonium salts and iodonium salts of an α-position non-fluorinated sulfonic acid and a carboxylic acid are photo-decomposable, those portions receiving a high light intensity are reduced in quenching capability and increased in the concentration of a α-position fluorinated sulfonic acid, imide acid, or methide acid. As a result, the exposed portions are improved in contrast.

Exemplary surfactants are described in JP-A 2008-111103, paragraphs [0165]-[0166]. Exemplary dissolution regulators are described in JP-A 2008-122932 (US 2008090172), paragraphs [0155]-[0178], and exemplary acetylene alcohols in paragraphs [0179]-[0182].

An appropriate amount of the acid generator used is 0.01 to 100 parts, and preferably 0.1 to 80 parts. An appropriate amount of the organic solvent used is 50 to 10,000 parts, especially 100 to 5,000 parts. The dissolution regulator may be blended in an amount of 0 to 50 parts, preferably 0 to 40 parts, the basic compound in an amount of 0 to 100 parts, preferably 0.001 to 50 parts, and the surfactant in an amount of 0 to 10 parts, preferably 0.0001 to 5 parts. All amounts are expressed in parts by weight relative to 100 parts by weight of the base resin. It is understood that the acid generator need not necessarily be added when the polymer has copolymerized therein an acid generator component selected from recurring units (e1), (e2) and (e3) represented by formula (13).

Another polymer may be added to the resist composition for improving the water repellency on surface of a resist film as spin coated. The water repellency improver may be used in the topcoatless immersion lithography. The water repellency improver has a specific structure with a 1,1,1,3,3,3-hexafluoro-2-propanol residue, as described in JP-A 2007-297590, JP-A 2008-111103, and JP-A 2008-122932.

The water repellency improver added to the resist composition should be soluble in the organic solvent as the developer. The water repellency improver of specific structure with a 1,1,1,3,3,3-hexafluoro-2-propanol residue is highly soluble in the developer. A polymer having an amino group or amine salt copolymerized as recurring units may serve as the water repellency improver and is effective for preventing evaporation of acid during PEB and avoiding any hole pattern opening failure after development. An appropriate amount of the water repellency improver added is typically 0.1 to 20 parts, preferably 0.5 to 10 parts by weight per 100 parts by weight of the base resin.

Process

The positive resist composition, typically chemically amplified positive resist composition comprising a polymer having a carbamate capable of generating an amino group under the action of acid and an acid labile group represented by formula (2), an acid generator, and a basic compound in an organic solvent is used in the fabrication of various integrated circuits. Pattern formation using the resist composition may be performed by well-known lithography processes. The process generally involves coating, prebaking, exposure, PEB, and development. If necessary, any additional steps may be added.

For example, the positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, or MoSi) by a suitable coating technique such as spin coating, roll coating, flow coating, dip coating, spray coating or doctor coating. The coating is prebaked on a hot plate at a temperature of 60 to 150° C. for 10 seconds to 30 minutes, preferably 80 to 120° C. for 30 seconds to 20 minutes. The resulting resist film is generally 0.1 to 2.0 μm thick.

The resist film is then exposed to a desired pattern of high-energy radiation such as UV, deep-UV, EB, x-ray, excimer laser light, γ-ray, synchrotron radiation or vacuum UV (soft x-ray), directly or through a mask. Preferably g-line, i-line, KrF excimer laser, ArF excimer laser, EB, or soft x-ray of 3 to 15 nm wavelength is used. The exposure dose is preferably about 1 to 200 $mJ/cm^2$, more preferably about 10 to 100 $mJ/cm^2$, or 0.1 to 100 $\mu C/cm^2$, more preferably 0.5 to 50 $\mu C/cm^2$. In the case of ArF excimer laser lithography of 193 nm, the exposure may be done either in a dry atmosphere such as air or nitrogen stream or by immersion lithography in water. The ArF immersion lithography uses deionized water or liquids having a refractive index of at least 1 and highly transparent to the exposure wavelength such as alkanes as the immersion solvent. The immersion lithography involves exposing the prebaked resist film to light through a projection lens, with pure water or another liquid introduced between the resist film and the projection lens. Since this allows lenses to be designed to a NA of 1.0 or higher, formation of finer feature size patterns is possible. The immersion lithography is important for the ArF lithography to survive to the 45-nm node. In the case of immersion lithography, deionized water rinsing (or post-soaking) may be carried out after exposure for removing water droplets left on the resist film, or a protective film may be applied onto the resist film after pre-baking for preventing any leach-out from the resist film and improving water slip on the film surface. The resist protective film used in the immersion lithography is preferably formed from a solution of a polymer having 1,1,1,3,3,3-hexafluoro-2-propanol residues which is insoluble in water, but soluble in an alkaline developer liquid, in a solvent selected from alcohols of at least 4 carbon atoms, ethers of 8 to 12 carbon atoms, and mixtures thereof. The resist film is further baked (PEB) on a hot plate at 60 to 150° C. for 10 seconds to 30 minutes, preferably 80 to 120° C. for 30 seconds to 20 minutes.

Thereafter the resist film is developed with a developer in the form of an aqueous base solution for 3 seconds to 3 minutes, preferably 5 seconds to 2 minutes by conventional techniques such as dip, puddle or spray techniques. Suitable developers are 0.1 to 10 wt %, preferably 2 to 10 wt %, more preferably 2 to 5 wt % aqueous solutions of tetramethylammonium hydroxide (TMAH), tetraethylammonium hydroxide (TEAH), tetrapropylammonium hydroxide (TPAH) and tetrabutylammonium hydroxide (TBAH). The resist film in the exposed area is dissolved in the developer whereas the resist film in the unexposed area is not dissolved. In this way, the desired positive pattern is formed on the substrate. It is appreciated that the resist composition of the invention is best suited for micro-patterning using such high-energy radiation as EB, EUV (soft x-ray), x-ray, γ-ray and synchrotron radiation among others.

Although TMAH aqueous solution is generally used as the developer, TEAH, TPAH and TBAH having a longer alkyl chain are effective in inhibiting the resist film from being swollen during development and thus preventing pattern collapse. JP 3429592 describes an example using an aqueous TBAH solution for the development of a polymer comprising recurring units having an alicyclic structure such as adamantane methacrylate and recurring units having an acid labile group such as t-butyl methacrylate, the polymer being water repellent due to the absence of hydrophilic groups.

The TMAH developer is most often used as 2.38 wt % aqueous solution, which corresponds to 0.26N. The TEAH, TPAH, and TBAH aqueous solutions should preferably have an equivalent normality. The concentration of TEAH, TPAH, and TBAH that corresponds to 0.26N is 3.84 wt %, 5.31 wt %, and 6.78 wt %, respectively.

When a pattern with a line size of 32 nm or less is resolved by the EB and EUV lithography, there arises a phenomenon that lines become wavy, lines merge together, and merged lines collapse. It is believed that this phenomenon occurs because lines are swollen in the developer and the thus expanded lines merge together. Since the swollen lines containing liquid developer are as soft as sponge, they readily collapse under the stress of rinsing. For this reason, the developer using a long-chain alkyl developing agent is effective for preventing film swell and hence, pattern collapse.

EXAMPLE

Examples of the invention are given below by way of illustration and not by way of limitation. The abbreviation "pbw" is parts by weight. For all polymers, Mw and Mn are determined by GPC versus polystyrene standards using tetrahydrofuran solvent.

Synthesis Example 1

Nitrogen-containing monomers within the scope of the invention were synthesized as follows.

Synthesis Example 1-1

Synthesis of 1-tert-butoxycarbonylpiperidin-4-yl methacrylate (Monomer 1)

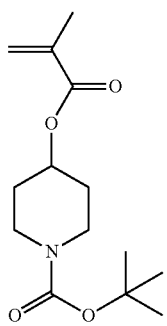 [SMILES: C=C(C)C(=O)OC1CCN(C(=O)OC(C)(C)C)CC1]

In a nitrogen atmosphere, 50 g of 1-tert-butoxy-carbonylpiperidin-4-ol, 26.8 g of triethylamine, and 2.9 g of 4-dimethylaminopyridine were mixed in 200 g of toluene. Under ice cooling, 40 g of methacrylic anhydride was added dropwise to the solution at a temperature below 40° C. The solution was stirred for 4 hours at room temperature, whereupon 100 g of water was added dropwise below 20° C. to quench the reaction. This was followed by standard aqueous workup and vacuum distillation, obtaining 48.9 g of 1-tert-butoxycarbonylpiperidin-4-yl methacrylate (yield 90%).

IR (D-ATR): σ=2953, 1721, 1699, 1638, 1429, 1366, 1327, 1294, 1274, 1239, 1168, 1030, 990, 944, 863, 815, 752 cm$^{-1}$ $^1$H-NMR (300 MHz in DMSO-d$_6$): δ=6.04 (1H, m), 5.67 (1H, m), 4.91 (1H, m), 3.53 (2H, m), 3.25 (2H, m), 1.87 (1H, s), 1.79 (2H, m), 1.50 (1H, m), 1.39 (9H, s) ppm Synthesis Example 1-2

Synthesis of 1-allyloxycarbonylpiperidin-4-yl methacrylate (Monomer 2)

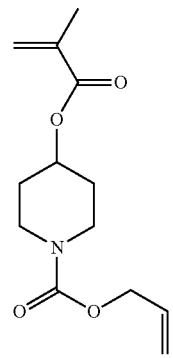 [SMILES: C=CCOC(=O)N1CCC(OC(=O)C(=C)C)CC1]

Synthesis was carried out as in Synthesis Example 1-1 aside from using 1-allyloxycarbonylpiperidin-4-ol instead of 1-tert-butoxycarbonylpiperidin-4-ol. There was obtained 1-allyloxycarbonylpiperidin-4-yl methacrylate (yield 87%).

Synthesis Example 1-3

Synthesis of (1-tert-butoxycarbonylpiperidin-4-yloxy-carbonyl)methyl methacrylate (Monomer 3)

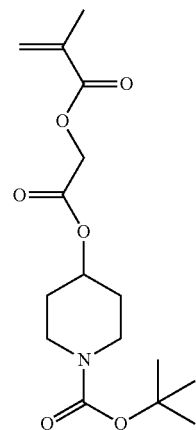 [SMILES: C=C(C)C(=O)OCC(=O)OC1CCN(C(=O)OC(C)(C)C)CC1]

Synthesis was carried out as in Synthesis Example 1-1 aside from using methacryloyloxyacetic acid chloride instead of methacrylic anhydride. There was obtained (1-tert-butoxycarbonylpiperidin-4-yloxycarbonyl)methyl methacrylate (yield 79%).

Synthesis Example 2

Polymers for use in resist compositions within the scope of the invention were synthesized in accordance with the formulation shown below.

Synthesis Example 2-1

Synthesis of Polymer 1

Under a nitrogen blanket, a flask was charged with 1.1 g of 1-tert-butoxycarbonylpiperidin-4-yl methacrylate, 19.3 g of 1-(1-methylethyl)cyclopentyl methacrylate, 9.2 g of 2-oxo-4-oxahexahydro-3,5-methano-2H-cyclopenta[b]furan-6-yl methacrylate, 10.4 g of 2-oxotetrahydrofuran-3-yl methacrylate, 2.3 g of dimethyl 2,2'-azobis(2-methylpropionate) (V-601 by Wako Pure Chemical Industries, Ltd.), and 70 g of methyl ethyl ketone (MEK) to form a monomer/initiator solution. Another flask under a nitrogen blanket was charged with 25 g of MEK and heated at 80° C. with stirring, after which the monomer/initiator solution was added dropwise over 4 hours. After the completion of dropwise addition, the polymerization solution was continuously stirred for 2 hours while keeping the temperature of 80° C. It was then cooled to room temperature. With vigorous stirring, the polymerization solution was added dropwise to 500 g of methanol where a copolymer precipitated. The copolymer was collected by filtration, washed twice with 0.3 kg of hexane, and vacuum dried at 50° C. for 20 hours, obtaining 35 g of the copolymer in white powder form (designated Polymer 1). The copolymer was analyzed by $^{13}C$-NMR spectroscopy, finding a copolymer compositional ratio of 2.0/44.4/22.2/31.4 mol % in the described order of monomers. On GPC analysis, the copolymer had a Mw of 6,200.

Polymer-1

(a = 0.020, b = 0.444, c = 0.222, d = 0.314, Mw = 6200)

Synthesis Examples 2-2 to 2-11 & Comparative Synthesis Examples 1 to 3

Synthesis of Polymers 2 to 11 and Polymers X, Y and Z

Polymers (Polymers 2 to 11 and Polymers X, Y and Z) were prepared by the same procedure as in Synthesis Example 2-1 except that the type and amount of monomers used were changed.

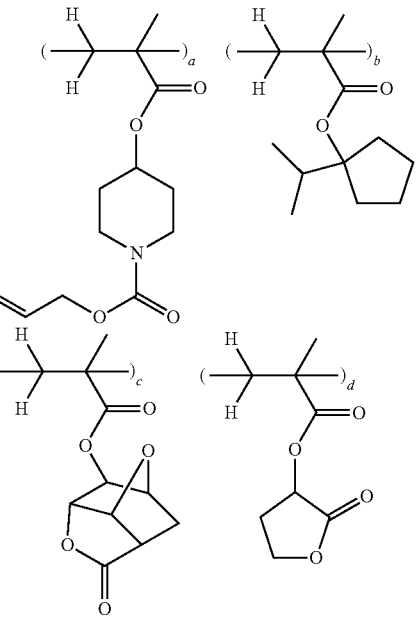

Polymer-2

(a = 0.022, b = 0.445, c = 0.220, d = 0.313, Mw = 6,100)

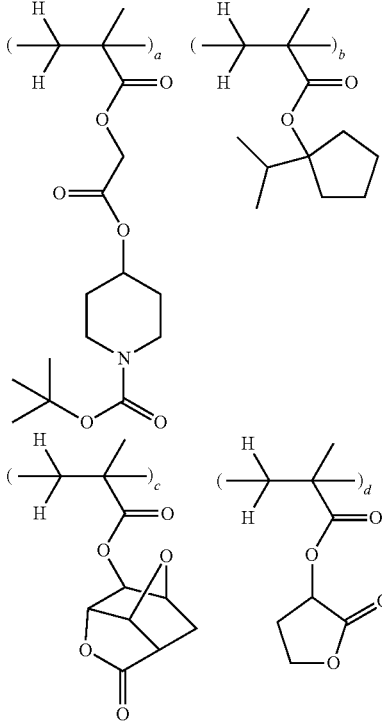

Polymer-3

(a = 0.024, b = 0.443, c = 0.220, d = 0.313, Mw = 6,300)

Polymer-4
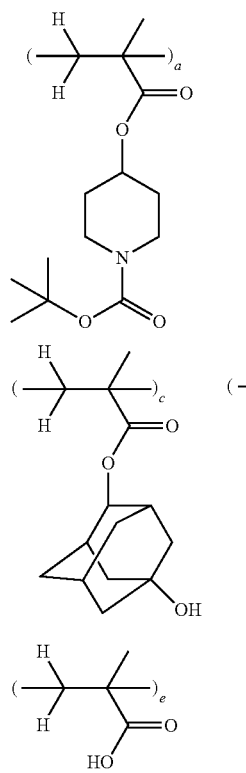
(a = 0.021, b = 0.350, c = 0.230, d = 0.350, e = 0.049, Mw = 5,860)
Polymer-5
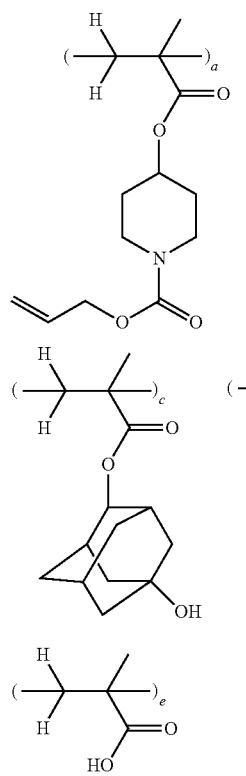
(a = 0.020, b = 0.351, c = 0.230, d = 0.350, e = 0.049, Mw = 5,730)
Polymer-6 / Polymer-7
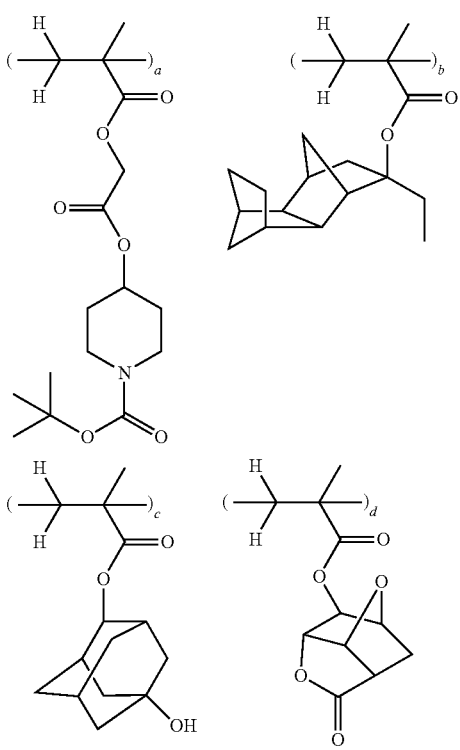
(a = 0.023, b = 0.348, c = 0.230, d = 0.349, e = 0.050, Mw = 5,890)

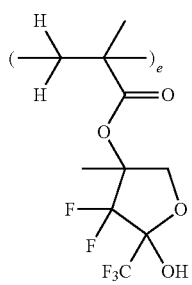
(a = 0.022, b = 0.276, c = 0.227, d = 0.379, e = 0.096, Mw = 6,490)
Polymer-8
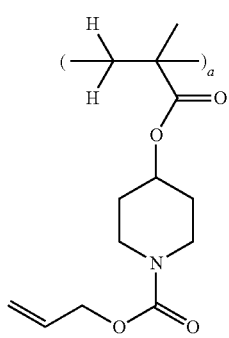
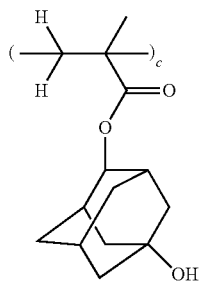
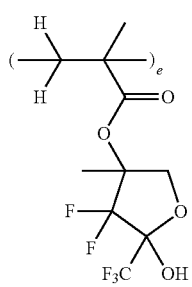
(a = 0.020, b = 0.276, c = 0.229, d = 0.377, e = 0.098, Mw = 6,430)
Polymer-9
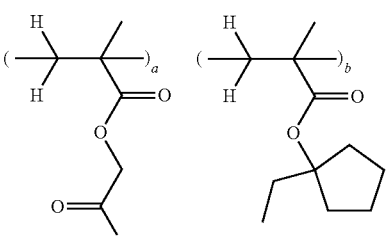
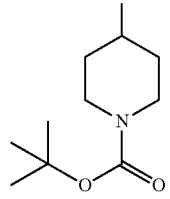
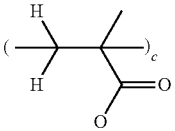
(a = 0.023, b = 0.275, c = 0.229, d = 0.377, e = 0.096, Mw = 6,500)
Polymer-10
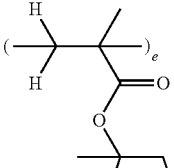
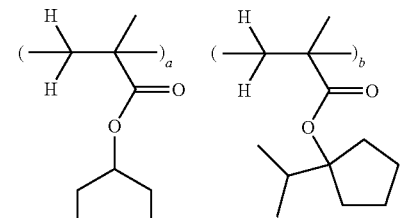
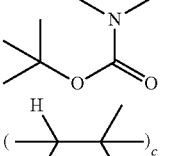
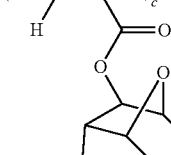
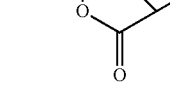

-continued
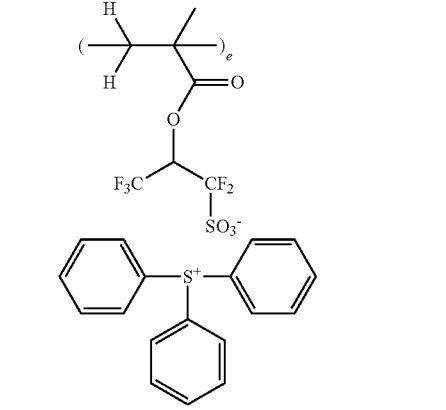
(a = 0.020, b = 0.484, c = 0.149, d = 0.296, e = 0.051, Mw = 6,200)
Polymer-11
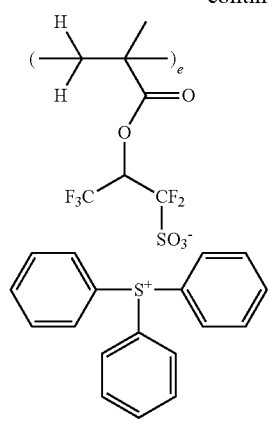
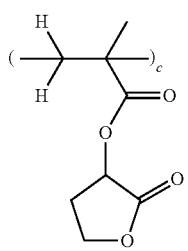
(a = 0.020, b = 0.200, c = 0.200, d = 0.380, e = 0.100, Mw = 5,860)
-continued
Polymer-X
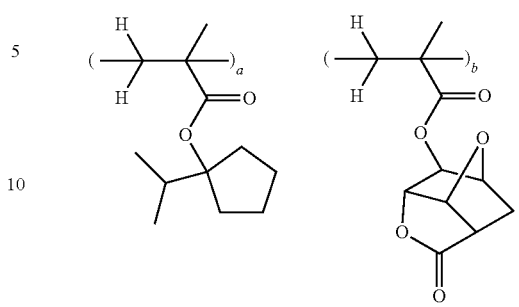
(a = 0.464, b = 0.222, c = 0.314, Mw = 6,100)
Polymer-Y
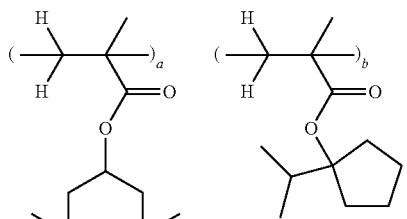
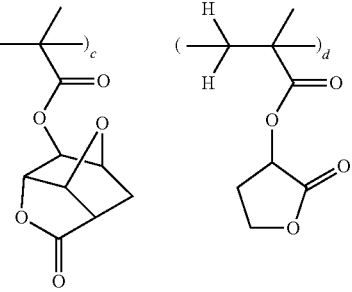
(a = 0.023, b = 0.443, c = 0.218, d = 0.316, Mw = 6,200)
Polymer-Z
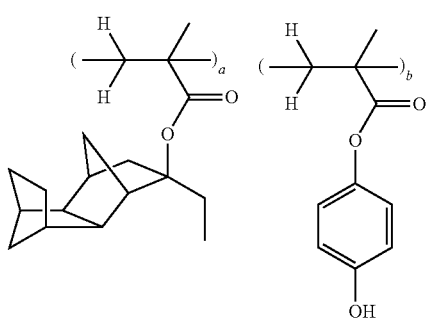

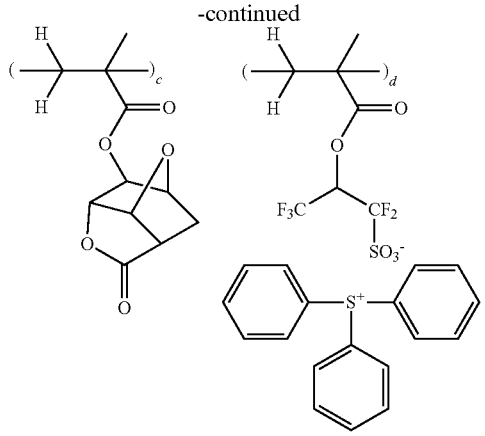

(a = 0.200, b = 0.200, c = 0.500, d = 0.100, Mw = 5,860)

droxy-6-methyl-2-trifluoromethylhept-4-ylmethacrylate) of the formula below, described in JP-A 2008-122932

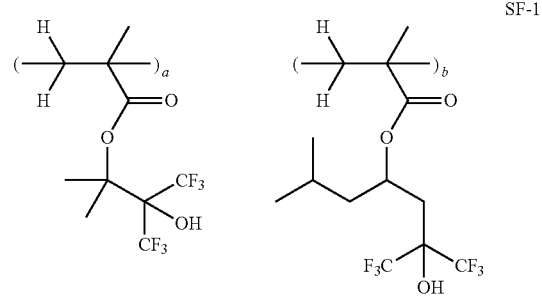

(a = 0.5, b = 0.5, Mw = 7,300)

Surfactant A:
3-methyl-3-(2,2,2-trifluoroethoxymethyl)oxetane/tetrahydrofuran/2,2-dimethyl-1,3-propanediol copolymer of the formula below (Omnova Solutions, Inc.)

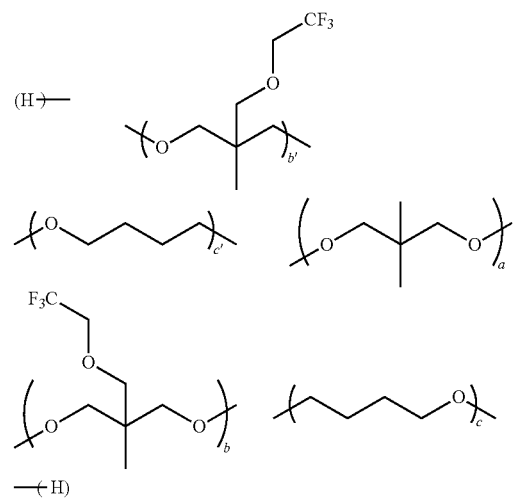

a:(b + b'):(c + c') = 1:4-7:0.01-1 (molar ratio)  MW = 1,500

Examples 1-1 to 1-22 & Comparative Examples 1-1 to 1-4

Preparation of ArF Resist Solution

A resist solution was prepared by dissolving a polymer (in Synthesis Examples) and components in solvents in accordance with the formulation of Table 1 and filtering through a Teflon® filter with a pore size of 0.2 μm. The solvent contained 0.01 wt % of surfactant A from Omnova Solutions, Inc.

The polymer, PAG, solvent, alkali-soluble surfactant SF-1 and quencher in Table 1 are identified below.

P-1 to P-10: Polymers 1 to 10
P-X: Polymer X
P-Y: Polymer Y
PAG-1: triphenylsulfonium 2-(adamantane-1-carbonyloxy)-1,1,3,3,3-pentafluoropropane-1-sulfonate
PAG-2: 4-hydroxy-1-naphthyltetrahydrothiophenium 2-(adamantane-1-carbonyloxy)-1,1,3,3,3-pentafluoropropane-1-sulfonate
PGMEA: propylene glycol monomethyl ether acetate
GBL: γ-butyrolactone
Q-1: 2-morpholinoethyl cyclohexanecarboxylate
Q-2: triphenylsulfonium 10-camphorsulfonate
Alkali-soluble surfactant SF-1:
poly(3,3,3-trifluoro-2-hydroxy-1,1-dimethyl-2-trifluoromethylpropyl methacrylate-co-1,1,1-trifluoro-2-hy-

TABLE 1

| | | Resist | Resin (pbw) | PAG (pbw) | Quencher (pbw) | Alkali-soluble surfactant (pbw) | Solvent 1 (pbw) | Solvent 2 (pbw) |
|---|---|---|---|---|---|---|---|---|
| Example | 1-1 | R-1 | P-1 (80) | PAG-1 (10.1) | — | SF-1 (5.0) | PGMEA (2,700) | GBL (300) |
| | 1-2 | R-2 | P-1 (80) | PAG-2 (9.7) | — | SF-1 (5.0) | PGMEA (2,700) | GBL (300) |
| | 1-3 | R-3 | P-2 (80) | PAG-1 (10.1) | — | SF-1 (5.0) | PGMEA (2,700) | GBL (300) |
| | 1-4 | R-4 | P-2 (80) | PAG-2 (9.7) | — | SF-1 (5.0) | PGMEA (2,700) | GBL (300) |
| | 1-5 | R-5 | P-3 (80) | PAG-1 (10.1) | — | SF-1 (5.0) | PGMEA (2,700) | GBL (300) |
| | 1-6 | R-6 | P-3 (80) | PAG-2 (9.7) | — | SF-1 (5.0) | PGMEA (2,700) | GBL (300) |
| | 1-7 | R-7 | P-4 (80) | PAG-1 (10.1) | — | SF-1 (5.0) | PGMEA (2,700) | GBL (300) |
| | 1-8 | R-8 | P-4 (80) | PAG-2 (9.7) | — | SF-1 (5.0) | PGMEA (2,700) | GBL (300) |

TABLE 1-continued

| | Resist | Resin (pbw) | PAG (pbw) | Quencher (pbw) | Alkali-soluble surfactant (pbw) | Solvent 1 (pbw) | Solvent 2 (pbw) |
|---|---|---|---|---|---|---|---|
| 1-9 | R-9 | P-5 (80) | PAG-1 (10.1) | — | SF-1 (5.0) | PGMEA (2,700) | GBL (300) |
| 1-10 | R-10 | P-5 (80) | PAG-2 (9.7) | — | SF-1 (5.0) | PGMEA (2,700) | GBL (300) |
| 1-11 | R-11 | P-6 (80) | PAG-1 (10.1) | — | SF-1 (5.0) | PGMEA (2,700) | GBL (300) |
| 1-12 | R-12 | P-6 (80) | PAG-2 (9.7) | — | SF-1 (5.0) | PGMEA (2,700) | GBL (300) |
| 1-13 | R-13 | P-7 (80) | PAG-1 (10.1) | — | SF-1 (5.0) | PGMEA (2,700) | GBL (300) |
| 1-14 | R-14 | P-7 (80) | PAG-2 (9.7) | — | SF-1 (5.0) | PGMEA (2,700) | GBL (300) |
| 1-15 | R-15 | P-8 (80) | PAG-1 (10.1) | — | SF-1 (5.0) | PGMEA (2,700) | GBL (300) |
| 1-16 | R-16 | P-8 (80) | PAG-2 (9.7) | — | SF-1 (5.0) | PGMEA (2,700) | GBL (300) |
| 1-17 | R-17 | P-9 (80) | PAG-1 (10.1) | — | SF-1 (5.0) | PGMEA (2,700) | GBL (300) |
| 1-18 | R-18 | P-9 (80) | PAG-2 (9.7) | — | SF-1 (5.0) | PGMEA (2,700) | GBL (300) |
| 1-19 | R-19 | P-10 (80) | — | — | SF-1 (5.0) | PGMEA (2,700) | GBL (300) |
| 1-20 | R-20 | P-1 (80) | PAG-1 (10.1) | Q-1 (1.0) | SF-1 (5.0) | PGMEA (2,700) | GBL (300) |
| 1-21 | R-21 | P-1 (80) | PAG-1 (10.1) | Q-2 (3.8) | SF-1 (5.0) | PGMEA (2,700) | GBL (300) |
| 1-22 | R-22 | P-1 + P-X (70 + 10) | PAG-1 (10.1) | — | SF-1 (5.0) | PGMEA (2,700) | GBL (300) |
| Comparative Example 1-1 | R-23 | P-X (80) | PAG-1 (10.1) | Q-1 (1.0) | SF-1 (5.0) | PGMEA (2,700) | GBL (300) |
| 1-2 | R-24 | P-X (80) | PAG-2 (9.7) | Q-1 (1.0) | SF-1 (5.0) | PGMEA (2,700) | GBL (300) |
| 1-3 | R-25 | P-Y (80) | PAG-1 (10.1) | — | SF-1 (5.0) | PGMEA (2,700) | GBL (300) |
| 1-4 | R-26 | P-Y (80) | PAG-2 (9.7) | — | SF-1 (5.0) | PGMEA (2,700) | GBL (300) |

ArF Lithography Patterning Test

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A941 having a silicon content of 43 wt % was deposited thereon to a thickness of 35 nm. On this substrate for trilayer process, the resist composition (R-1 to R-22 & comparative R-23 to R26) shown in Table 1 was spin coated, then baked on a hot plate at 100° C. for 60 seconds to form a resist film of 90 nm thick.

Using an ArF excimer laser immersion lithography scanner NSR-610C (Nikon Corp., NA 1.30, σ0.98/0.78, dipole opening 35 deg., azimuthally polarized illumination), exposure was performed in a varying dose through a 6% halftone phase shift mask bearing a trench pattern. After the exposure, the wafer was baked (PEB) at the temperature shown in Table 2 for 60 seconds and puddle developed with a 2.38 wt % TMAH aqueous solution for 30 seconds. The wafer was rinsed with deionized water and spin dried.

The resist was evaluated. The exposure dose (mJ/cm$^2$) at which a 50-nm trench pattern with a pitch of 150 nm was resolved was an optimum dose (Eop). The profile and line width roughness (LWR) of the pattern printed at the optimum dose were determined under a scanning electron microscope S-9380 (Hitachi Hitechnologies, Ltd.).

The profile of a trench pattern was rated according to the following criterion.

Rectangular: satisfactory, perpendicular pattern sidewall, little size change from bottom (near substrate) to top T-top: unsatisfactory, size increase near top (caused, in part, by volatilization of amine quencher during PEB)

The test results of the resist compositions are shown in Table 2 together with the PEB temperature.

TABLE 2

| | Resist | PEB temp. (° C.) | Eop (mJ/cm$^2$) | Pattern profile | LWR (nm) |
|---|---|---|---|---|---|
| Example 1-1 | R-1 | 80 | 21 | rectangular | 3.4 |
| Example 1-2 | R-2 | 80 | 45 | rectangular | 3.4 |
| Example 1-3 | R-3 | 80 | 18 | rectangular | 3.3 |
| Example 1-4 | R-4 | 80 | 43 | rectangular | 3.5 |
| Example 1-5 | R-5 | 80 | 22 | rectangular | 3.3 |
| Example 1-6 | R-6 | 80 | 47 | rectangular | 3.4 |
| Example 1-7 | R-7 | 110 | 25 | rectangular | 4.2 |
| Example 1-8 | R-8 | 110 | 52 | rectangular | 4.1 |
| Example 1-9 | R-9 | 110 | 24 | rectangular | 3.9 |
| Example 1-10 | R-10 | 110 | 50 | rectangular | 3.9 |
| Example 1-11 | R-11 | 110 | 26 | rectangular | 4.0 |
| Example 1-12 | R-12 | 110 | 51 | rectangular | 3.8 |
| Example 1-13 | R-13 | 90 | 28 | rectangular | 3.5 |
| Example 1-14 | R-14 | 90 | 59 | rectangular | 3.4 |
| Example 1-15 | R-15 | 90 | 25 | rectangular | 3.4 |
| Example 1-16 | R-16 | 90 | 50 | rectangular | 3.6 |
| Example 1-17 | R-17 | 90 | 27 | rectangular | 3.7 |
| Example 1-18 | R-18 | 90 | 56 | rectangular | 3.5 |
| Example 1-19 | R-19 | 80 | 33 | rectangular | 3.4 |
| Example 1-20 | R-20 | 80 | 29 | rectangular | 3.5 |
| Example 1-21 | R-21 | 80 | 33 | rectangular | 3.3 |
| Example 1-22 | R-22 | 80 | 28 | rectangular | 3.4 |
| Comparative Example 1-1 | R-23 | 80 | 40 | T-top | 5.6 |

TABLE 2-continued

| Resist | PEB temp. (° C.) | Eop (mJ/cm$^2$) | Pattern profile | LWR (nm) |
|---|---|---|---|---|
| Comparative Example 1-2 | R-24 | 80 | 74 | T-top | 6.1 |
| Comparative Example 1-3 | R-25 | 80 | 35 | T-top | 5.8 |
| Comparative Example 1-4 | R-26 | 80 | 68 | T-top | 5.5 |

Examples 2-1 to 2-3 & Comparative Examples 2-1 to 2-2

Shelf Stability Test

Some resist solutions prepared according to the formulation of Table 1 were aged at 30° C. for one month, after which a pattern was similarly formed. An Eop value of the 1 month aged solution was determined and compared with the Eop of the fresh solution. A sensitivity change was calculated by the following equation.

Sensitivity change (%)=[(aged $Eop$)−(fresh $Eop$)]/(fresh $Eop$)×100

A negative value means that the resist has increased its sensitivity. A smaller absolute value indicates that the resist composition undergoes a least change with time and is shelf stable. The results are shown in Table 3.

TABLE 3

|  | Resist | Sensitivity change (%) |
|---|---|---|
| Example 2-1 | R-2 | 0 |
| Example 2-2 | R-4 | 0 |
| Example 2-3 | R-6 | 0 |
| Comparative Example 2-1 | R-24 | −5 |
| Comparative Example 2-2 | R-26 | −6 |

EUV Lithography Test

A positive resist composition was prepared by dissolving Polymer 11 (Synthesis Example) or Polymer Z and selected components in a solvent in accordance with the recipe shown in Table 4, and filtering through a filter having a pore size of 0.2 μm.

The polymer, quencher, and solvent in Table 4 are identified below.

P-11: Polymer 11
P-Z: Polymer Z
PGMEA: propylene glycol monomethyl ether acetate
CyH: cyclohexanone
PGME: propylene glycol monomethyl ether
Q-3: 2-morpholinoethyl n-dodecanoate The resist composition was spin coated on a silicon substrate (diameter 4 inches, vapor primed with hexamethyl disilazane (HMDS)) and prebaked on a hot plate at 105° C. for 60 seconds to form a resist film of 50 nm thick. EUV exposure was performed by dipole illumination at NA 0.3.

Immediately after the exposure, the resist film was baked (PEB) on a hot plate for 60 seconds and puddle developed with a 2.38 wt % TMAH aqueous solution for 30 seconds to form a positive pattern.

Resolution is a minimum size at the exposure dose (Eop) that provides a 1:1 resolution of a 35-nm line-and-space pattern. The 35-nm line-and-space pattern was measured for line width roughness (LWR) under SEM (S-4300).

The resist composition is shown in Table 4 together with the sensitivity and resolution of EUV lithography.

TABLE 4

|  | Resist | Polymer (pbw) | Quencher (pbw) | Solvent (pbw) | PEB temperature (° C.) | Eop (mJ/cm$^2$) | Pattern profile | Resolution (nm) | LWR (nm) |
|---|---|---|---|---|---|---|---|---|---|
| Example 3-1 | R-27 | P-11 (80) | — | PGMEA (1,000) CyH (2,000) PGME (500) | 90 | 12 | rectangular | 22 | 3.3 |
| Comparative Example 3-1 | R-28 | P-Z (80) | Q-3 (1.0) | PGMEA (1,000) CyH (2,000) PGME (500) | 90 | 14 | rectangular | 24 | 4.3 |

It is evident from Tables 2 and 3 that the resist compositions using polymers from the inventive nitrogen-containing monomers form trench patterns of rectangular profile with improved LWR. This is because the incorporation of quencher component in the resist polymer in bonded form prevents volatilization of amine component and helps form a pattern profile of high rectangularity and free of chemical flare, in stark contrast with the prior art resist compositions having an amine quencher separately added. In addition, the inventive resist compositions undergo no sensitivity change during shelf storage and are compatible with PAGs such as alkylsulfonium salts.

It is seen from the results of the EUV exposure test in Table 4 that the inventive resist composition, when processed by EUV lithography, is improved in resolution and LWR over the prior art resist composition having an amine quencher separately added.

It has been demonstrated that the inventive resist compositions using polymers from the inventive nitrogen-containing monomers form patterns of rectangular profile with minimized roughness at a high resolution and are improved in shelf stability, obviating the drawback of alkylsulfonium salts.

Japanese Patent Application No. 2011-005428 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A chemically amplified positive resist composition comprising 100 parts by weight of a polymer comprising recurring units (a) having the formula (2), at least one of recurring units (b) and (c) represented by the general formula (3) and having an acid labile group-substituted carboxyl and/or hydroxyl group, and recurring units (d) having an adhesive group selected from among hydroxyl, carboxyl, lactone ring, carbonate, thiocarbonate, carbonyl, cyclic acetal, ether, ester, sulfonic acid ester, cyano, amide, and —O—C(=O)-G- wherein G is sulfur or NH, 50 to 10,000 parts by weight of an organic solvent, 0.01 to 100 parts by weight of an acid generator in the form of a sulfonium salt having the general formula (15), 0 to 100 parts by weight of a basic compound, and 0 to 10 parts by weight of a surfactant,

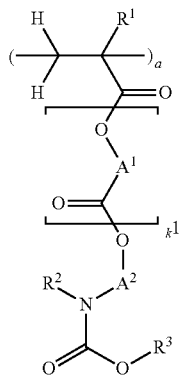

(2)

wherein $R^1$ is hydrogen, fluorine, methyl or trifluoromethyl, $R^2$ is hydrogen or a straight, branched or cyclic, mono or divalent hydrocarbon group of 1 to 10 carbon atoms, $R^3$ is an acid labile group of 1 to 15 carbon atoms, $A^1$ is a straight, branched or cyclic, divalent hydrocarbon group of 1 to 10 carbon atoms, $A^2$ is a straight, branched or cyclic, di or trivalent hydrocarbon group of 1 to 10 carbon atoms, $A^2$ and $R^2$ may bond together to form a ring with the adjacent nitrogen atom, $k^1$ is 0, $R^3$ is an acid labile group selected from the following:

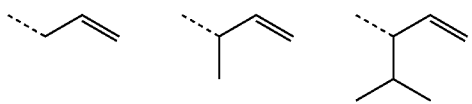

wherein the broken line denotes a valence bond, and "a" is a number in the range: $0 < a < 1.0$,

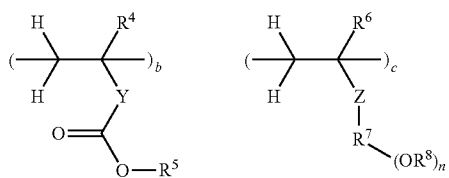

(3)

wherein $R^4$ and $R^6$ each are hydrogen or methyl; $R^5$ and $R^8$ each are an acid labile group; $R^7$ is a straight, branched or cyclic $C_1$-$C_{10}$ alkylene group or a trivalent form of the alkylene group with one hydrogen eliminated, which may contain an ether or ester moiety, or a phenylene or naphthylene group; Y is a single bond or —C(=O)—O—$R^9$—; $R^9$ is a straight, branched or cyclic $C_1$-$C_{10}$ alkylene group which may contain an ether or ester moiety, or a phenylene or naphthylene group; Z is a single bond or —C(=O)—O—$R^{10}$—; $R^{10}$ is a straight, branched or cyclic $C_1$-$C_{10}$ alkylene group which may contain an ether or ester moiety, or a phenylene or naphthylene group; the phenylene and naphthylene groups may be substituted with fluorine, trifluoromethyl, cyano, amide or $C_1$-$C_6$ alkyl or alkoxy radical; n is 1 or 2, b and c are numbers in the range: $0 \leq b < 1.0$, $0 \leq c < 1.0$, and $0 < b+c < 1$,

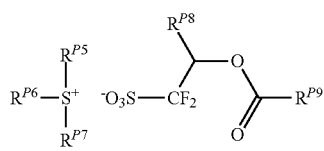

(15)

wherein $R^{p5}$, $R^{p6}$, and $R^{p7}$ are each independently a straight, or branched $C_1$-$C_{10}$ alkyl, alkenyl or oxoalkenyl group which may contain fluorine, hydroxyl or ether bond, or a substituted or unsubstituted $C_6$-$C_{18}$ aryl, aralkyl or aryloxoalkyl group, alternatively, any two or more of $R^{p5}$, $R^{p6}$, and $R^{p7}$ may bond together to form a ring with the sulfur atom, $R^{p8}$ is hydrogen or trifluoromethyl, $R^{p9}$ is a straight, branched or cyclic $C_6$-$C_{30}$ monovalent hydrocarbon group which may contain a heteroatom.

2. A pattern forming process comprising the steps of coating the chemically amplified positive resist composition of claim 1 onto a substrate, baking, exposing to high-energy radiation, and developing with a developer.

3. The pattern forming process of claim 2 wherein the high-energy radiation is selected from the group consisting of g-line, i-line, KrF excimer laser, ArF excimer laser, electron beam, and soft x-ray with a wavelength 3 to 15 nm.

4. The chemically amplified positive resist composition of claim 1 wherein the recurring units (a) are units formed from a monomer selected from the group consisting of the following formulae:

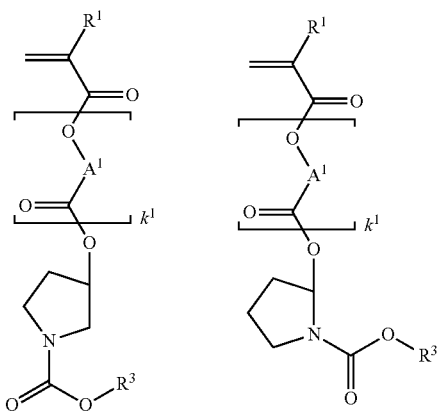

-continued

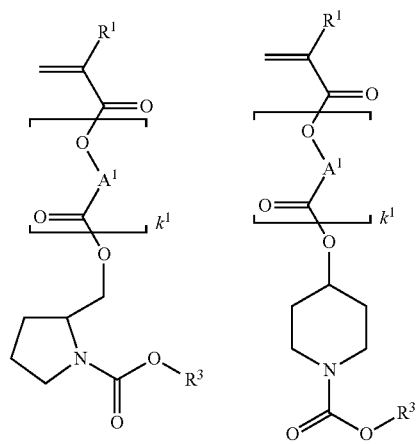
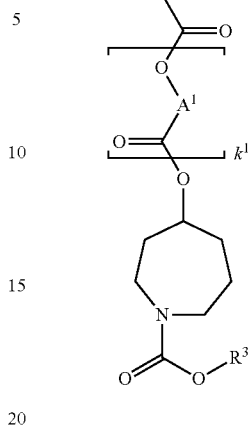
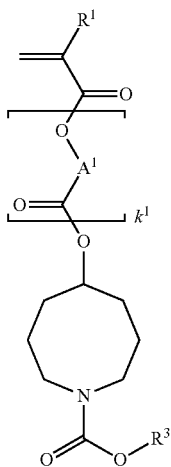

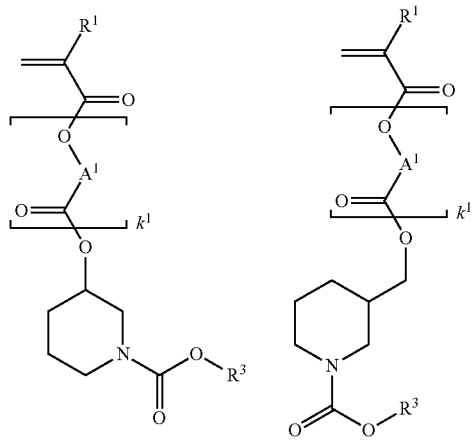

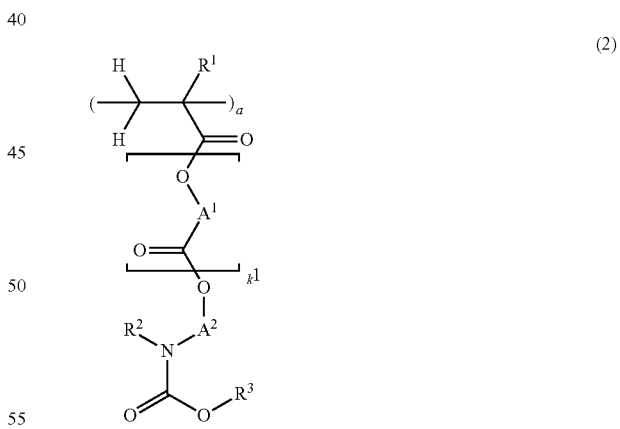

wherein $R^1$, $R^3$, $A^1$ and $k^1$ are as defined above.

5. A chemically amplified positive resist composition comprising 100 parts by weight of a polymer comprising recurring units (a) having the formula (2), any one of recurring units, (e2) having a sulfonium salt represented by the general formula (13), at least one of recurring units (b) and (c) represented by the general formula (3) and having an acid labile group-substituted carboxyl and/or hydroxyl group, and recurring units (d) having an adhesive group selected from among hydroxyl, carboxyl, lactone ring, carbonate, thiocarbonate, carbonyl, cyclic acetal, ether, ester, sulfonic acid ester, cyano, amide, and —O—C(=O)-G- wherein G is sulfur or NH, 50 to 10,000 parts by weight of an organic solvent, 0 to 100 parts by weight of a basic compound, and 0 to 10 parts by weight of a surfactant, (2)

wherein $R^1$ is hydrogen, fluorine, methyl or trifluoromethyl, $R^2$ is hydrogen or a straight, branched or cyclic, mono or divalent hydrocarbon group of 1 to 10 carbon atoms, $R^3$ is an acid labile group of 1 to 15 carbon atoms, $A^1$ is a straight, branched or cyclic, divalent hydrocarbon group of 1 to 10 carbon atoms, $A^2$ is a straight, branched or cyclic, di or trivalent hydrocarbon group of 1 to 10 carbon atoms, $A^2$ and $R^2$ may bond together to form a ring with the adjacent nitrogen atom, $k^1$ is 0, $R^3$ is an acid labile group selected from the following:

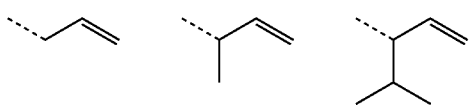

wherein the broken line denotes a valence bond, and "a" is a number in the range: 0<a<1.0,

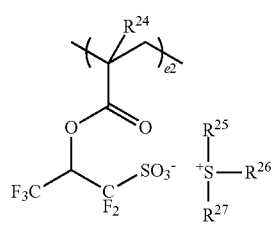
(13)

wherein $R^{24}$ is hydrogen or methyl, $R^{25}$, $R^{26}$ and $R^{27}$ are each independently a straight, branched or cyclic $C_1$-$C_{12}$ alkyl group which may contain a carbonyl, ester or ether radical, or a $C_6$-$C_{12}$ aryl group, $C_7$-$C_{20}$ aralkyl group, or thiophenyl group,

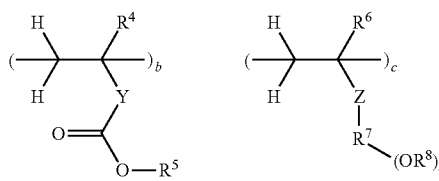
(3)

wherein $R^4$ and $R^6$ each are hydrogen or methyl; $R^5$ and $R^8$ each are an acid labile group; $R^7$ is a straight, branched or cyclic $C_1$-$C_{10}$ alkylene group or a trivalent form of the alkylene group with one hydrogen eliminated, which may contain an ether or ester moiety, or a phenylene or naphthylene group; Y is a single bond or —C(=O)—O—$R^9$—; $R^9$ is a straight, branched or cyclic $C_1$-$C_{10}$ alkylene group which may contain an ether or ester moiety, or a phenylene or naphthylene group; Z is a single bond or —C(=O)—O—$R^{10}$—; $R^{10}$ is a straight, branched or cyclic $C_1$-$C_{10}$ alkylene group which may contain an ether or ester moiety, or a phenylene or naphthylene group; the phenylene and naphthylene groups may be substituted with fluorine, trifluoromethyl, cyano, amide or $C_1$-$C_6$ alkyl or alkoxy radical; n is 1 or 2, b and c are numbers in the range: 0≤b<1.0, 0≤c<1.0, and 0<b+c<1.

6. A pattern forming process comprising the steps of coating the chemically amplified positive resist composition of claim 5 onto a substrate, baking, exposing to high-energy radiation, and developing with a developer.

7. The pattern forming process of claim 6 wherein the high-energy radiation is selected from the group consisting of g-line, i-line, KrF excimer laser, ArF excimer laser, electron beam, and soft x-ray with a wavelength 3 to 15 nm.

8. The chemically amplified positive resist composition of claim 5 wherein the recurring units (a) are units formed from a monomer selected from the group consisting of the following formulae:

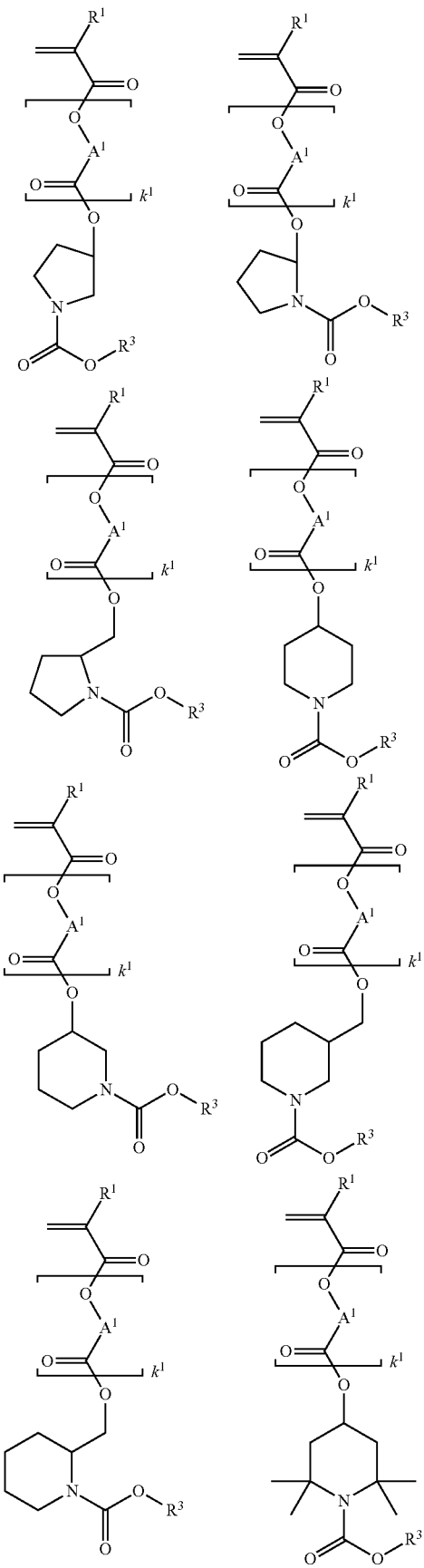

-continued

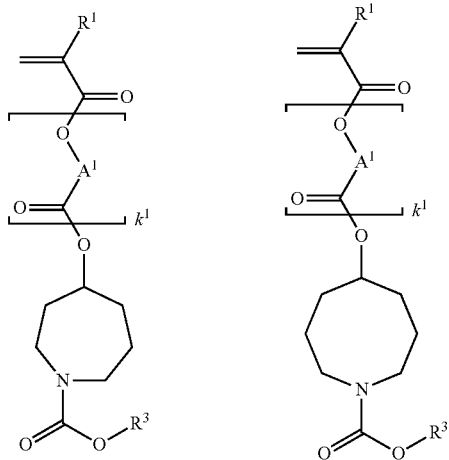

wherein $R^1$, $R^3$, $A^1$ and $k^1$ are as defined above.

9. The resist composition of claim 5 which further comprises 0.01 to 100 parts by weight of an acid generator in the form of a sulfonium salt having the general formula (15):

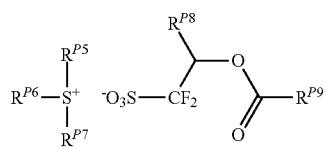

(15)

wherein $R^{P5}$, $R^{P6}$, and $R^{P7}$ are each independently a straight, or branched $C_1$-$C_{10}$ alkyl, alkenyl or oxoalkenyl group which may contain fluorine, hydroxyl or ether bond, or a substituted or unsubstituted $C_6$-$C_{18}$ aryl, aralkyl or aryloxoalkyl group, alternatively, any two or more of $R^{P5}$, $R^{P6}$, and $R^{P7}$ may bond together to form a ring with the sulfur atom, $R^{P8}$ is hydrogen or trifluoromethyl, and $R^{P9}$ is a straight, branched or cyclic $C_6$-$C_{30}$ monovalent hydrocarbon group which may contain a heteroatom.

10. A chemically amplified positive resist composition comprising 100 parts by weight of a polymer comprising recurring units (a) having the formula (2), at least one of recurring units (b) and (c) represented by the general formula (3) and having an acid labile group-substituted carboxyl and/or hydroxyl group, and recurring units (d) having an adhesive group selected from among hydroxyl, carboxyl, lactone ring, carbonate, thiocarbonate, carbonyl, cyclic acetal, ether, ester, sulfonic acid ester, cyano, amide, and —O—C(=O)-G- wherein G is sulfur or NH, 50 to 10,000 parts by weight of an organic solvent, 0.01 to 100 parts by weight of an acid generator in the form of a sulfonium salt having the general formula (15), 0 to 100 parts by weight of a basic compound, and 0 to 10 parts by weight of a surfactant,

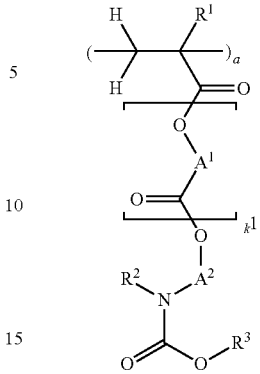

(2)

wherein $R^1$ is hydrogen, fluorine, methyl or trifluoromethyl, $R^2$ is hydrogen or a straight, branched or cyclic, mono or divalent hydrocarbon group of 1 to 10 carbon atoms, $R^3$ is an acid labile group of 1 to 15 carbon atoms, $A^1$ is a straight, branched or cyclic, divalent hydrocarbon group of 1 to 10 carbon atoms, $A^2$ is a straight, branched or cyclic, di or trivalent hydrocarbon group of 1 to 10 carbon atoms, $A^2$ and $R^2$ may bond together to form a ring with the adjacent nitrogen atom, $k^1$ is 1, $R^3$ is an acid labile group selected from the following:

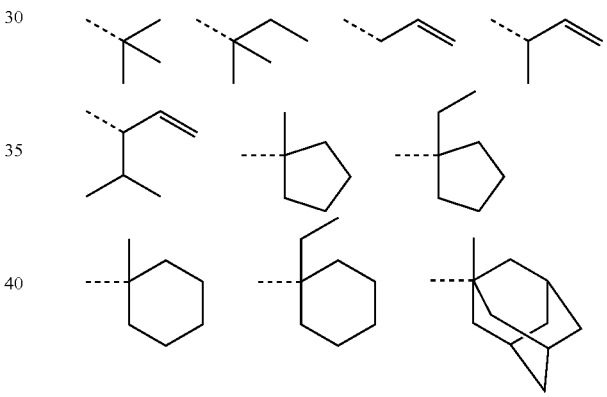

wherein the broken line denotes a valence bond, and "a" is a number in the range: $0<a<1.0$,

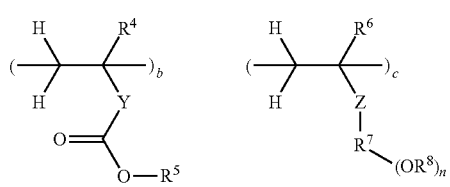

(3)

wherein $R^4$ and $R^6$ each are hydrogen or methyl; $R^5$ and $R^8$ each are an acid labile group; $R^7$ is a straight, branched or cyclic $C_1$-$C_{10}$ alkylene group or a trivalent form of the alkylene group with one hydrogen eliminated, which may contain an ether or ester moiety, or a phenylene or naphthylene group; Y is a single bond or —C(=O)—O—$R^9$—; $R^9$ is a straight, branched or cyclic $C_1$-$C_{10}$ alkylene group which may contain an ether or ester moiety, or a phenylene or naphthylene group; Z is a single bond or —C(=O)—O—$R^{10}$—; $R^{10}$ is a straight, branched or cyclic $C_1$-$C_{10}$ alkylene group which may contain an ether or ester moiety, or a phenylene or naphthylene group; the phenylene and naphthylene groups may be substituted with fluorine, trifluoromethyl, cyano, amide or $C_1$-$C_6$ alkyl or alkoxy radical; n is 1 or 2, b and c are numbers in the range: $0 \leq b < 1.0$, $0 \leq c < 1.0$, and $0 < b+c < 1$,

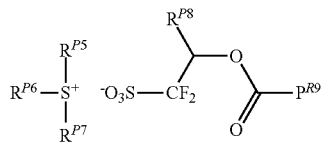
(15)

wherein $R^{p5}$, $R^{p6}$, and $R^{p7}$ are each independently a straight, or branched $C_1$-$C_{10}$ alkyl, alkenyl or oxoalkenyl group which may contain fluorine, hydroxyl or ether bond, or a substituted or unsubstituted $C_6$-$C_{18}$ aryl, aralkyl or aryloxoalkyl group, alternatively, any two or more of $R^{p5}$, $R^{p6}$, and $R^{p7}$ may bond together to form a ring with the sulfur atom, $R^{p8}$ is hydrogen or trifluoromethyl, $R^{p9}$ is a straight, branched or cyclic $C_6$-$C_{30}$ monovalent hydrocarbon group which may contain a heteroatom.

11. A pattern forming process comprising the steps of coating the chemically amplified positive resist composition of claim 10 onto a substrate, baking, exposing to high-energy radiation, and developing with a developer.

12. A chemically amplified positive resist composition comprising 100 parts by weight of a polymer comprising recurring units (a) having the formula (2), any one of recurring units (e2) having a sulfonium salt represented by the general formula (13), at least one of recurring units (b) and (c) represented by the general formula (3) and having an acid labile group-substituted carboxyl and/or hydroxyl group, and recurring units (d) having an adhesive group selected from among hydroxyl, carboxyl, lactone ring, carbonate, thiocarbonate, carbonyl, cyclic acetal, ether, ester, sulfonic acid ester, cyano, amide, and —O—C(=O)-G- wherein G is sulfur or NH, 50 to 10,000 parts by weight of an organic solvent, 0 to 100 parts by weight of a basic compound, and 0 to 10 parts by weight of a surfactant,

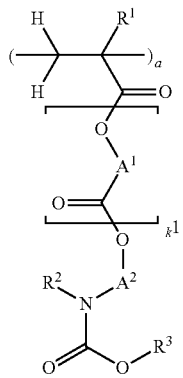
(2)

wherein $R^1$ is hydrogen, fluorine, methyl or trifluoromethyl, $R^2$ is hydrogen or a straight, branched or cyclic, mono or divalent hydrocarbon group of 1 to 10 carbon atoms, $R^3$ is an acid labile group of 1 to 15 carbon atoms, $A^1$ is a straight, branched or cyclic, divalent hydrocarbon group of 1 to 10 carbon atoms, $A^2$ is a straight, branched or cyclic, di or trivalent hydrocarbon group of 1 to 10 carbon atoms, $A^2$ and $R^2$ may bond together to form a ring with the adjacent nitrogen atom, $k^1$ is 1, $R^3$ is an acid labile group selected from the following:

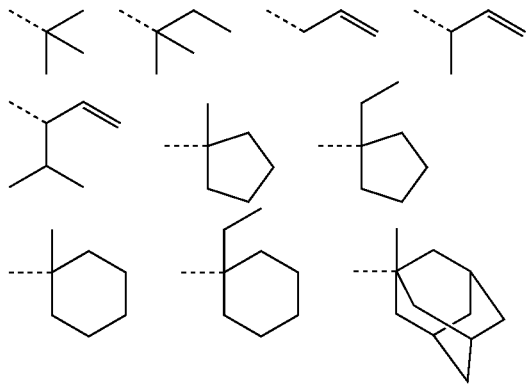

wherein the broken line denotes a valence bond, and "a" is a number in the range: $0 < a < 1.0$,

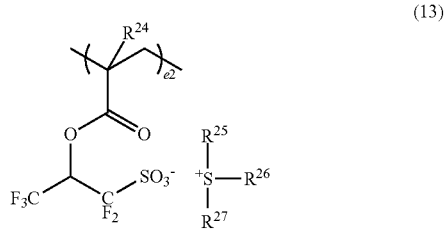
(13)

wherein $R^{24}$ is hydrogen or methyl, $R^{25}$, $R^{26}$ and $R^{27}$ are each independently a straight, branched or cyclic $C_1$-$C_{12}$ alkyl group which may contain a carbonyl, ester or ether radical, or a $C_6$-$C_{12}$ aryl group, $C_7$-$C_{20}$ aralkyl group, or thiophenyl group,

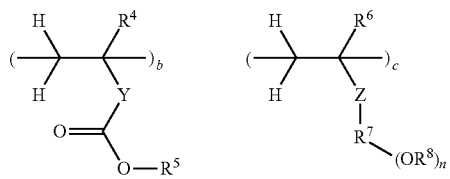
(3)

wherein $R^4$ and $R^6$ each are hydrogen or methyl; $R^5$ and $R^8$ each are an acid labile group; $R^7$ is a straight, branched or cyclic $C_1$-$C_{10}$ alkylene group or a trivalent form of the alkylene group with one hydrogen eliminated, which may contain an ether or ester moiety, or a phenylene or naphthylene group; Y is a single bond or —C(=O)—O—$R^9$—; $R^9$ is a straight, branched or cyclic $C_1$-$C_{10}$ alkylene group which may contain an ether or ester moiety, or a phenylene or naphthylene group; Z is a single bond or —C(=O)—O—$R^{10}$—; $R^{10}$ is a straight, branched or cyclic $C_1$-$C_{10}$ alkylene group which may contain an ether or ester moiety, or a phenylene or naphthylene group; the phenylene and naphthylene groups may be substituted with fluorine, trifluoromethyl, cyano, amide or $C_1$-$C_6$ alkyl or alkoxy radical; n is 1 or 2, b and c are numbers in the range: $0 \leq b < 1.0$, $0 \leq c < 1.0$, and $0 < b+c < 1$.

13. A pattern forming process comprising the steps of coating the chemically amplified positive resist composition of claim 12 onto a substrate, baking, exposing to high-energy radiation, and developing with a developer.

\* \* \* \* \*